(12) United States Patent
Dragovic et al.

(10) Patent No.: US 10,400,244 B2
(45) Date of Patent: Sep. 3, 2019

(54) OLIGONUCLEOTIDE SEQUENCE FOR USE IN PATHWAY ENGINEERING

(71) Applicant: CLARIANT INTERNATIONAL LTD., Muttenz (CH)

(72) Inventors: Zdravko Dragovic, Munich (DE); Christoph Reisinger, Munich (DE); Heiko Dietz, Munich (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 15/529,577

(22) PCT Filed: Nov. 16, 2015

(86) PCT No.: PCT/EP2015/076715
§ 371 (c)(1),
(2) Date: May 25, 2017

(87) PCT Pub. No.: WO2016/083180
PCT Pub. Date: Jun. 2, 2016

(65) Prior Publication Data
US 2017/0314029 A1    Nov. 2, 2017

(30) Foreign Application Priority Data
Nov. 26, 2014 (EP) .................................. 14195026

(51) Int. Cl.
*C12N 15/113* (2010.01)
*C12N 15/79* (2006.01)
*C12N 15/67* (2006.01)

(52) U.S. Cl.
CPC ........ *C12N 15/1137* (2013.01); *C12N 15/113* (2013.01); *C12Y 503/01005* (2013.01)

(58) Field of Classification Search
None
See application file for complete search history.

(56) References Cited

U.S. PATENT DOCUMENTS

| | | | |
|---|---|---|---|
| 7,504,493 B2 * | 3/2009 | Velculescu | C12Q 1/6895 536/24.32 |
| 2010/0120105 A1 * | 5/2010 | Anthony | C12N 9/0006 435/157 |

FOREIGN PATENT DOCUMENTS

| DE | 10 2012 007 491 A1 | 10/2013 |
|---|---|---|
| JP | 2010136627 A | 6/2010 |
| WO | 2003095627 A1 | 11/2003 |
| WO | 2010062597 A1 | 6/2010 |
| WO | 2010151866 A2 | 12/2010 |
| WO | 2014035458 A1 | 3/2014 |
| WO | 2014080024 A2 | 5/2014 |

OTHER PUBLICATIONS

Sequence Alignment of SEQ ID No. 1 with SEQ ID No. 324 USPGPUB 20100120105, Search conducted on Apr. 2, 2019, 2 pages. (Year: 2019).*
Sequence Alignment of SEQ ID No. 1 with SEQ ID No. 12216 of U.S. Pat. No. 7504493. Search conducted on Apr. 2, 2019, 2 pages. (Year: 2019).*

* cited by examiner

*Primary Examiner* — Channing S Mahatan
(74) *Attorney, Agent, or Firm* — Verrill Dana, LLP

(57) ABSTRACT

The present invention comprises a novel artificial oligonucleotide sequence which can initiate the transcription of a gene under various conditions at a high level. Further the invention relates to a recombinant DNA fragment comprising the artificial oligonucleotide sequence, an expression plasmid comprising the recombinant DNA fragment and a host cell transformed with the recombinant DNA fragment.

12 Claims, 4 Drawing Sheets

Specification includes a Sequence Listing.

SEQUENCE LISTING

<160> NUMBER OF SEQ ID NOS: 54

<210> SEQ ID NO 1
<211> LENGTH: 800
<212> TYPE: DNA
<213> ORGANISM: Saccharomyces cerevisiae

<400> SEQUENCE: 1

```
ccattctctg ctgctttgtt gcatcgtatc atcgcccgtt tcagccagtc ccgcataccc     60
cctttgcaac gttaacgtta ccgctagcgt ttaccatctc cacgctaaaa ggaaaacgaa    120
gattaagata aagttgggta aaatccgggg taagaggcaa gggggtagag aaaaaaaaac    180
cggagtcatt atatacgata ccgtccaggg taagacagtg atttctagct tccactttt    240
tcaatttctt ttttttcgttc caaatggcgt ccacccgtac atccggaatc tgacggcaca   300
agagccgatt agtggaagcc acggttacgt gattgcggtt ttttttttcct acgtataacg   360
ctatgacggt agttgaatgt taaaaacgaa aacagagata ttgaattgac tcgtaggaac   420
aatttcgggc cctgcgtgt tcttctgagg ttcatctttt acatttgctt ctgctggata    480
attttcagag gcaacaagga aaattagat ggcaaaaagt cgtctttcaa ggaaaaatcc    540
ccaccatctt tcgagatccc ctgtaactta ttggcaactg aaagaatgaa aaggaggaaa    600
atacaaaata tactagaact gaaaaaaaaa aagtataaat agagacgata tatgccaata    660
cttcacaatg ttcgaatcta ttcttcattt gcagctattg taaaataata aaacatcaag    720
aacaaacaag ctcaacttgt cttttctaag aacaagaat aaacacaaaa acaaaagtt     780
tttttaattt taatcaaaaa                                               800
```

<210> SEQ ID NO 2
<211> LENGTH: 799
<212> TYPE: DNA
<213> ORGANISM: Saccharomyces cerevisiae

<400> SEQUENCE: 2

```
ccattctctg ctgctttgtt gcatcgtatc atcgcccgtt tcagccagtc ccgcataccc     60
cctttgcaac gttaacgtta ccgctagcgt ttaccatctc cacgctaaaa ggaaaacgaa    120
gattaagata aagttgggta aaatccgggg taagaggcaa gggggtagag aaaaaaaaac    180
cggagtcatt atatacgata ccgtccaggg taagacagtg atttctagct tccactttt    240
tcaatttctt ttttttcgttc caaatggcgt ccacccgtac atccggaatc tgacggcaca   300
agagccgatt agtgaaagcc agggttacgt gattgcggtt ttttttttcct acgtataacg   360
ctatgacggt agttgaatgt taaaaacgaa aacagagata ttgaattgac tcgtaggaac   420
aatttcgggc cctgcgtgt tcttctgagg ttcatctttt acatttgctt ctgctggata    480
```

```
attttcagag gcaacaagga aaaattagat ggcaaaaagt cgtctttcaa ggaaaaatcc      540
ccaccatctt tcgagatccc ctgtaactta ttggcaactg aaagaatgaa aaggaggaaa      600
atacaaaata tactagaact gaaaaaaaaa agtataaata gagacgatat atgccaatac      660
ttcacaatgt tcgaatccat tcttcatttg cagctattgt aaaataataa acatcaaga       720 acaaacaagc tcaacttgtc ttttctaaga acaaagaata aacacaaaaa caaaaagttt      780
ttttaatttt aatcaaaaa                                                   799

<210> SEQ ID NO 3
<211> LENGTH: 798
<212> TYPE: DNA
<213> ORGANISM: Saccharomyces cerevisiae

<400> SEQUENCE: 3
ccattctctg ctgctttgtt gcatcgtatc atcgcccgtt tcagccagtc ccgcataccc       60
cctttgcaac gttaacgtta ccgctagcgt ttaccatctc cacgctaaaa ggaaaacgaa      120
gattaagata aagttgggta aaatccgggg taagaggcaa gggggtagag aaaaaaaaac      180
cggagtcatt atatacgata ccgtccaggg taagacagtg atttctagct tccactttttt     240 tcaatttctt ttttttcgttc caaatggcgt ccacccgtac atccggaatc tgacggcaca     300
agagccgatt agtggaagcc acggttacgt gattgcggtt ttttttttcct acgtataacg     360 ctatgacggt agttgaatgt taaaaacgaa aacagagata ttgaattgac tcgtaggaac     420
aatttcgggc cctgcgtgt tcttctgagg ttcatctttt acatttgctt ctgctggata      480
attttcagag gcaacaagga aaaattagat ggcaaaaagt cgtctttcaa ggaaaaatcc      540
ccaccatcct tcgagatccc ctgtaactta ttggcaactg aaagaatgaa aaggaggaaa      600
atacaaaata tactagaact gaaaaaaaaa gtataaatag agacgatata tgccaataat      660
tcacaatgtt cgaatccatt cttcatttgc agctattgta aaataataaa acatcaagaa      720
caaacaagct caacttgtct tttctaagaa caaagaataa acacaaaaac aaaaagtttt      780
tttaatttta atcaaaaa                                                    798

<210> SEQ ID NO 4
<211> LENGTH: 800
<212> TYPE: DNA
<213> ORGANISM: Saccharomyces cerevisiae

<400> SEQUENCE: 4
ccattctctg ctgctttgtt gcatcgtatc atcgcccgtt tcagccagtc ccgcataccc       60
cctttgcaac gttaacgtta ccgctagcgt ttaccatctc cacgctaaaa ggaaaacgaa      120
gattaagata aagttgggta aaatccgggg taagaggcaa gggggtagag aaaaaaaaac      180
cggagtcatt atatacgata ccgtccaggg taagacagtg atttctagct tccactttttt     240 tcaatttctt ttttcgttc caaatggcgt ccacccgtac atccggaatc tgacggcaca      300
agagccgatt agtggaagcc acggttacgt gattgcggtt ttttttcct acgtataacg      360 ctatgacggt agttgaatgt taaaaacgaa aacagagata ttgaattgac tcgtaggaac     420
aatttcgggc cctgcgtgt tcttctgagg ttcatctttt acatttgctt ctgctggata      480
attttcagag gcaaaaagga aaaattagat ggcaaaaagt cgtctttcaa ggaaaaatcc     540
ccaccatctt tcgagatccc ctgtaactta ttggcaactg aaagaatgaa aaggaggaaa      600
atacaaaata tactagaact gaaaaaaaaa agtataaat agagacgata tatgccaata      660
cttcacaatg ttcaaatcca ttcttcgttt gcagctattg taaaataata aacatcaag      720
```

| | | |
|---|---|---|
| aacaaacaag ctcaacttgt cttttctaag aacaaagaat aaacacaaaa acaaaaagtt | 780 | |
| tttttaattt taatcaaaaa | 800 | |

<210> SEQ ID NO 5
<211> LENGTH: 799
<212> TYPE: DNA
<213> ORGANISM: Saccharomyces cerevisiae

<400> SEQUENCE: 5

| | |
|---|---|
| ccattctctg ctgctttgtt gcatcgtatc atcgcccgtt tcagccagtc ccgcataccc | 60 |
| cctttgcaac gttaacgtta ccgctagcgt ttaccatctc cacgctaaaa ggaaaacgaa | 120 |
| gattaagata aagttgggta aaatccgggg taagaggcaa gggggtagag aaaaaaaacc | 180 |
| ggagtcatta tatacgatac cgtccagggt aagacagtga tttctagctt ccactttttt | 240 |
| caatttcttt ttttcgttcc aaatggcgtc caccccgtaca tccggaatct gacggcacaa | 300 |
| gagccgatta gtggaagcca gggttacgtg attgcggttt ttttttccta cgtataacgc | 360 |
| tatgacggta gttgaatgtt aaaaacgaaa acagagatat tgaattgact cgtaggaaca | 420 |
| atttcgggtt cctgcgtgtt cttctgaggt tcatctttta catttgcttc tgctggataa | 480 |
| ttttcagagg caaaaggaa aaattagatg gcaaaaagtc gtctttcaag gaaaaatccc | 540 |
| caccatcttt cgagatcccc tgtaacttat tggcaactga agaatgaaa aggaggaaaa | 600 |
| tacaaaatat actagaactg aaaaaaaaaa agtataaata gagacgatat atgccaatac | 660 |
| ttcacaatgt tcgaatctat tcttcatttg cagctattgt aaaataataa acatcaaga | 720 |
| acaaacaagc tcaacttgtc ttttctaaga acaaagaata aacacaaaaa caaaaagttt | 780 |
| tttaatttt aatcaaaaa | 799 |

<210> SEQ ID NO 6
<211> LENGTH: 799
<212> TYPE: DNA
<213> ORGANISM: Saccharomyces cerevisiae

<400> SEQUENCE: 6

| | |
|---|---|
| ccattctctg ctgctttgtt gcatcgtatc atcgcccgtt tcagccagtc ccgcataccc | 60 |
| cctttgcaac gttaacgtta ccgctagcgt ttaccatctc cacgctaaaa ggaaaacgaa | 120 |
| gattaagata aagttgggta aaatccgggg taagaggcaa gggggtagag aaaaaaaaac | 180 |
| aggagtcatt atatacgata ccgttcaggg taagacagtg atttctagct tccactttt | 240 |
| tcaatttctt ttttcgttc caatggcgt ccacccgtac atccggaatc tgacggcaca | 300 |
| agagccgatt agtggaagcc agggttacgt gattgcggtt tttttttcct acgtataacg | 360 |
| ctatgacggt agttgaatgt taaaaacgaa aacagagata ttgaattgac tcgtaggaac | 420 |
| aatttcgggc cctgcgtgt tcttctgagg ttcatctttt acatttgctt ctgctggata | 480 |
| attttcagag gcaacaagga aaaattagat ggcaaaaagt cgtctttcaa ggaaaaatcc | 540 |
| ccaccatcct tcgagatccc ctgtaactta ttggcaactg aaagaatgaa aaggaggaaa | 600 |
| atacaaaata tactagaact gaaaaaaaaa agtataaata gagacgatat atgccaatac | 660 |
| ttcacaatgt tcgaatccat tcttcatttg cagctattgt aaaataataa acatcaaga | 720 |
| acaaacaagc tcaacttgtc ttttctaaga acaaagaata aacacaaaaa caaaaagttt | 780 |
| tttaatttt aatcaaaaa | 799 |

<210> SEQ ID NO 7

```
<211> LENGTH: 799
<212> TYPE: DNA
<213> ORGANISM: Saccharomyces cerevisiae

<400> SEQUENCE: 7
ccattctctg ctgctttgtt gcatcgtatc atcgcccgtt tcagccagtc ccgcataccc    60
cctttgcaac gttaacgtta ccgctagcgt ttaccatctc cacgctaaaa ggaaaacgaa   120
gattaagata aagttgggta aaatccgggg taagaggcaa gggggtagag aaaaaaaaac   180
cggagacatt atatacgata ccgtccaggg taagacagtg atttctagct tccactttt    240
tcaatttctt tttttcgttc caaatggcgt ccacccgtac atccggaatc tgacggcaca   300
agagccgatt agtggaagcc agggttacgt gattgcggtt ttttttttcct acgtataacg   360
ctatgacggt agttgaatgt taaaaacgaa aacagagata ttgaattgac tcgtaggaac   420
aatttcgggt tcctgcgtgt tcttctgagg ttcatctttt acatttgctt ctgctggata   480
attttcagag gcaacaagga aaaattagat ggcaaaaagt cgtctttcaa ggaaaaatcc   540
ccaccatctt tcgagatccc ctgtaactta ttggcaactg aaagaatgaa aaggaggaaa   600
atacaaaata tactagaact gaaaaaaaaa agtataaata gagacgatat atgccaatac   660
ttcacaatgt tcgaatccat tcttcatttg cagctattgt aaaataataa acatcaaga    720
acaaacaagc tcaacttgtc ttttctaaga acaagaata aacacaaaaa caaaaagttt    780
ttttaatttt aatcaaaaa                                                799

<210> SEQ ID NO 8
<211> LENGTH: 409
<212> TYPE: DNA
<213> ORGANISM: Saccharomyces cerevisiae

<400> SEQUENCE: 8
ccattctctg ctgctttgtt gcatcgtatc atcgcccgtt tcagccagtc ccgcataccc    60
cctttgcaac gttaacgtta ccgctagcgt ttaccatctc cacgctaaaa ggaaaacgaa   120
gattaagata aagttgggta aaatccgggg taagaggcaa gggggtagag aaaaaaaaac   180
cggagtcatt atatacgata ccgtccaggg taagacagtg atttctagct tccactttt    240
tcaatttctt tttttcgttc caaatggcgt ccacccgtac atccggaatc tgacggcaca   300
agagccgatt agtggaagcc acggttacgt gattgcggtt ttttttttcct acgtataacg   360
ctatgacggt agttgaatgt taaaaacgaa aacagagata ttgaattga                409

<210> SEQ ID NO 9
<211> LENGTH: 391
<212> TYPE: DNA
<213> ORGANISM: Saccharomyces cerevisiae

<400> SEQUENCE: 9
ctcgtaggaa caatttcggg cccctgcgtg ttcttctgag gttcatcttt tacatttgct    60
tctgctggat aattttcaga ggcaacaagg aaaaattaga tggcaaaaag tcgtctttca   120
aggaaaaatc cccaccatct ttcgagatcc cctgtaactt attggcaact gaaagaatga   180
aaaggaggaa aatacaaaat atactagaac tgaaaaaaaa aagtataaa tagagacgat    240
atatgccaat acttcacaat gttcgaatct attcttcatt tgcagctatt gtaaaataat   300
aaacatcaa gaacaaacaa gctcaacttg tcttttctaa gaacaaagaa taaacacaaa   360
aacaaaaagt ttttttaatt ttaatcaaaa a                                  391
```

<210> SEQ ID NO 10
<211> LENGTH: 500
<212> TYPE: DNA
<213> ORGANISM: Saccharomyces cerevisiae

<400> SEQUENCE: 10

```
tgtttgcaaa aagaacaaaa ctgaaaaaac ccagacacgc tcgacttcct gtcttcctat      60
tgattgcagc ttccaatttc gtcacacaac aaggtcctag cgacggctca caggttttgt     120
aacaagcaat cgaaggttct ggaatggcgg gaaaggtttt agtaccacat gctatgatgc     180
ccactgtgat ctccagagca agttcgttc gatcgtactg ttactctctc tctttcaaac      240
agaattgtcc gaatcgtgtg acaacaacag cctgttctca cacactcttt tcttctaacc     300
aagggggtgg tttagtttag tagaacctcg tgaaacttac atttacatat atataaactt     360
gcataaattg gtcaatgcaa gaaatacata tttggtcttt tctaattcgt agttttcaa      420
gttcttagat gctttctttt tctctttttt acagatcatc aaggaagtaa ttatctactt     480
tttacaacaa agacaagaaa                                                 500
```

<210> SEQ ID NO 11
<211> LENGTH: 342
<212> TYPE: PRT
<213> ORGANISM: Saccharomyces cerevisiae

<400> SEQUENCE: 11

```
Met Lys Asp Asn Gln Glu Asn His Asp Gln Lys Pro Phe Ile Ile Leu
1               5                   10                  15

Gly Asp Lys Asn Lys Phe Glu Ala Thr Ile Ala Lys Val Gly Ala Thr
            20                  25                  30

Leu Val Asp Leu Lys Val Asn Gly Gln Ser Val Val Leu Gly Tyr Pro
        35                  40                  45

Asp Val Lys Gly Tyr Leu Asn Asp Pro Gly Asn Leu Val Gly Ala Asn
    50                  55                  60

Val Gly Arg Tyr Ala Asn Arg Ile Tyr Lys Gly Val Phe Asn Thr Pro
65                  70                  75                  80

Asp Gly Ala His Gln Leu Thr Val Asn Asn Cys Gly Asn Ala Asn His
                85                  90                  95

Ser Ser Ile Ser Cys Phe Asn Arg Lys Thr Phe Val Ala Ser Pro Val
            100                 105                 110

Glu Asn Ser Ser Arg Asp Val Tyr Ile Ala Lys Leu Thr Leu Leu Asp
        115                 120                 125

Asp His Thr Val Pro Asn Glu Phe Pro Gly Asp Leu Glu Val Thr Val
    130                 135                 140

Thr Tyr Thr Leu Asn Val Ala Glu Met Thr Leu Asp Leu Asp Tyr Arg
145                 150                 155                 160

Ala His Leu Val Lys Gly Asp Ala Thr Pro Ile Asn Met Thr Asn His
                165                 170                 175

Thr Tyr Phe Asn Leu Asn Lys Thr Arg Asn Glu Glu Ser Ile Ile Gly
            180                 185                 190

Thr Glu Ile Asn Ile Cys Ser Asp Lys Ser Leu Glu Val Thr Glu Gly
        195                 200                 205

Ala Leu Ile Pro Thr Gly Lys Ile Ile Lys Arg Asp Ile Ala Thr Phe
    210                 215                 220

Gln Ser Ala His Pro Thr Thr Leu Gly Ser Lys Ala Pro Val Tyr Asp
225                 230                 235                 240

Phe Cys Phe Ile Val Asp Ala Asn Lys Asp Leu Arg Ser Thr Asp Ser
```

Thr Ser Val Asn Lys Leu Val Pro Val Phe Lys Ala Tyr His Pro Glu
            245                 250                 255
                260                 265                 270

Ser Asn Ile Arg Leu Gln Val Ser Thr Thr Glu Pro Thr Val His Phe
                275                 280                 285

Tyr Thr Gly Asp Ser Leu Gly Gly Lys Phe Val Pro Arg Ser Gly Phe
        290                 295                 300

Ala Val Glu Gln Gly Arg Tyr Ile Asp Ala Ile Asn Arg Ser Glu Trp
305                 310                 315                 320

Arg Asn Cys Val Leu Leu Lys Arg Gly Glu Val Tyr Thr Ser Lys Thr
                325                 330                 335

Gln Tyr Cys Phe Lys Asn
                340

<210> SEQ ID NO 12
<211> LENGTH: 359
<212> TYPE: PRT
<213> ORGANISM: Saccharomyces cerevisiae

<400> SEQUENCE: 12

Met Gly Ser Lys Asn Thr Leu Leu Val Phe His Leu Lys Gly Val Lys
1               5                   10                  15

Thr Asp Leu Ala Gly Ala Val Asn Asp Tyr Glu Asn Arg Phe Ile Thr
                20                  25                  30

Ile Gly Ala Gly Ser Lys Phe Glu Ala Thr Ile Ala Asn Leu Gly Ala
            35                  40                  45

Thr Leu Val Asp Leu Lys Val Asn Gly Gln Ser Val Val Leu Gly Tyr
        50                  55                  60

Ser Arg Ala Glu Asp Tyr Asn Ser Asp Gly Gly Asn Tyr Ile Gly Ala
65                  70                  75                  80

Thr Val Gly Arg Phe Ala Asn Arg Ile Lys Glu Gly Leu Phe Thr Leu
                85                  90                  95

Gln Asp Gly Thr His Lys Leu Thr Val Asp Asn Cys Asp Asn Thr Asn
                100                 105                 110

His Ser Ser Ile Ser Ser Phe His Val Lys Lys Phe Leu Gly Pro Leu
            115                 120                 125

Ile Glu Asn Pro Ser Asp Glu Ile Tyr Thr Ala Glu Phe Leu Leu Leu
        130                 135                 140

Asp Asp His Ser Ile Pro Asn Glu Phe Pro Gly Asp Leu Glu Val Ile
145                 150                 155                 160

Val Lys Phe Thr Leu Asn Ile Ala Glu Met Ser Leu Lys Phe Ser Tyr
                165                 170                 175

Gln Ala Gln Leu Ile Asn Gly Glu Ala Thr Pro Ile Asn Met Thr Ser
            180                 185                 190

His Thr Tyr Phe Asn Leu Asn Lys Phe His Asn Glu Gln Ser Ile Ser
        195                 200                 205

Gly Thr Glu Val Arg Val Cys Ser Thr Lys Ser Leu Glu Val Ser Glu
        210                 215                 220

Gly Ala Leu Ile Pro Thr Gly Lys Val Ile Asp Arg Asp Val Ala Thr
225                 230                 235                 240

Phe Asp Ser Ala Gly Pro Thr Thr Leu Gly Gly Asp Gly Pro Thr Tyr
                245                 250                 255

Asp Tyr Cys Phe Ile Ser Asp Glu Asn Lys Gly Leu Lys Ser Pro Asp
                260                 265                 270

```
Ser Arg Ser Gln Asn Glu Leu Arg Pro Val Leu Lys Ala Tyr His Pro
            275                 280                 285

Glu Ser Lys Ile Thr Leu Glu Val Ser Thr Thr Glu Pro Ser Phe Val
        290                 295                 300

Leu Tyr Ser Gly Asp Asn Leu Phe Gly Lys Phe Ile Pro Arg Gln Gly
305                 310                 315                 320

Phe Cys Val Glu Gln Gly Arg Tyr Ile Asp Ala Ile Asn Arg Asp Asp
                325                 330                 335

Trp Lys Asp Cys Val Leu Leu Lys Arg Gly Asp Val Tyr Thr Ser Glu
            340                 345                 350

Thr Gln Tyr Arg Phe Glu Asn
        355

<210> SEQ ID NO 13
<211> LENGTH: 341
<212> TYPE: PRT
<213> ORGANISM: Saccharomyces cerevisiae

<400> SEQUENCE: 13

Met Ser Asn Asn Lys Ala Gly Gly Glu Tyr Glu Val Ile Thr Ile Gly
1               5                   10                  15

Asp Ala Lys Lys Leu Gln Ala Thr Ile Ser Glu Leu Gly Ala Thr Leu
            20                  25                  30

Leu Asp Leu Lys Val Asn Asn Glu Ser Ile Val Leu Gly Tyr Pro Asp
        35                  40                  45

Ile His Gly Tyr Ile Ser Asp Gly Tyr Asn Tyr Ile Gly Ala Thr Val
    50                  55                  60

Gly Arg Tyr Ala Asn Arg Ile Tyr Lys Gly Met Phe Ser Met Glu Asp
65                  70                  75                  80

Gly Pro His Gln Leu Thr Val Asn Asn Cys Gly Asn Thr Asn His Ser
                85                  90                  95

Ser Ile Ser Ser Phe His Leu Lys Lys Tyr Lys Ala Ser Lys Val Gln
            100                 105                 110

Asn Pro Leu Asp Asp Leu Tyr Ile Val Glu Phe Thr Leu Leu Asp Asp
        115                 120                 125

Arg Thr Leu Pro Asn Glu Phe Pro Gly Asp Leu Ala Val Asn Leu Lys
130                 135                 140

Tyr Thr Leu Asn Val Ala Asp Met Thr Leu Asp Leu Glu Tyr Glu Ala
145                 150                 155                 160

Lys Leu Val Ser Gly Glu Ala Thr Pro Ile Asn Met Thr Asn His Thr
                165                 170                 175

Tyr Phe Asn Leu Asn Lys Thr Met Asp Lys Lys Ser Ile Ser Gly Thr
            180                 185                 190

Glu Val Arg Leu Cys Ser Asp Lys Ser Leu Glu Val Ser Glu Gly Ala
        195                 200                 205

Leu Ile Pro Thr Gly Lys Ile Val Gln Arg Lys Ile Ala Thr Phe Asp
    210                 215                 220

Ser Ser Lys Pro Thr Ile Leu Gln Asp Asp Gly Pro Ile Tyr Asp Tyr
225                 230                 235                 240

Ala Phe Ile Val Asp Glu Asn Lys Asn Leu Lys Thr Thr Asp Ser Val
                245                 250                 255

Ser Val Asn Lys Leu Val Pro Ala Phe Lys Ala Tyr His Pro Ala Ser
            260                 265                 270

Arg Leu Ser Leu Glu Val Ser Thr Thr Glu Pro Thr Val Leu Phe Tyr
        275                 280                 285
```

```
Thr Gly Asp Asn Leu Cys Asp Gly Phe Thr Pro Arg Ser Gly Phe Ala
        290                 295                 300

Val Glu Gln Gly Arg Tyr Val Asp Ala Ile Asn Arg Asp Gly Trp Arg
305                 310                 315                 320

Asp Cys Val Leu Leu Arg Arg Gly Glu Val Tyr Thr Ser Lys Thr Arg
                325                 330                 335

Tyr Arg Phe Ala Val
            340

<210> SEQ ID NO 14
<211> LENGTH: 360
<212> TYPE: PRT
<213> ORGANISM: Saccharomyces cerevisiae

<400> SEQUENCE: 14

Met Ser Asn Asp Gly Gln Gln Lys Lys Leu Ala Thr Ile Asp Asn Lys
1               5                   10                  15

Leu Glu Met Thr Asn Ser Asn Thr Glu Asn Lys Tyr Lys Val Ile Thr
            20                  25                  30

Ile Gly Asp Glu Lys Arg Phe Gln Ala Thr Ile Ala Pro Leu Gly Ala
        35                  40                  45

Thr Leu Val Asp Leu Lys Val Asn Asn Gln Ser Val Gln Gly Tyr
    50                  55                  60

Ser Asn Val Gln Asp Tyr Leu Thr Asp Gly Asn Met Met Gly Ala Thr
65                  70                  75                  80

Val Gly Arg Tyr Ala Asn Arg Ile Ala Lys Gly Val Phe Ser Leu Glu
                85                  90                  95

Asp Gly Pro His Lys Leu Thr Val Asn Asn Cys Gly Asn Thr Asn His
            100                 105                 110

Ser Ser Ile Ser Ser Leu Asn Leu Lys Gln Tyr Arg Ala Ser Pro Val
        115                 120                 125

Glu Asn Pro Ser Lys Asp Val Phe Val Val Glu Phe Lys Leu Leu Asp
    130                 135                 140

Asp His Thr Gln Pro Asn Pro Asn Glu Phe Pro Gly Asp Leu Glu Val
145                 150                 155                 160

Thr Val Lys Tyr Thr Leu Asn Val Ala Glu Met Thr Leu Gly Met Lys
                165                 170                 175

Tyr Gln Ala Gln Leu Val Arg Gly Asp Ala Thr Pro Ile Asn Met Thr
            180                 185                 190

Asn His Ser Tyr Phe Asn Leu Asn Lys Thr Lys Asn Glu Lys Ser Ile
        195                 200                 205

Ser Gly Thr Glu Val Lys Val Cys Ser Asn Lys Ser Leu Glu Val Thr
    210                 215                 220

Glu Gly Ala Leu Leu Pro Thr Glu Lys Ile Ile Glu Arg Lys Ile Ala
225                 230                 235                 240

Thr Phe Asp Ser Ala Lys Pro Thr Val Leu His Asp Asp Ala Pro Val
                245                 250                 255

Phe Asp Cys Thr Phe Ile Ile Asp Ala Asn Lys Asp Leu His Thr Thr
            260                 265                 270

Asp Ser Val Ser Val Asn Lys Leu Val Pro Val Phe Lys Ala Tyr His
        275                 280                 285

Pro Glu Ser Arg Ile Thr Phe Glu Val Ser Thr Glu Pro Thr Val
    290                 295                 300

His Leu Tyr Thr Gly Asp Asn Leu Cys Gly Lys Phe Thr Pro Arg Ser
```

```
                305                 310                 315                 320
Gly Phe Ala Val Gln Gln Gly Arg Tyr Val Asp Ala Ile Asn His Asp
                    325                 330                 335

Lys Trp Arg Asp Cys Val Leu Leu Lys Arg Gly Glu Val Tyr Thr Ser
                340                 345                 350

Glu Thr Gln Tyr Arg Phe Gly Ile
            355                 360

<210> SEQ ID NO 15
<211> LENGTH: 342
<212> TYPE: PRT
<213> ORGANISM: Saccharomyces cerevisiae

<400> SEQUENCE: 15

Met Ser Asn Ser Asn Gly Asp Asn Lys Tyr Gly Val Ile Thr Ile Gly
1               5                   10                  15

Asp Glu Lys Lys Phe Gln Ala Thr Ile Ala Pro Leu Gly Ala Thr Leu
                20                  25                  30

Val Asp Leu Lys Val Asn Gly Gln Ser Val Val Gln Gly Tyr Ser Asn
            35                  40                  45

Val Gln Asp Tyr Leu Thr Asp Gly Asn Met Met Gly Ala Thr Val Gly
        50                  55                  60

Arg Tyr Ala Asn Arg Ile Ala Lys Gly Val Phe Ser Leu Asp Asp Gly
65                  70                  75                  80

Pro His Lys Leu Thr Val Asn Asn Cys Gly Asn Thr Asn His Ser Ser
                85                  90                  95

Ile Ser Ser Leu Asn Leu Lys Gln Tyr Lys Ala Ser Pro Val Glu Asn
                100                 105                 110

Pro Ser Lys Gly Val Tyr Val Val Glu Phe Lys Leu Leu Asp Asp His
            115                 120                 125

Thr Gln Pro Asn Pro Asn Glu Phe Pro Gly Asp Leu Glu Val Thr Val
        130                 135                 140

Lys Tyr Thr Leu Asn Val Ala Glu Met Thr Leu Asp Met Glu Tyr Gln
145                 150                 155                 160

Ala Gln Leu Val Arg Gly Asp Ala Thr Pro Ile Asn Met Thr Asn His
                165                 170                 175

Ser Tyr Phe Asn Leu Asn Lys Val Lys Ser Glu Lys Ser Ile Arg Gly
                180                 185                 190

Thr Glu Val Lys Val Cys Ser Asn Lys Ser Leu Glu Val Thr Glu Gly
            195                 200                 205

Ala Leu Leu Pro Thr Gly Lys Ile Ile Glu Arg Asn Ile Ala Thr Phe
        210                 215                 220

Asp Ser Thr Lys Pro Thr Val Leu His Glu Asp Thr Pro Val Phe Asp
225                 230                 235                 240

Cys Thr Phe Ile Ile Asp Ala Asn Lys Asp Leu Lys Thr Thr Asp Ser
                245                 250                 255

Val Ser Val Asn Lys Leu Val Pro Val Phe Lys Ala Tyr His Pro Glu
                260                 265                 270

Ser His Ile Lys Phe Glu Val Ser Thr Thr Glu Pro Thr Val His Leu
            275                 280                 285

Tyr Thr Gly Asp Asn Leu Cys Gly Lys Phe Val Pro Arg Ser Gly Phe
        290                 295                 300

Ala Val Gln Gln Gly Arg Tyr Val Asp Ala Ile Asn Arg Asp Glu Trp
305                 310                 315                 320
```

Arg Gly Cys Val Leu Leu Lys Arg Gly Glu Val Tyr Thr Ser Lys Thr
            325                 330                 335

Gln Tyr Lys Phe Asp Ile
            340

<210> SEQ ID NO 16
<211> LENGTH: 334
<212> TYPE: PRT
<213> ORGANISM: Lactococcus lactis

<400> SEQUENCE: 16

Met Thr Phe Thr Ile Ser Lys Glu Ser Leu Pro Phe Arg Ala Asp Lys
1               5                   10                  15

Ser Ile Ser Gln Ile Thr Leu Ser Asn Glu Arg Leu Thr Ile Val Val
            20                  25                  30

His Asp Tyr Gly Ala Arg Ala His Gln Leu Leu Thr Pro Asp Lys Asn
        35                  40                  45

Gly Thr Phe Glu Asn Ile Leu Leu Ser Lys Asn Asp Ser Glu Thr Tyr
    50                  55                  60

Ala Asn Asp Gly Gly Tyr Tyr Gly Val Ile Cys Gly Pro Val Ala Gly
65                  70                  75                  80

Arg Ile Ser Gly Ala Thr Tyr Asp Ser Val Ser Leu Glu Ala Asn Glu
                85                  90                  95

Gly Lys Asn Asn Leu His Ser Gly Ser His Gly Trp Glu Arg Gln Phe
            100                 105                 110

Trp Ser Tyr Glu Thr Phe Glu Thr Ala Ser Ser Leu Gly Ile Lys Leu
        115                 120                 125

Ser Leu Arg Asp Glu Glu Ser Gly Phe Pro Gly Gln Ile Gln Ala Glu
    130                 135                 140

Val Thr Tyr Lys Leu Thr Asp Asn Lys Leu Glu Val Thr Ile Ser Gly
145                 150                 155                 160

Leu Ser Val Thr Asp Thr Val Phe Asn Pro Ala Trp His Pro Tyr Phe
                165                 170                 175

Asn Leu Ser Ala Glu Leu Ser Thr Thr His Glu His Phe Ile Gln Ala
            180                 185                 190

Asn Val Asp Phe Leu Val Glu Thr Asn Gln Glu Asn Ile Pro Thr Gly
        195                 200                 205

Arg Leu Leu Thr Val Asp Asp Ser Ser Tyr Ser Ile Lys Glu Ser Val
    210                 215                 220

Ser Ile Lys Lys Leu Leu Lys Asp Asn Pro Glu Gly Leu Asp Asp Cys
225                 230                 235                 240

Phe Val Phe Asn Pro Lys Gly Asp Lys Ser Leu Met Leu Tyr Asp Pro
                245                 250                 255

Leu Ser Gly Arg Lys Leu Val Ala Gln Thr Asp Arg Gln Ala Val Val
            260                 265                 270

Ile Tyr Thr Ala Thr Asn Pro Glu Ile Glu Ser Met Ile Asn Gly Arg
        275                 280                 285

Pro Met Ser Lys Asn Arg Gly Ile Ala Ile Glu Phe Gln Glu Ile Pro
    290                 295                 300

Asp Leu Val His His Pro Glu Trp Gly Thr Ile Glu Leu Lys Ala Gly
305                 310                 315                 320

Gln Lys Lys Thr Phe Ile Thr Glu Tyr Leu Phe Thr Thr Asn
                325                 330

<210> SEQ ID NO 17

<211> LENGTH: 442
<212> TYPE: PRT
<213> ORGANISM: Eubacterium saburreum

<400> SEQUENCE: 17

Met Lys Glu Phe Phe Pro Gly Ile Ser Pro Val Lys Phe Glu Gly Arg
1               5                   10                  15

Asp Ser Lys Asn Pro Leu Ser Phe Lys Tyr Tyr Asp Ala Lys Arg Val
            20                  25                  30

Ile Met Gly Lys Thr Met Glu His Leu Ser Phe Ala Met Ala Trp
        35                  40                  45

Trp His Asn Leu Cys Ala Cys Gly Val Asp Met Phe Gly Gln Gly Thr
    50                  55                  60

Val Asp Lys Ser Phe Gly Glu Ser Ser Gly Thr Met Glu His Ala Arg
65                  70                  75                  80

Ala Lys Val Asp Ala Gly Ile Glu Phe Met Lys Lys Leu Gly Ile Lys
                85                  90                  95

Tyr Tyr Cys Phe His Asp Thr Asp Ile Val Pro Glu Asp Gln Glu Asp
            100                 105                 110

Ile Asn Val Thr Asn Ala Arg Leu Asp Glu Ile Thr Asp Tyr Ile Leu
        115                 120                 125

Glu Lys Thr Lys Asp Thr Asp Ile Lys Cys Leu Trp Thr Thr Cys Asn
130                 135                 140

Met Phe Ser Asn Pro Arg Phe Met Asn Gly Ala Gly Ser Ser Asn Ser
145                 150                 155                 160

Ala Asp Val Phe Cys Phe Ala Ala Gln Ala Lys Lys Gly Leu Glu
                165                 170                 175

Asn Ala Val Lys Leu Gly Ala Lys Gly Phe Val Phe Trp Gly Gly Arg
            180                 185                 190

Glu Gly Tyr Glu Thr Leu Leu Asn Thr Asp Met Lys Leu Glu Glu Glu
        195                 200                 205

Asn Ile Ala Thr Leu Phe Thr Met Cys Arg Asp Tyr Gly Arg Ser Ile
    210                 215                 220

Gly Phe Met Gly Asp Phe Tyr Ile Glu Pro Lys Pro Lys Glu Pro Met
225                 230                 235                 240

Lys His Gln Tyr Asp Phe Asp Ala Ala Thr Ala Ile Gly Phe Leu Arg
                245                 250                 255

Lys Tyr Gly Leu Asp Lys Asp Phe Lys Leu Asn Ile Glu Ala Asn His
            260                 265                 270

Ala Thr Leu Ala Gly His Thr Phe Gln His Glu Leu Arg Val Cys Ala
        275                 280                 285

Val Asn Gly Met Met Gly Ser Val Asp Ala Asn Gln Gly Asp Thr Leu
    290                 295                 300

Leu Gly Trp Asp Thr Asp Gln Phe Pro Thr Asn Val Tyr Asp Thr Thr
305                 310                 315                 320

Leu Ala Met Tyr Glu Ile Leu Lys Ala Gly Gly Leu Arg Gly Gly Leu
                325                 330                 335

Asn Phe Asp Ser Lys Asn Arg Arg Pro Ser Asn Thr Ala Asp Asp Met
            340                 345                 350

Phe Tyr Gly Phe Ile Ala Gly Met Asp Thr Phe Ala Leu Gly Leu Ile
        355                 360                 365

Lys Ala Ala Glu Ile Ile Glu Asp Gly Arg Ile Asp Asp Phe Val Lys
    370                 375                 380

Glu Arg Tyr Ala Ser Tyr Asn Ser Gly Ile Gly Lys Lys Ile Arg Asn

-continued

```
             385                 390                 395                 400
Arg Lys Val Thr Leu Ile Glu Cys Ala Glu Tyr Ala Ala Lys Leu Lys
                     405                 410                 415

Lys Pro Glu Leu Pro Glu Ser Gly Arg Gln Glu Tyr Leu Glu Ser Val
                 420                 425                 430

Val Asn Asn Ile Leu Phe Gly Gly Ser Gly
             435                 440

<210> SEQ ID NO 18
<211> LENGTH: 437
<212> TYPE: PRT
<213> ORGANISM: Piromyces sp. E2

<400> SEQUENCE: 18

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320
```

```
Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
            405                 410                 415

Gly Glu Pro Lys Gln Thr Ser Gly Lys Gln Glu Leu Tyr Glu Ala Ile
        420                 425                 430

Val Ala Met Tyr Gln
            435

<210> SEQ ID NO 19
<211> LENGTH: 437
<212> TYPE: PRT
<213> ORGANISM: Orpinomyces sp. PC-2

<400> SEQUENCE: 19

Met Thr Lys Glu Tyr Phe Pro Thr Ile Gly Lys Ile Arg Phe Glu Gly
1               5                   10                  15

Lys Asp Ser Lys Asn Pro Met Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Asp Gly Ala Asp Gln Phe Gly Val Gly
    50                  55                  60

Thr Lys Ser Phe Pro Trp Asn Glu Gly Thr Asp Pro Ile Ala Ile Ala
65                  70                  75                  80

Lys Gln Lys Val Asp Ala Gly Phe Glu Ile Met Thr Lys Leu Gly Ile
                85                  90                  95

Glu His Tyr Cys Phe His Asp Val Asp Leu Val Ser Glu Gly Asn Ser
            100                 105                 110

Ile Glu Glu Tyr Glu Ser Asn Leu Lys Gln Val Ala Tyr Leu Lys
        115                 120                 125

Gln Lys Gln Gln Glu Thr Gly Ile Lys Leu Leu Trp Ser Thr Ala Asn
    130                 135                 140

Val Phe Gly Asn Pro Arg Tyr Met Asn Gly Ala Ser Thr Asn Pro Asp
145                 150                 155                 160

Phe Asp Val Val Ala Arg Ala Ile Val Gln Ile Lys Asn Ala Met Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255
```

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
            275                 280                 285

Asp Ala Gly Met Leu Gly Ser Ile Asp Ala Asn Arg Gly Asp Tyr Gln
            290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Ile Ser Gly Met Asp Ala Met Ala Arg Ala Leu
            355                 360                 365

Glu Asn Ala Ala Lys Leu Leu Gln Glu Ser Pro Tyr Cys Asn Met Lys
            370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
            405                 410                 415

Gly Glu Pro Lys Val Thr Ser Gly Lys Gln Glu Leu Tyr Glu Ala Ile
            420                 425                 430

Val Ala Met Tyr Gln
            435

<210> SEQ ID NO 20
<211> LENGTH: 438
<212> TYPE: PRT
<213> ORGANISM: Clostrium phytofermentans

<400> SEQUENCE: 20

Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Glu Arg Ile
            20                  25                  30

Val Ala Gly Lys Thr Met Lys Glu His Cys Arg Phe Ala Leu Ser Trp
            35                  40                  45

Trp His Thr Leu Cys Ala Gly Gly Ala Asp Pro Phe Gly Val Thr Thr
        50                  55                  60

Met Asp Arg Ser Tyr Gly Asn Ile Thr Asp Pro Met Glu Phe Ala Lys
65                  70                  75                  80

Ala Lys Val Asp Ala Gly Phe Glu Leu Met Thr Lys Leu Gly Ile Glu
                85                  90                  95

Tyr Phe Cys Phe His Asp Ala Asp Ile Ala Pro Glu Gly Glu Asn Phe
            100                 105                 110

Glu Glu Ser Lys Lys Asn Leu Phe Val Ile Val Asp Tyr Ile Lys Glu
            115                 120                 125

Lys Met Asp Gln Thr Gly Ile Lys Leu Leu Trp Gly Thr Ala Asn Asn
            130                 135                 140

Phe Gly His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu

```
            180                 185                 190
Gly Tyr Glu Thr Leu Leu Asn Thr Asp Leu Gly Leu Glu Leu Asp Asn
            195                 200                 205

Met Ala Arg Leu Met Lys Met Ala Val Glu Tyr Gly Arg Ala Asn Gly
            210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Gly Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Leu Ala Arg Val
            275                 280                 285

Asn Gly Val Phe Gly Ser Val Asp Ala Asn Gln Gly Asp Pro Asn Leu
            290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Thr Phe Ala Leu Gly Leu Ile
            355                 360                 365

Lys Ala Ala Glu Ile Ile Glu Asp Gly Arg Ile Ala Lys Phe Val Glu
            370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Asn
                405                 410                 415

Glu Pro Val Met Gln Ser Gly Arg Gln Glu Val Leu Glu Ser Ile Val
            420                 425                 430

Asn Asn Ile Leu Phe Arg
            435

<210> SEQ ID NO 21
<211> LENGTH: 438
<212> TYPE: PRT
<213> ORGANISM: Ruminococcus flavefaciens

<400> SEQUENCE: 21

Met Glu Phe Phe Ser Asn Ile Gly Lys Ile Gln Tyr Gln Gly Pro Lys
1               5                   10                  15

Ser Thr Asp Pro Leu Ser Phe Lys Tyr Tyr Asn Pro Glu Glu Val Ile
                20                  25                  30

Asn Gly Lys Thr Met Arg Glu His Leu Lys Phe Ala Leu Ser Trp Trp
            35                  40                  45

His Thr Met Gly Gly Asp Gly Thr Asp Met Phe Gly Cys Gly Thr Thr
            50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
                100                 105                 110
```

-continued

Thr Asn Asp Gln Leu Asp Ile Val Thr Asp Tyr Ile Lys Glu Lys Gln
            115                 120                 125

Gly Asp Lys Phe Lys Cys Leu Trp Gly Thr Ala Lys Cys Phe Asp His
130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
                165                 170                 175

Leu Gly Gly Asn Gly Tyr Val Phe Trp Gly Gly Arg Glu Gly Tyr Glu
            180                 185                 190

Thr Leu Leu Asn Thr Asn Met Gly Leu Glu Leu Asp Asn Met Ala Arg
        195                 200                 205

Leu Met Lys Met Ala Val Glu Tyr Gly Arg Ser Ile Gly Phe Lys Gly
    210                 215                 220

Asp Phe Tyr Ile Glu Pro Lys Pro Lys Glu Pro Thr Lys His Gln Tyr
225                 230                 235                 240

Asp Phe Asp Thr Ala Thr Val Leu Gly Phe Leu Arg Lys Tyr Gly Leu
                245                 250                 255

Asp Lys Asp Phe Lys Met Asn Ile Glu Ala Asn His Ala Thr Leu Ala
            260                 265                 270

Gln His Thr Phe Gln His Glu Leu Arg Val Ala Arg Asp Asn Gly Val
        275                 280                 285

Phe Gly Ser Ile Asp Ala Asn Gln Gly Asp Val Leu Leu Gly Trp Asp
    290                 295                 300

Thr Asp Gln Phe Pro Thr Asn Ile Tyr Asp Thr Thr Met Cys Met Tyr
305                 310                 315                 320

Glu Val Ile Lys Ala Gly Gly Phe Thr Asn Gly Gly Leu Asn Phe Asp
                325                 330                 335

Ala Lys Ala Arg Arg Gly Ser Phe Thr Pro Glu Asp Ile Phe Tyr Ser
            340                 345                 350

Tyr Ile Ala Gly Met Asp Ala Phe Ala Leu Gly Phe Arg Ala Ala Leu
        355                 360                 365

Lys Leu Ile Glu Asp Gly Arg Ile Asp Lys Phe Val Ala Asp Arg Tyr
    370                 375                 380

Ala Ser Trp Asn Thr Gly Ile Gly Ala Asp Ile Ile Ala Gly Lys Ala
385                 390                 395                 400

Asp Phe Ala Ser Leu Glu Lys Tyr Ala Leu Glu Lys Gly Glu Val Thr
                405                 410                 415

Ala Ser Leu Ser Ser Gly Arg Gln Glu Met Leu Glu Ser Ile Val Asn
            420                 425                 430

Asn Val Leu Phe Ser Leu
        435

<210> SEQ ID NO 22
<211> LENGTH: 438
<212> TYPE: PRT
<213> ORGANISM: Bacteroides uniformis

<400> SEQUENCE: 22

Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asp
            20                  25                  30

Lys Val Ile Met Gly Lys Lys Met Ser Glu Trp Leu Lys Phe Ala Met
        35                  40                  45

Ala Trp Trp His Thr Leu Cys Ala Glu Gly Gly Asp Gln Phe Gly Gly
         50                  55                  60

Gly Thr Lys Lys Phe Pro Trp Asn Gly Glu Ala Asp Lys Val Gln Ala
 65                  70                  75                  80

Ala Lys Asn Lys Met Asp Ala Gly Phe Glu Phe Met Gln Lys Met Gly
                 85                  90                  95

Ile Glu Tyr Tyr Cys Phe His Asp Val Asp Leu Cys Glu Glu Ala Glu
            100                 105                 110

Thr Ile Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Ile Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Gly Gly Phe Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
        355                 360                 365

Leu Glu Ser Ala Ala Lys Leu Leu Glu Glu Ser Pro Tyr Lys Lys Met
370                 375                 380

Leu Ala Asp Arg Tyr Ala Ser Phe Asp Ser Gly Lys Gly Lys Glu Phe
385                 390                 395                 400

Glu Asp Gly Lys Leu Thr Leu Glu Asp Leu Val Ala Tyr Ala Lys Ala
                405                 410                 415

Asn Gly Glu Pro Lys Gln Thr Ser Gly Lys Gln Glu Leu Tyr Glu Ala
            420                 425                 430

Ile Val Asn Met Tyr Cys
        435

<210> SEQ ID NO 23
<211> LENGTH: 439

<212> TYPE: PRT
<213> ORGANISM: Clostridium cellulolyticum

<400> SEQUENCE: 23

```
Met Ser Glu Val Phe Ser Gly Ile Ser Asn Ile Lys Phe Glu Gly Ser
1               5                   10                  15

Gly Ser Asp Asn Pro Leu Ala Phe Lys Tyr Tyr Asp Pro Lys Ala Val
                20                  25                  30

Ile Gly Gly Lys Thr Met Glu Glu His Leu Arg Phe Ala Val Ala Tyr
            35                  40                  45

Trp His Thr Phe Ala Ala Pro Gly Ala Asp Met Phe Gly Ala Gly Ser
        50                  55                  60

Tyr Val Arg Pro Trp Asn Thr Met Ser Asp Pro Leu Glu Ile Ala Lys
65                  70                  75                  80

Tyr Lys Val Glu Ala Asn Phe Glu Phe Ile Glu Lys Leu Gly Ala Pro
                85                  90                  95

Phe Phe Ala Phe His Asp Arg Asp Ile Ala Pro Glu Gly Asp Thr Leu
            100                 105                 110

Ala Glu Thr Asn Lys Asn Leu Asp Thr Ile Val Ser Val Ile Lys Asp
        115                 120                 125

Arg Met Lys Ser Ser Pro Val Lys Leu Leu Trp Gly Thr Thr Asn Ala
130                 135                 140

Phe Gly Asn Pro Arg Phe Met His Gly Ala Ser Thr Ser Pro Asn Ala
                150                 155                 160
145

Asp Ile Phe Ala Tyr Ala Ala Ala Gln Val Lys Lys Ala Met Glu Ile
            165                 170                 175

Thr Lys Glu Leu Gly Gly Glu Asn Tyr Val Phe Trp Gly Gly Arg Glu
        180                 185                 190

Gly Tyr Glu Thr Leu Leu Asn Thr Asp Met Lys Leu Glu Leu Asp Asn
                195                 200                 205

Leu Ala Arg Phe Leu Lys Met Ala Val Asp Tyr Ala Lys Glu Ile Gly
210                 215                 220

Phe Asp Gly Gln Phe Leu Ile Glu Pro Lys Pro Lys Glu Pro Thr Lys
225                 230                 235                 240

His Gln Tyr Asp Phe Asp Thr Ala Thr Val Ile Gly Phe Leu Lys Thr
                245                 250                 255

Tyr Gly Leu Asp Pro Tyr Phe Lys Met Asn Ile Glu Ala Asn His Ala
            260                 265                 270

Thr Leu Ala Gly His Thr Phe Gln His Glu Leu Ala Met Cys Arg Ile
        275                 280                 285

Asn Asp Met Leu Gly Ser Ile Asp Ala Asn Gln Gly Asp Val Met Leu
                295                 300
290

Gly Trp Asp Thr Asp Gln Phe Pro Thr Asn Leu Tyr Asp Ala Thr Leu
305                 310                 315                 320

Ala Met Val Glu Val Leu Lys Ala Gly Gly Leu Lys Lys Gly Gly Leu
                325                 330                 335

Asn Phe Asp Ser Lys Val Arg Arg Gly Ser Phe Glu Pro Ser Asp Leu
            340                 345                 350

Phe Tyr Gly His Ile Ala Gly Met Asp Thr Phe Ala Lys Gly Leu Ile
        355                 360                 365

Ile Ala Asn Lys Ile Val Glu Asp Gly Lys Phe Asp Ala Phe Val Ala
        370                 375                 380

Asp Arg Tyr Ser Ser Tyr Thr Asn Gly Ile Gly Lys Asp Ile Val Glu
385                 390                 395                 400
```

-continued

Gly Lys Val Gly Phe Lys Glu Leu Glu Gln Tyr Ala Leu Thr Ala Lys
                405                 410                 415

Ile Gln Asn Lys Ser Gly Arg Gln Glu Met Leu Glu Ala Leu Leu Asn
            420                 425                 430

Gln Tyr Ile Leu Glu Thr Lys
        435

<210> SEQ ID NO 24
<211> LENGTH: 444
<212> TYPE: PRT
<213> ORGANISM: Thermotoga maritima

<400> SEQUENCE: 24

Met Ala Glu Phe Phe Pro Glu Ile Pro Lys Ile Gln Phe Glu Gly Lys
1               5                   10                  15

Glu Ser Thr Asn Pro Leu Ala Phe Arg Phe Tyr Asp Pro Asn Glu Val
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Glu Arg Pro Trp Asn Arg Phe Ser Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
130                 135                 140

Phe Ser His Pro Arg Tyr Met His Gly Ala Ala Thr Thr Cys Ser Ala
145                 150                 155                 160

Asp Val Phe Ala Tyr Ala Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Leu Glu Leu Glu Asn
        195                 200                 205

Leu Ala Arg Phe Leu Arg Met Ala Val Glu Tyr Ala Lys Lys Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Asn
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
    290                 295                 300

Gly Trp Asp Thr Asp Gln Phe Pro Thr Asn Ile Tyr Asp Thr Thr Leu
305                 310                 315                 320

Ala Met Tyr Glu Val Ile Lys Ala Gly Gly Phe Thr Lys Gly Gly Leu

```
            325                 330                 335
Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
            355                 360                 365

Ile Ala Tyr Lys Leu Ala Lys Asp Gly Val Phe Asp Lys Phe Ile Glu
            370                 375                 380

Glu Lys Tyr Arg Ser Phe Lys Glu Gly Ile Gly Lys Glu Ile Val Glu
385                 390                 395                 400

Gly Lys Thr Asp Phe Glu Lys Leu Glu Glu Tyr Ile Ile Asp Lys Glu
                405                 410                 415

Asp Ile Glu Leu Pro Ser Gly Lys Gln Glu Tyr Leu Glu Ser Leu Leu
            420                 425                 430

Asn Ser Tyr Ile Val Lys Thr Ile Ala Glu Leu Arg
            435                 440

<210> SEQ ID NO 25
<211> LENGTH: 441
<212> TYPE: PRT
<213> ORGANISM: Bacillus stearothermophilus

<400> SEQUENCE: 25

Met Pro Tyr Phe Asp Asn Ile Ser Thr Ile Ala Tyr Glu Gly Pro Ala
1               5                   10                  15

Ser Lys Asn Pro Leu Ala Phe Lys Phe Tyr Asn Pro Glu Glu Lys Val
            20                  25                  30

Gly Asp Lys Thr Met Glu Glu His Leu Arg Phe Ser Val Ala Tyr Trp
        35                  40                  45

His Thr Phe Thr Gly Asp Gly Ser Asp Pro Phe Gly Ala Gly Asn Met
    50                  55                  60

Ile Arg Pro Trp Asn Lys Tyr Ser Gly Met Asp Leu Ala Lys Ala Arg
65                  70                  75                  80

Val Glu Ala Ala Phe Glu Phe Phe Glu Lys Leu Asn Ile Pro Phe Phe
                85                  90                  95

Cys Phe His Asp Val Asp Ile Ala Pro Glu Gly Glu Thr Leu Lys Glu
            100                 105                 110

Thr Tyr Lys Asn Leu Asp Ile Ile Val Asp Met Ile Glu Glu Tyr Met
        115                 120                 125

Lys Thr Ser Lys Thr Lys Leu Leu Trp Asn Thr Ala Asn Leu Phe Thr
130                 135                 140

His Pro Arg Phe Val His Gly Ala Ala Thr Ser Cys Asn Ala Asp Val
145                 150                 155                 160

Phe Ala Tyr Ala Ala Lys Val Lys Lys Gly Leu Glu Ile Ala Lys
                165                 170                 175

Arg Leu Gly Ala Glu Asn Tyr Val Phe Trp Gly Gly Arg Glu Gly Tyr
            180                 185                 190

Glu Thr Leu Leu Asn Thr Asp Met Lys Leu Glu Leu Asp Asn Leu Ala
        195                 200                 205

Arg Phe Leu His Met Ala Val Asp Tyr Ala Lys Glu Ile Gly Phe Asp
    210                 215                 220

Gly Gln Phe Leu Ile Glu Pro Lys Pro Lys Glu Pro Thr Lys His Gln
225                 230                 235                 240

Tyr Asp Phe Asp Val Ala Thr Ala Leu Ala Phe Leu Gln Thr Tyr Gly
                245                 250                 255
```

Leu Lys Asp Tyr Phe Lys Phe Asn Ile Glu Ala Asn His Ala Thr Leu
        260                 265                 270

Ala Gly His Thr Phe Glu His Glu Leu Arg Val Ala Arg Ile His Gly
        275                 280                 285

Met Leu Gly Ser Val Asp Ala Asn Gln Gly Asp Met Leu Leu Gly Trp
        290                 295                 300

Asp Thr Asp Glu Phe Pro Thr Asp Leu Tyr Ser Thr Thr Leu Ala Met
305                 310                 315                 320

Tyr Glu Ile Leu Lys Asn Gly Gly Leu Gly Arg Gly Gly Leu Asn Phe
                325                 330                 335

Asp Ala Lys Val Arg Arg Gly Ser Phe Glu Pro Glu Asp Leu Phe Tyr
                340                 345                 350

Ala His Ile Ala Gly Met Asp Ser Phe Ala Val Gly Leu Lys Val Ala
                355                 360                 365

His Arg Leu Ile Glu Asp Arg Val Phe Asp Glu Phe Ile Glu Glu Arg
                370                 375                 380

Tyr Lys Ser Tyr Thr Glu Gly Ile Gly Arg Glu Ile Val Glu Gly Thr
385                 390                 395                 400

Ala Asp Phe His Lys Leu Glu Ala His Ala Leu Gln Leu Gly Glu Ile
                405                 410                 415

Gln Asn Gln Ser Gly Arg Gln Glu Arg Leu Lys Thr Leu Leu Asn Gln
                420                 425                 430

Tyr Leu Leu Glu Val Cys Ala Arg
        435                 440

<210> SEQ ID NO 26
<211> LENGTH: 438
<212> TYPE: PRT
<213> ORGANISM: Bacteroides stercoris

<400> SEQUENCE: 26

Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Glu
                20                  25                  30

Lys Val Ile Met Gly Lys Lys Met Lys Asp Trp Leu Lys Phe Ser Met
                35                  40                  45

Ala Trp Trp His Thr Leu Cys Ala Glu Gly Gly Asp Gln Phe Gly Gly
        50                  55                  60

Gly Thr Lys His Phe Pro Trp Asn Gly Asp Ala Asp Lys Leu Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Asp Glu Ala Asp
                100                 105                 110

Thr Ile Glu Glu Tyr Glu Ala Asn Leu Lys Ala Ile Val Ala Tyr Ala
                115                 120                 125

Lys Gln Lys Gln Glu Glu Thr Gly Ile Lys Leu Leu Trp Gly Thr Ala
        130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Ser Asn Tyr Val Phe Trp Gly Gly
                180                 185                 190

Arg Glu Gly Tyr Met Ser Leu Leu Asn Thr Asp Gln Lys Arg Glu Lys
            195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Ala Asp Thr Glu Thr Val Val Gly Phe Leu
            245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
            275                 280                 285

Val Asp Asn Gly Met Leu Gly Ser Ile Asp Ala Asn Arg Gly Asp Tyr
            290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Phe Gly Asp Gly
            325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
            355                 360                 365

Leu Glu Ser Ala Ala Lys Leu Leu Glu Glu Ser Pro Tyr Lys Lys Met
            370                 375                 380

Leu Ala Asp Arg Tyr Ala Ser Phe Asp Ser Gly Lys Gly Lys Glu Phe
385                 390                 395                 400

Glu Glu Gly Lys Leu Thr Leu Glu Asp Val Val Ala Tyr Ala Lys Ala
            405                 410                 415

Asn Gly Glu Pro Lys Gln Thr Ser Gly Lys Gln Glu Leu Tyr Glu Ala
            420                 425                 430

Ile Val Asn Met Tyr Cys
            435

<210> SEQ ID NO 27
<211> LENGTH: 442
<212> TYPE: PRT
<213> ORGANISM: Parabacteroides distasonis

<400> SEQUENCE: 27

Met Ser Tyr Phe Lys Gly Glu Lys Glu Phe Pro Gly Ile Gly Gln
1               5                   10                  15

Ile Gln Phe Glu Gly Arg Glu Ser Lys Asn Pro Leu Ala Phe His Tyr
            20                  25                  30

Tyr Asp Ala Asp Lys Val Val Met Gly Lys Thr Leu Lys Asp His Leu
            35                  40                  45

Arg Phe Ala Met Ala Tyr Trp His Thr Leu Cys Ala Glu Gly Gly Asp
    50                  55                  60

Gln Phe Gly Gly Gly Thr Lys Thr Phe Pro Trp Asn Asp Ser Thr Asp
65                  70                  75                  80

Ala Ile Thr Arg Ala Lys Tyr Lys Met Asp Ala Ala Phe Glu Phe Met
            85                  90                  95

Thr Lys Cys Asn Ile Pro Tyr Tyr Cys Phe His Asp Val Asp Val Val
            100                 105                 110

Asp Glu Ala Pro Thr Leu Gly Glu Phe Glu Lys Arg Leu Gln Thr Met

```
            115                 120                 125
Val Glu His Ala Lys Glu His Gln Ala Ala Thr Gly Lys Lys Leu Leu
        130                 135                 140

Trp Ser Thr Ala Asn Val Phe Gly His Lys Arg Tyr Met Asn Gly Ala
145                 150                 155                 160

Ala Thr Asn Pro Tyr Phe Pro Thr Val Ala Cys Ala Gly Thr Gln Ile
                165                 170                 175

Lys Asn Ala Ile Asp Ala Cys Ile Ala Leu Gly Gly Glu Asn Tyr Val
            180                 185                 190

Phe Trp Gly Gly Arg Glu Gly Tyr Met Ser Leu Leu Asn Thr Asn Met
        195                 200                 205

Lys Arg Glu Lys Asp His Leu Ala Met Met Leu Thr Met Ala Arg Asp
210                 215                 220

Tyr Gly Arg Lys Asn Gly Phe Lys Gly Thr Phe Leu Ile Glu Pro Lys
225                 230                 235                 240

Pro Met Glu Pro Thr Lys His Gln Tyr Asp Val Asp Ser Glu Thr Val
                245                 250                 255

Ile Gly Phe Leu Arg His Tyr Gly Leu Asp Lys Asp Phe Ala Leu Asn
            260                 265                 270

Ile Glu Val Asn His Ala Thr Leu Ala Gly His Thr Phe Glu His Glu
        275                 280                 285

Leu Gln Ala Ala Ala Asp Ala Gly Met Leu Cys Ser Ile Asp Ala Asn
290                 295                 300

Arg Gly Asp Tyr Gln Asn Gly Trp Asp Thr Asp Gln Phe Pro Met Asp
305                 310                 315                 320

Ile Tyr Glu Leu Ala Gln Ala Trp Leu Val Ile Leu Glu Gly Gly Gly
                325                 330                 335

Leu Thr Thr Gly Gly Thr Asn Phe Asp Ala Lys Thr Arg Arg Asn Ser
            340                 345                 350

Thr Asp Leu Glu Asp Ile Phe Ile Ala His Ile Gly Gly Met Asp Ala
        355                 360                 365

Phe Ala Arg Ala Leu Met Ile Ala Ala Asp Ile Leu Glu Asn Ser Asp
370                 375                 380

Tyr Arg Lys Met Arg Ala Glu Arg Tyr Ala Ser Phe Asp Ala Gly Glu
385                 390                 395                 400

Gly Lys Ala Phe Glu Asp Gly Lys Leu Thr Leu Glu Asp Leu Arg Thr
                405                 410                 415

Ile Ala Leu Arg Asp Gly Glu Pro Lys Gln Ile Ser Gly Lys Gln Glu
            420                 425                 430

Leu Tyr Glu Met Ile Val Asn Leu His Ile
        435                 440

<210> SEQ ID NO 28
<211> LENGTH: 439
<212> TYPE: PRT
<213> ORGANISM: Prevotella ruminicola

<400> SEQUENCE: 28

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45
```

```
Trp Trp His Thr Leu Gly Gly Ala Ser Ala Asp Gln Phe Gly Gly Gln
 50              55                  60
Thr Arg Ser Tyr Glu Trp Asp Lys Ala Ala Asp Ala Val Gln Arg Ala
 65                  70                  75                  80
Lys Asp Lys Met Asp Ala Gly Phe Glu Ile Met Asp Lys Leu Gly Ile
                 85                  90                  95
Glu Tyr Phe Cys Phe His Asp Val Asp Leu Val Glu Glu Gly Glu Thr
                100                 105                 110
Ile Ala Glu Tyr Glu Arg Arg Met Lys Glu Ile Thr Asp Tyr Ala Leu
            115                 120                 125
Val Lys Met Lys Glu Tyr Pro Asn Ile Lys Leu Leu Trp Gly Thr Ala
130                 135                 140
Asn Val Phe Gly Asn Lys Arg Tyr Ala Asn Gly Ala Ser Thr Asn Pro
145                 150                 155                 160
Asp Phe Asp Val Val Arg Ala Ile Val Gln Ile Lys Asn Ala Ile
                165                 170                 175
Asp Ala Thr Ile Lys Leu Gly Gly Thr Asn Tyr Val Phe Trp Gly Gly
            180                 185                 190
Arg Glu Gly Tyr Met Ser Leu Leu Asn Thr Asp Gln Lys Arg Glu Lys
        195                 200                 205
Glu His Met Ala Thr Met Leu Thr Met Ala Arg Asp Tyr Ala Arg Ala
    210                 215                 220
Lys Gly Phe Lys Gly Thr Phe Leu Ile Glu Pro Lys Pro Met Glu Pro
225                 230                 235                 240
Ser Lys His Gln Tyr Asp Val Asp Thr Glu Thr Val Cys Gly Phe Leu
                245                 250                 255
Arg Ala His Gly Leu Asp Lys Asp Phe Lys Val Asn Ile Glu Val Asn
            260                 265                 270
His Ala Thr Leu Ala Gly His Thr Phe Glu His Glu Leu Ala Cys Ala
        275                 280                 285
Val Asp Asn Gly Met Leu Gly Ser Ile Asp Ala Asn Arg Gly Asp Ala
    290                 295                 300
Gln Asn Gly Trp Asp Thr Asp Gln Phe Pro Ile Asp Asn Phe Glu Leu
305                 310                 315                 320
Thr Gln Ala Met Leu Glu Ile Ile Arg Asn Gly Gly Leu Gly Asn Gly
                325                 330                 335
Gly Thr Asn Phe Asp Ala Lys Ile Arg Arg Asn Ser Thr Asp Leu Glu
            340                 345                 350
Asp Leu Phe Ile Ala His Ile Ser Gly Met Asp Ala Met Ala Arg Ala
        355                 360                 365
Leu Met Asn Ala Ala Ala Ile Leu Glu Glu Ser Glu Leu Pro Lys Met
    370                 375                 380
Lys Lys Glu Arg Tyr Ala Ser Phe Asp Asn Gly Ile Gly Lys Asp Phe
385                 390                 395                 400
Glu Asp Gly Lys Leu Thr Leu Glu Gln Ala Tyr Glu Tyr Gly Lys Lys
                405                 410                 415
Val Glu Glu Pro Lys Gln Thr Ser Gly Lys Gln Glu Lys Tyr Glu Thr
            420                 425                 430
Thr Val Ala Leu Tyr Cys Lys
        435

<210> SEQ ID NO 29
<211> LENGTH: 436
<212> TYPE: PRT
```

<213> ORGANISM: Agrobacterium tumefaciens

<400> SEQUENCE: 29

```
Met Ser Thr Gly Phe Phe Gly Asp Ile Thr Lys Ile Lys Tyr Glu Gly
 1               5                  10                  15
Pro Asp Ser Thr Asn Pro Leu Ala Phe Arg His Tyr Asn Pro Asp Glu
            20                  25                  30
Ile Val Ala Gly Lys Arg Met Glu Asp His Leu Arg Phe Ala Val Ala
        35                  40                  45
Tyr Trp His Thr Phe Thr Trp Pro Gly Gly Asp Pro Phe Gly Gly Gln
50                  55                  60
Thr Phe Gln Arg Pro Trp Phe Glu Asp Thr Met Gln Ala Ala Lys Leu
65                  70                  75                  80
Lys Ala Asp Val Ala Phe Glu Phe Phe Ser Leu Leu Gly Ser Pro Phe
                85                  90                  95
Tyr Cys Phe His Asp Ala Asp Val Arg Pro Glu Gly Lys Asn Phe Ala
            100                 105                 110
Glu Asn Thr Lys Asn Leu Asn Glu Ile Val Asp Tyr Phe Ala Glu Lys
        115                 120                 125
Gln Ala Gln Thr Gly Val Lys Leu Leu Trp Gly Thr Ala Asn Leu Phe
130                 135                 140
Ser Asn Arg Arg Phe Met Ser Gly Ala Ala Thr Asn Pro Asp Pro Asp
145                 150                 155                 160
Val Phe Ala Phe Ser Ala Ala Thr Val Lys Thr Cys Leu Asp Ala Thr
                165                 170                 175
Lys Lys Leu Gly Gly Ala Asn Tyr Val Leu Trp Gly Gly Arg Glu Gly
            180                 185                 190
Tyr Glu Thr Leu Leu Asn Thr Asp Leu Ser Arg Glu Leu Asp Gln Met
        195                 200                 205
Gly Arg Phe Leu Asn Leu Val Val Glu Tyr Lys Tyr Lys Ile Gly Phe
210                 215                 220
Glu Gly Thr Ile Leu Ile Glu Pro Lys Pro Gln Glu Pro Thr Lys His
225                 230                 235                 240
Gln Tyr Asp Tyr Asp Val Ala Thr Val Tyr Ala Phe Leu Gln Lys Asn
                245                 250                 255
Gly Leu Glu Lys Glu Val Lys Val Asn Ile Glu Gln Gly His Ala Ile
            260                 265                 270
Leu Ala Gly His Ser Phe Glu His Glu Leu Ala Leu Ala Asn Ala Phe
        275                 280                 285
Gly Ile Phe Gly Ser Ile Asp Met Asn Arg Asn Asp Tyr Gln Ser Gly
290                 295                 300
Trp Asp Thr Asp Gln Phe Pro Asn Asn Val Pro Glu Met Ala Leu Ala
305                 310                 315                 320
Tyr Tyr His Val Leu Ala Gly Gly Phe Lys Asn Gly Gly Thr Asn
                325                 330                 335
Phe Asp Ala Lys Leu Arg Arg Gln Ser Leu Asp Pro Gln Asp Leu Leu
            340                 345                 350
Ile Gly His Ile Gly Gly Met Asp Cys Cys Ala Arg Gly Leu Lys Ala
        355                 360                 365
Ala Ala Lys Met Ile Glu Asp Gly Ala Leu Ser Lys Pro Leu Ser Glu
370                 375                 380
Arg Tyr Ala Lys Trp Asp Ser Ala Glu Ala Gln Lys Met Leu Arg Gly
385                 390                 395                 400
```

Glu Leu Lys Leu Asp Asp Ile Ala Ala Leu Val Glu Arg Glu Asp Ile
            405                 410                 415

Asn Pro Glu Pro Lys Ser Gly Arg Gln Glu Tyr Leu Glu Asn Val Val
        420                 425                 430

Asn Arg Tyr Val
        435

<210> SEQ ID NO 30
<211> LENGTH: 439
<212> TYPE: PRT
<213> ORGANISM: Clostridium cellulovorans

<400> SEQUENCE: 30

Met Arg Glu Tyr Phe Ala Asn Val Pro Lys Ile Lys Tyr Glu Gly Lys
1               5                   10                  15

Asp Ser Lys Asn Pro Leu Ala Phe Lys Tyr Tyr Asn Pro Asp Glu Val
            20                  25                  30

Val Gly Gly Lys Thr Met Lys Glu His Leu Arg Phe Thr Leu Ser Tyr
        35                  40                  45

Trp His Thr Leu Thr Gly Ala Gly Ser Asp Pro Phe Gly Val Gly Thr
    50                  55                  60

Met Leu Arg Pro Trp Asp Cys Ala Glu Asp Glu Met Glu Leu Ala Lys
65                  70                  75                  80

Met Arg Met Glu Ala Asn Phe Glu Leu Met Asp Lys Leu Gly Ile Glu
                85                  90                  95

Tyr Phe Ala Phe His Asp Arg Asp Ile Ala Pro Glu Gly Lys Thr Leu
            100                 105                 110

Ala Asp Thr Asn Glu Lys Leu Asp Glu Ile Val Ala Tyr Cys Lys Glu
        115                 120                 125

Leu Met Gln Lys His Gly Lys Lys Leu Leu Trp Gly Thr Ala Asn Met
    130                 135                 140

Phe Gly Asn Pro Arg Phe Val His Gly Ala Ala Thr Thr Cys Asn Ala
145                 150                 155                 160

Asp Val Phe Ala Tyr Ala Ala Ala Gln Thr Lys Lys Ala Met Asp Val
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Leu Gly Leu Glu Gln Asp Asn
        195                 200                 205

Leu Ala Arg Phe Phe Gln Met Ala Val Asp Tyr Ala Lys Lys Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Val Leu Gly Phe Leu Arg Lys
                245                 250                 255

Tyr Asn Leu Glu Lys Tyr Phe Lys Met Asn Ile Glu Ala Asn His Ala
            260                 265                 270

Thr Leu Ala Gln His Thr Phe Gln His Glu Val Ala Val Ala Arg Val
        275                 280                 285

Asn Gly Val Leu Gly Ser Leu Asp Val Asn Gln Gly Asp Pro Asn Leu
    290                 295                 300

Gly Trp Asp Thr Asp Gln Phe Pro Thr Asn Ile Tyr Asp Ala Thr Met
305                 310                 315                 320

Val Met Tyr Glu Val Leu Lys Asn Gly Gly Ile Ala Pro Gly Gly Leu
                325                 330                 335

```
Asn Phe Asp Ala Lys Thr Arg Arg Ala Ser Phe Glu Pro Glu Asp Leu
            340                 345                 350

Phe Leu Ser Tyr Ile Ala Gly Met Asp Thr Met Ala Lys Gly Leu Arg
            355                 360                 365

Val Ala Tyr Ser Leu Leu Asp Asp Ala Val Leu Glu Asn Asn Thr Ser
370                 375                 380

Glu Arg Tyr Lys Thr Phe Ser Glu Gly Ile Gly Lys Asp Ile Val Glu
385                 390                 395                 400

Gly Lys Val Asp Phe Glu Ser Leu Glu Lys Tyr Ala Leu Glu Asn Ser
                405                 410                 415

Val Ile Ser Asn Lys Ser Gly Arg Gln Glu Tyr Leu Glu Ser Val Val
            420                 425                 430

Asn Gln Tyr Ile Phe Asn Asp
            435

<210> SEQ ID NO 31
<211> LENGTH: 440
<212> TYPE: PRT
<213> ORGANISM: Burkholderia cenocepacia

<400> SEQUENCE: 31

Met Ser Tyr Phe Glu His Ile Pro Ala Ile Arg Tyr Glu Gly Pro Gln
1               5                   10                  15

Ser Asp Asn Pro Leu Ala Tyr His His Tyr Asp Pro Asp Lys Arg Val
            20                  25                  30

Leu Gly Lys Thr Leu Ala Glu His Leu Arg Ile Ala Val Cys Tyr Trp
        35                  40                  45

His Thr Phe Val Trp Pro Gly His Asp Ile Phe Gly Gln Gly Ala Phe
    50                  55                  60

Gln Arg Pro Trp Gln Gln Pro Gly Asp Ala Leu Glu Arg Ala Arg Gln
65                  70                  75                  80

Lys Ala Asp Ala Ala Phe Glu Phe Phe Thr Lys Leu Gly Thr Pro Phe
                85                  90                  95

Tyr Thr Phe His Asp Thr Asp Val Ala Pro Glu Gly Asp Ser Leu Arg
            100                 105                 110

Asp Tyr Ala Ala Asn Phe Ala Arg Met Val Asp Tyr Leu Gly Glu Arg
        115                 120                 125

Gln Gln Ala Ser Gly Val Arg Leu Leu Trp Gly Thr Ala Asn Leu Phe
    130                 135                 140

Ser His Pro Arg Phe Ala Ala Gly Ala Ala Thr Asn Pro Asn Pro Asp
145                 150                 155                 160

Val Phe Ala Trp Ala Ala Thr Gln Val Cys His Ala Leu Asp Ala Thr
                165                 170                 175

His Arg Leu Gly Gly Glu Asn Tyr Val Leu Trp Gly Gly Arg Glu Gly
            180                 185                 190

Tyr Glu Thr Leu Leu Asn Thr Asp Leu Lys Arg Glu Arg Asp Gln Phe
        195                 200                 205

Ala Arg Phe Leu Ser Met Val Val Glu His Lys His Arg Ile Gly Phe
    210                 215                 220

Lys Gly Ala Leu Leu Ile Glu Pro Lys Pro Gln Glu Pro Thr Lys His
225                 230                 235                 240

Gln Tyr Asp Tyr Asp Val Ala Thr Val His Gly Phe Leu Val Gln Tyr
                245                 250                 255

Gly Leu Gln Asn Glu Ile Arg Val Asn Ile Glu Ala Asn His Ala Thr
```

-continued

```
                260                 265                 270
Leu Ala Gly His Ser Phe His His Glu Ile Ala Asn Ala Phe Ala Leu
            275                 280                 285
Gly Val Phe Gly Ser Val Asp Ala Asn Arg Gly Asp Pro Gln Asn Gly
            290                 295                 300
Trp Asp Thr Asp Gln Phe Pro Asn Ser Val Glu Leu Thr Leu Ala
305                 310                 315                 320
Phe Tyr Glu Ile Leu Arg His Gly Gly Phe Thr Thr Gly Gly Met Asn
                325                 330                 335
Phe Asp Ala Lys Val Arg Arg Gln Ser Ile Asp Pro Glu Asp Leu Phe
            340                 345                 350
Tyr Gly His Val Gly Ala Ile Asp Val Leu Ala Leu Ala Leu Glu Arg
                355                 360                 365
Ala Ala Val Leu Val Glu Asn Asp Arg Leu Asp Ala Leu Arg Arg Gln
            370                 375                 380
Arg Tyr Ala Gln Trp Asp Asp Ala Phe Gly Arg Lys Ile Leu Ser Gly
385                 390                 395                 400
Gly Tyr Thr Leu Glu Ser Leu Ala Ala Asp Ala Leu Ala Arg Gly Val
                405                 410                 415
Asn Pro Arg His Ala Ser Gly Ala Gln Glu Arg Leu Glu Asn Ile Val
            420                 425                 430
Asn Gln Ala Ile Tyr Gly Leu Arg
            435                 440

<210> SEQ ID NO 32
<211> LENGTH: 439
<212> TYPE: PRT
<213> ORGANISM: Lactococcus lactis

<400> SEQUENCE: 32

Met Ala Tyr Phe Asn Asp Ile Ala Pro Ile Lys Tyr Glu Gly Thr Lys
1               5                   10                  15
Thr Lys Asn Met Phe Ala Phe Arg His Tyr Asn Pro Glu Glu Val Val
                20                  25                  30
Ala Gly Lys Thr Met Glu Glu Gln Leu His Phe Ala Leu Ala Phe Trp
            35                  40                  45
His Thr Ile Thr Met Asp Gly Ser Asp Pro Phe Gly Gly Ala Thr Met
        50                  55                  60
Glu Arg Pro Trp Asp Leu Glu Gly Gly Ser Glu Leu Asp Arg Ala His
65                  70                  75                  80
Arg Arg Val Asp Ala Phe Phe Glu Ile Ala Glu Lys Leu Gly Val Lys
                85                  90                  95
Tyr Tyr Cys Phe His Asp Ile Asp Ile Ala Pro Thr Gly Asn Ser Leu
                100                 105                 110
Lys Glu Phe Tyr Ala Asn Leu Asp Glu Ile Thr Asp His Leu Leu Glu
            115                 120                 125
Lys Gln Lys Ala Thr Gly Ile Lys Leu Leu Trp Asn Thr Ala Asn Met
        130                 135                 140
Phe Ser Asn Pro Arg Tyr Met Asn Gly Val Ser Thr Ser Asn Arg Ala
145                 150                 155                 160
Glu Val Phe Ala Tyr Gly Ala Ala Gln Val Lys Lys Gly Leu Glu Leu
                165                 170                 175
Ser Lys Lys Leu Gly Gly Glu Asn Tyr Val Phe Trp Gly Gly Arg Glu
            180                 185                 190
```

Gly Tyr Glu Ser Leu Leu Asn Thr Asp Met Gly Leu Glu Met Asp His
                195                 200                 205

Met Ala Lys Phe Phe His Leu Ala Ile Asp Tyr Ala Lys Ser Ile Asn
210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
                260                 265                 270

Trp Leu Ala Gly His Thr Phe Glu His Glu Leu Asn Thr Ala Arg Thr
                275                 280                 285

Phe Asn Ala Leu Gly Ser Ile Asp Ala Asn Gln Gly Asn Tyr Leu Leu
                290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Asn Phe Asp Ala Lys Val Arg Arg Thr Ser Phe Lys Ala Glu Asp Leu
                340                 345                 350

Ile Leu Ala His Ile Ala Gly Met Asp Thr Tyr Ala Arg Ala Leu Lys
                355                 360                 365

Gly Ala Ala Ile Ile Glu Asp Lys Phe Leu Ser Asp Ile Val Asp
                370                 375                 380

Glu Arg Tyr Ser Ser Tyr Arg Asn Thr Glu Val Gly Gln Ser Ile Glu
385                 390                 395                 400

Asn Gly Thr Ala Thr Phe Glu Ser Leu Ala Ala Phe Ala Leu Glu Tyr
                405                 410                 415

Gly Asp Asp Ile Glu Leu Asp Ser Asn His Leu Glu Tyr Ile Lys Ser
                420                 425                 430

Val Leu Asn Asp Tyr Leu Val
                435

<210> SEQ ID NO 33
<211> LENGTH: 438
<212> TYPE: PRT
<213> ORGANISM: Thermoanaerobacter thermohydrosulfuricus

<400> SEQUENCE: 33

Met Glu Tyr Phe Lys Asn Val Pro Gln Ile Lys Tyr Glu Gly Pro Lys
1               5                   10                  15

Ser Asn Asn Pro Tyr Ala Phe Lys Phe Tyr Asn Pro Asp Glu Ile Ile
                20                  25                  30

Asp Gly Lys Pro Leu Lys Glu His Leu Arg Phe Ser Val Ala Tyr Trp
                35                  40                  45

His Thr Phe Thr Ala Asn Gly Thr Asp Pro Phe Gly Ala Pro Thr Met
                50                  55                  60

Gln Arg Pro Trp Asp His Phe Thr Asp Pro Met Asp Ile Ala Lys Ala
65                  70                  75                  80

Arg Val Glu Ala Ala Phe Glu Leu Phe Glu Lys Leu Asp Val Pro Phe
                85                  90                  95

Phe Cys Phe His Asp Arg Asp Ile Ala Pro Glu Gly Glu Thr Leu Arg
                100                 105                 110

Glu Thr Asn Lys Asn Leu Asp Thr Ile Val Ala Met Ile Lys Asp Tyr
                115                 120                 125

Leu Lys Thr Ser Lys Thr Lys Val Leu Trp Gly Thr Ala Asn Leu Phe
          130                 135                 140

Ser Asn Pro Arg Phe Val His Gly Ala Ala Thr Ser Cys Asn Ala Asp
145                 150                 155                 160

Val Phe Ala Tyr Ala Ala Ala Gln Val Lys Lys Ala Leu Glu Ile Thr
                165                 170                 175

Lys Glu Leu Gly Gly Gln Asn Tyr Val Phe Trp Gly Gly Arg Glu Gly
            180                 185                 190

Tyr Glu Thr Leu Leu Asn Thr Asp Met Glu Leu Glu Leu Asp Asn Leu
        195                 200                 205

Ala Arg Phe Leu His Met Ala Val Glu Tyr Ala Gln Glu Ile Gly Phe
    210                 215                 220

Glu Gly Gln Phe Leu Ile Glu Pro Lys Pro Lys Glu Pro Thr Lys His
225                 230                 235                 240

Gln Tyr Asp Phe Asp Ala Ala Ser Val His Ala Phe Leu Lys Lys Tyr
                245                 250                 255

Asp Leu Asp Lys Tyr Phe Lys Leu Asn Ile Glu Ala Asn His Ala Thr
            260                 265                 270

Leu Ala Gly His Asp Phe Gln His Glu Leu Arg Tyr Ala Arg Ile Asn
        275                 280                 285

Asn Met Leu Gly Ser Ile Asp Ala Asn Met Gly Asp Met Leu Leu Gly
    290                 295                 300

Trp Asp Thr Asp Gln Tyr Pro Thr Asp Ile Arg Met Thr Thr Leu Ala
305                 310                 315                 320

Met Tyr Glu Val Ile Lys Met Gly Gly Phe Asn Lys Gly Gly Leu Asn
                325                 330                 335

Phe Asp Ala Lys Val Arg Arg Ala Ser Phe Glu Pro Glu Asp Leu Phe
            340                 345                 350

Leu Gly His Ile Ala Gly Met Asp Ala Phe Ala Lys Gly Phe Lys Val
        355                 360                 365

Ala Tyr Lys Leu Val Lys Asp Gly Val Phe Asp Arg Phe Ile Glu Glu
    370                 375                 380

Arg Tyr Lys Ser Tyr Arg Glu Gly Ile Gly Ala Glu Ile Val Ser Gly
385                 390                 395                 400

Lys Ala Asn Phe Lys Thr Leu Glu Glu Tyr Ala Leu Asn Asn Pro Lys
                405                 410                 415

Ile Glu Asn Lys Ser Gly Lys Gln Glu Leu Leu Glu Ser Ile Leu Asn
            420                 425                 430

Gln Tyr Leu Phe Ser Glu
        435

<210> SEQ ID NO 34
<211> LENGTH: 439
<212> TYPE: PRT
<213> ORGANISM: Reticulitermes speratus

<400> SEQUENCE: 34

Met Ser Gln Ile Phe Lys Asp Ile Pro Val Ile Lys Tyr Glu Gly Pro
1               5                   10                  15

Ala Ser Lys Asn Pro Leu Ser Phe Lys Tyr Tyr Asp Ala Asn Lys Val
                20                  25                  30

Ile Asp Gly Lys Pro Met Lys Glu His Leu Arg Tyr Ala Met Ala Trp
            35                  40                  45

Trp His Asn Leu Cys Ala Thr Gly Gln Asp Met Phe Gly Pro Gly Thr

```
            50                  55                  60
Ala Asp Lys Ser Phe Gly Ser Lys Thr Val Gly Thr Met Glu His Ala
 65                  70                  75                  80

His Ala Lys Val Asp Ala Gly Phe Glu Phe Met Ser Lys Leu Gly Val
                 85                  90                  95

Glu Tyr Phe Cys Phe His Asp Ala Asp Leu Val Pro Glu Ala Asp Thr
            100                 105                 110

Leu Ser Glu Thr Asn Lys Arg Leu Asp Glu Ile Ala Glu His Ile Val
            115                 120                 125

Ala Lys Gln Lys Ala Thr Gly Ile Lys Cys Leu Trp Gly Thr Ala Asn
130                 135                 140

Leu Phe Ser Asn Pro Arg Phe Leu Asn Gly Ser Gly Ser Asn Ser
145                 150                 155                 160

Ala Asp Val Tyr Ala Tyr Ala Ala Gln Ile Lys Lys Ala Leu Asp
                165                 170                 175

Leu Thr Val Lys Phe Gly Gly Val Gly Tyr Val Phe Trp Gly Gly Arg
            180                 185                 190

Glu Gly Tyr Glu Thr Leu Leu Asn Thr Asp Val Lys Phe Glu Gln Glu
            195                 200                 205

Asn Ile Ala Asn Leu Met His Leu Ala Val Thr Tyr Gly Arg Ser Ile
210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Thr Ile Gly Phe Ile Arg
                245                 250                 255

Gln Tyr Gly Leu Glu Lys Asp Phe Lys Leu Asn Ile Glu Ala Asn His
            260                 265                 270

Ala Thr Leu Ala Gly His Thr Phe Gln His Asp Leu Arg Ile Ser Ala
            275                 280                 285

Ile Asn Gly Met Leu Gly Ser Val Asp Ala Asn Thr Gly Asp Pro Leu
            290                 295                 300

Leu Gly Trp Asp Thr Asp Glu Phe Pro Tyr Ser Val Tyr Asp Thr Thr
305                 310                 315                 320

Leu Ala Met Tyr Glu Ile Ile Lys Ala Gly Gly Leu Thr Gly Gly Leu
                325                 330                 335

Asn Phe Asp Ser Lys Val Arg Arg Pro Ser Tyr Thr His Glu Asp Leu
            340                 345                 350

Phe Tyr Gly Phe Ile Leu Gly Met Asp Ser Phe Ala Leu Gly Leu Ile
            355                 360                 365

Lys Ala Lys Ala Leu Ile Ala Asp Gly Arg Leu Asp Ser Phe Val Lys
370                 375                 380

Asp Arg Tyr Ala Ser Tyr Gly Ser Gly Ile Gly Ala Lys Ile Arg Asp
385                 390                 395                 400

His Ser Ala Thr Leu Glu Glu Leu Ala Ala Tyr Ala Leu Ala Lys Asp
                405                 410                 415

Thr Val Ala Leu Pro Gly Ser Gly Arg Gln Glu Tyr Leu Glu Ser Ile
            420                 425                 430

Ile Asn Gln Ile Leu Phe Gln
            435

<210> SEQ ID NO 35
<211> LENGTH: 438
<212> TYPE: PRT
<213> ORGANISM: uncultured bacteria from cow rumen
```

<400> SEQUENCE: 35

```
Met Ser Glu Ile Phe Ala Asn Ile Pro Val Ile Pro Tyr Glu Gly Pro
1               5                   10                  15

Gln Ser Lys Asn Pro Leu Ala Phe Lys Phe Tyr Asp Ala Asp Lys Val
            20                  25                  30

Ile Leu Gly Lys Lys Met Ser Glu His Leu Pro Phe Ala Met Ala Trp
        35                  40                  45

Trp His Asn Leu Cys Ala Gly Gly Thr Asp Met Phe Gly Arg Asp Thr
    50                  55                  60

Ala Asp Lys Ser Phe Gly Ala Glu Lys Gly Thr Met Ala His Ala Arg
65                  70                  75                  80

Ala Lys Val Asp Ala Gly Phe Glu Phe Met Lys Lys Val Gly Val Lys
                85                  90                  95

Tyr Phe Cys Phe His Asp Val Asp Leu Val Pro Glu Ala Asp Asp Ile
            100                 105                 110

Lys Glu Thr Asn Arg Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
130                 135                 140

Phe Gly Asn Pro Arg Tyr Met Asn Gly Ala Gly Ser Thr Asn Ser Ala
145                 150                 155                 160

Asp Val Phe Cys Phe Ala Ala Ala Gln Ile Lys Lys Ala Leu Asp Leu
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Met Lys Phe Glu Gln Glu Asn
        195                 200                 205

Ile Ala Arg Leu Met His Leu Ala Val Asp Tyr Gly Arg Ser Ile Gly
210                 215                 220

Phe Thr Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Met Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Leu Leu Leu
290                 295                 300

Gly Trp Asp Thr Asp Glu Phe Pro Phe Asn Val Tyr Glu Ala Thr Leu
305                 310                 315                 320

Cys Met Tyr Glu Val Leu Lys Ala Gly Gly Leu Thr Gly Gly Phe Asn
                325                 330                 335

Phe Asp Ser Lys Thr Arg Arg Pro Ser Tyr Thr Leu Glu Asp Met Phe
            340                 345                 350

His Ala Tyr Ile Leu Gly Met Asp Thr Phe Ala Leu Gly Leu Ile Lys
        355                 360                 365

Ala Ala Leu Ile Glu Asp Gly Arg Leu Asp Gln Phe Val Ala Asp
370                 375                 380

Arg Tyr Ala Ser Tyr Lys Thr Gly Ile Gly Ala Lys Ile Arg Ser Gly
385                 390                 395                 400

Glu Thr Thr Leu Ala Glu Leu Ala Ala Tyr Ala Asp Lys Leu Gly Ala
```

```
                        405                 410                 415
Pro Ala Leu Pro Ser Ser Gly Arg Gln Glu Tyr Leu Glu Ser Ile Val
            420                 425                 430

Asn Ser Ile Leu Phe Gly
        435

<210> SEQ ID NO 36
<211> LENGTH: 438
<212> TYPE: PRT
<213> ORGANISM: uncultured bacteria from cow rumen

<400> SEQUENCE: 36

Met Ala Glu Ile Phe Lys Gly Ile Pro Glu Ile Arg Tyr Glu Gly Pro
1               5                   10                  15

Asn Ser Thr Asn Pro Leu Ser Phe Lys Tyr Tyr Asp Pro Asp Lys Val
            20                  25                  30

Ile Leu Gly Lys Pro Met Lys Glu His Leu Pro Phe Ala Met Ala Trp
        35                  40                  45

Trp His Asn Leu Gly Ala Ala Gly Thr Asp Met Phe Gly Arg Asp Thr
    50                  55                  60

Ala Asp Lys Ser Phe Gly Ala Glu Lys Gly Thr Met Glu His Ala Lys
65                  70                  75                  80

Ala Lys Val Asp Ala Gly Phe Glu Phe Met Lys Lys Leu Gly Ile Arg
                85                  90                  95

Tyr Phe Cys Phe His Asp Val Asp Leu Val Pro Glu Ala Asp Asp Ile
            100                 105                 110

Lys Val Thr Asn Ala Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
130                 135                 140

Phe Ser Asn Pro Arg Phe Met Asn Gly Ala Gly Ser Thr Asn Ser Ala
145                 150                 155                 160

Asp Val Phe Cys Phe Ala Ala Ala Gln Val Lys Lys Ala Leu Asp Ile
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Lys Leu Met His Leu Ala Val Asp Tyr Gly Arg Ser Ile Gly
    210                 215                 220

Phe Lys Gly Asp Phe Phe Ile Glu Pro Lys Pro Lys Glu Pro Met Lys
225                 230                 235                 240

His Gln Tyr Asp Phe Asp Ala Ala Thr Ala Ile Gly Phe Val Arg Gln
                245                 250                 255

Tyr Gly Leu Asp Lys Asp Phe Lys Met Asn Ile Glu Ala Asn His Ala
            260                 265                 270

Thr Leu Ala Gly His Thr Phe Gln His Glu Leu Arg Ile Ser Ala Ile
        275                 280                 285

Asn Gly Met Leu Gly Ser Ile Asp Ala Asn Gln Gly Asp Met Leu Leu
    290                 295                 300

Gly Trp Asp Thr Asp Glu Phe Pro Phe Asn Val Tyr Asp Thr Thr Leu
305                 310                 315                 320

Cys Met Tyr Glu Val Leu Lys Asn Gly Gly Ile Pro Gly Gly Phe Asn
                325                 330                 335
```

```
Phe Asp Ala Lys Asn Arg Arg Pro Ser Tyr Thr Ala Glu Asp Met Phe
                340                 345                 350
Tyr Gly Phe Ile Leu Gly Met Asp Ser Phe Ala Leu Gly Leu Ile Lys
            355                 360                 365
Ala Ala Lys Leu Ile Glu Asp Gly Arg Ile Asp Lys Phe Val Glu Glu
        370                 375                 380
Arg Tyr Ala Ser Tyr Lys Asp Gly Ile Gly Lys Lys Ile Arg Asp Gly
385                 390                 395                 400
Glu Thr Thr Leu Ala Glu Leu Ala Ala Tyr Ala Asp Gln Leu Gly Ala
                405                 410                 415
Pro Lys Leu Pro Gly Ser Gly Arg Gln Glu Asp Leu Gly Ser Val Phe
            420                 425                 430
Asn Gln Val Leu Phe Gly
            435

<210> SEQ ID NO 37
<211> LENGTH: 442
<212> TYPE: PRT
<213> ORGANISM: Lachnospiraceae bacterium

<400> SEQUENCE: 37

Met Lys Glu Phe Phe Pro Ser Ile Ser Pro Ile Lys Phe Glu Gly Ser
1               5                   10                  15
Glu Ser Lys Asn Pro Leu Ser Phe Lys Tyr Tyr Asp Ala Lys Arg Val
                20                  25                  30
Ile Met Gly Lys Thr Met Glu Glu His Leu Ser Phe Ala Met Ala Trp
            35                  40                  45
Trp His Asn Leu Cys Ala Ser Gly Val Asp Met Phe Gly Gln Gly Thr
        50                  55                  60
Ala Asp Lys Gly Phe Gly Glu Asn Leu Gly Thr Met Glu His Ala Lys
65                  70                  75                  80
Ala Lys Val Asp Ala Gly Ile Glu Phe Met Gln Lys Leu Gly Ile Lys
                85                  90                  95
Tyr Tyr Cys Phe His Asp Thr Asp Ile Val Pro Glu Asp Gln Glu Asp
                100                 105                 110
Ile Asn Val Thr Asn Ala Arg Leu Asp Glu Ile Thr Asp Tyr Ile Leu
            115                 120                 125
Glu Lys Thr Lys Gly Thr Asp Ile Lys Cys Leu Trp Ala Thr Cys Asn
        130                 135                 140
Met Phe Ser Asn Pro Arg Phe Met Asn Gly Ala Gly Ser Ser Asn Ser
145                 150                 155                 160
Ala Asp Val Phe Cys Phe Ala Ala Ala Gln Ala Lys Lys Gly Leu Glu
                165                 170                 175
Asn Ala Val Lys Leu Gly Ala Lys Gly Phe Val Phe Trp Gly Gly Arg
            180                 185                 190
Glu Gly Tyr Glu Thr Leu Leu Asn Thr Asp Met Lys Leu Glu Glu Glu
        195                 200                 205
Asn Ile Ala Thr Leu Phe Thr Met Cys Arg Asp Tyr Gly Arg Ser Ile
    210                 215                 220
Gly Phe Lys Gly Asp Phe Tyr Ile Glu Pro Lys Pro Lys Glu Pro Met
225                 230                 235                 240
Lys His Gln Tyr Asp Phe Asp Ala Ala Thr Ala Ile Gly Phe Leu Arg
                245                 250                 255
Lys Tyr Gly Leu Asp Lys Asp Phe Lys Met Asn Ile Glu Ala Asn His
            260                 265                 270
```

Ala Thr Leu Ala Gly His Thr Phe Gln His Glu Leu Arg Val Ser Ala
            275                 280                 285

Ile Asn Gly Met Leu Gly Ser Val Asp Ala Asn Gln Gly Asp Thr Leu
        290                 295                 300

Leu Gly Trp Asp Thr Asp Gln Phe Pro Thr Asn Val Tyr Asp Thr Thr
305                 310                 315                 320

Leu Ala Met Tyr Glu Ile Leu Lys Ala Gly Leu Ser Gly Gly Leu
                325                 330                 335

Asn Phe Asp Ser Lys Asn Arg Arg Pro Ser Asn Thr Ala Glu Asp Met
                340                 345                 350

Phe Tyr Gly Phe Ile Ala Gly Met Asp Thr Phe Ala Leu Gly Leu Ile
                355                 360                 365

Lys Ala Ala Gln Ile Ile Glu Asp Gly Arg Ile Asp Glu Phe Val Lys
            370                 375                 380

Glu Arg Tyr Ser Ser Tyr Asn Ser Gly Ile Gly Glu Lys Ile Arg Asn
385                 390                 395                 400

Arg Ser Val Thr Leu Val Glu Cys Ala Glu Tyr Ala Leu Lys Met Lys
                405                 410                 415

Lys Pro Glu Leu Pro Glu Ser Gly Arg Gln Tyr Leu Glu Thr Val
            420                 425                 430

Val Asn Asn Ile Phe Phe Asn Ser Lys Leu
            435                 440

<210> SEQ ID NO 38
<211> LENGTH: 442
<212> TYPE: PRT
<213> ORGANISM: Lachnospiraceae bacterium

<400> SEQUENCE: 38

Met Lys Glu Phe Phe Pro Gly Ile Ser Pro Val Lys Phe Glu Gly Ser
1               5                   10                  15

Glu Ser Lys Asn Pro Leu Ser Phe Lys Tyr Tyr Asp Ala Lys Arg Val
            20                  25                  30

Ile Met Gly Lys Thr Met Glu Glu His Leu Ser Phe Ala Met Ala Trp
        35                  40                  45

Trp His Asn Leu Cys Ala Ser Gly Val Asp Met Phe Gly Gln Gly Thr
    50                  55                  60

Ala Asp Lys Gly Phe Gly Glu Ser Ser Gly Thr Met Gly His Ala Lys
65                  70                  75                  80

Ala Lys Val Asp Ala Gly Ile Glu Phe Met Lys Lys Leu Gly Ile Lys
                85                  90                  95

Tyr Tyr Cys Phe His Asp Thr Asp Ile Val Pro Glu Asp Gln Glu Asp
            100                 105                 110

Ile Asn Val Thr Asn Ala Arg Leu Asp Glu Ile Thr Asp Tyr Ile Leu
        115                 120                 125

Glu Lys Thr Lys Gly Ser Asp Ile Lys Cys Leu Trp Thr Thr Cys Asn
    130                 135                 140

Met Phe Gly Asn Pro Arg Phe Met Asn Gly Ala Gly Ser Ser Asn Ser
145                 150                 155                 160

Ala Asp Val Phe Cys Phe Ala Ala Ala Gln Ala Lys Lys Gly Leu Glu
                165                 170                 175

Asn Ala Val Lys Leu Gly Ala Lys Gly Phe Val Phe Trp Gly Gly Arg
            180                 185                 190

Glu Gly Tyr Glu Thr Leu Leu Asn Thr Asp Met Lys Leu Glu Glu Glu

```
              195                 200                 205
Asn Ile Ala Thr Leu Phe Thr Met Cys Arg Asp Tyr Gly Arg Ser Ile
            210                 215                 220

Gly Phe Lys Gly Asp Phe Tyr Ile Glu Pro Lys Pro Lys Glu Pro Met
225                 230                 235                 240

Lys His Gln Tyr Asp Phe Asp Ala Ala Thr Ala Ile Gly Phe Leu Arg
                245                 250                 255

Lys Tyr Gly Leu Asp Lys Asp Phe Lys Leu Asn Ile Glu Ala Asn His
            260                 265                 270

Ala Thr Leu Ala Gly His Thr Phe Gln His Glu Leu Arg Val Ser Ala
        275                 280                 285

Ile Asn Gly Met Leu Gly Ser Val Asp Ala Asn Gln Gly Asp Thr Leu
    290                 295                 300

Leu Gly Trp Asp Thr Asp Gln Phe Pro Thr Asn Ile Tyr Asp Thr Thr
305                 310                 315                 320

Phe Ala Met Tyr Glu Ile Leu Lys Ala Gly Gly Leu Ser Gly Gly Leu
                325                 330                 335

Asn Phe Asp Ser Lys Asn Arg Arg Pro Ser Asn Thr Ala Glu Asp Met
            340                 345                 350

Phe Tyr Gly Phe Ile Ala Gly Met Asp Thr Phe Ala Leu Gly Leu Ile
        355                 360                 365

Lys Ala Ala Gln Ile Ile Glu Asp Gly Arg Ile Asp Glu Phe Ile Lys
    370                 375                 380

Glu Arg Tyr Ser Ser Tyr Ser Thr Gly Ile Gly Glu Lys Ile Arg Asn
385                 390                 395                 400

Lys Ser Val Thr Leu Glu Glu Cys Ala Glu Tyr Ala Ala Lys Leu Lys
                405                 410                 415

Lys Pro Glu Leu Pro Glu Ser Gly Arg Gln Tyr Leu Glu Thr Val
            420                 425                 430

Val Asn Asn Ile Leu Phe Asn Ser Lys Leu
        435                 440

<210> SEQ ID NO 39
<211> LENGTH: 439
<212> TYPE: PRT
<213> ORGANISM: Lachnospiraceae bacterium

<400> SEQUENCE: 39

Met Lys Glu Phe Phe Pro Gly Ile Ser Pro Val Lys Phe Glu Gly Lys
1               5                   10                  15

Asp Ser Lys Asn Pro Leu Ser Phe Lys Tyr Tyr Asp Ala Lys Arg Val
            20                  25                  30

Ile Met Gly Lys Thr Met Glu Glu His Leu Ser Phe Ala Met Ala Trp
        35                  40                  45

Trp His Asn Leu Cys Ala Cys Gly Val Asp Met Phe Gly Gln Gly Thr
    50                  55                  60

Ile Asp Lys Ser Phe Gly Ala Leu Pro Gly Thr Met Glu His Ala Lys
65                  70                  75                  80

Ala Lys Val Asp Ala Gly Ile Glu Phe Met Gln Lys Leu Gly Ile Lys
                85                  90                  95

Tyr Tyr Cys Phe His Asp Thr Asp Ile Val Pro Glu Asp Gln Glu Asp
            100                 105                 110

Ile Asn Val Thr Asn Ala Arg Leu Asp Glu Ile Thr Asp Tyr Ile Leu
        115                 120                 125
```

```
Glu Lys Thr Lys Gly Thr Asp Ile Lys Cys Leu Trp Thr Thr Cys Asn
    130                 135                 140

Met Phe Ser Asn Pro Arg Phe Met Asn Gly Ala Gly Ser Ser Asn Ser
145                 150                 155                 160

Ala Asp Val Phe Cys Phe Ala Ala Gln Ala Lys Lys Gly Leu Glu
                165                 170                 175

Asn Ala Val Lys Leu Gly Ala Lys Gly Phe Val Phe Trp Gly Gly Arg
                180                 185                 190

Glu Gly Tyr Glu Thr Leu Leu Asn Thr Asp Met Lys Leu Glu Glu Glu
            195                 200                 205

Asn Ile Ala Thr Leu Phe Thr Met Cys Arg Asp Tyr Gly Arg Ser Ile
    210                 215                 220

Gly Phe Met Gly Asp Phe Tyr Ile Glu Pro Lys Pro Lys Glu Pro Met
225                 230                 235                 240

Lys His Gln Tyr Asp Phe Asp Ala Ala Thr Ala Ile Gly Phe Leu Arg
                245                 250                 255

Lys Tyr Gly Leu Glu Lys Asp Phe Lys Met Asn Ile Glu Ala Asn His
            260                 265                 270

Ala Thr Leu Ala Gly His Thr Phe Gln His Glu Leu Arg Val Cys Ala
    275                 280                 285

Val Asn Gly Met Ile Gly Ser Val Asp Ala Asn Gln Gly Asp Thr Leu
290                 295                 300

Leu Gly Trp Asp Thr Asp Gln Phe Pro Thr Asn Val Tyr Asp Thr Thr
305                 310                 315                 320

Leu Ala Met Tyr Glu Ile Leu Lys Ala Gly Gly Leu Arg Gly Gly Leu
                325                 330                 335

Asn Phe Asp Ser Lys Asn Arg Arg Pro Ser Asn Thr Ala Asp Asp Met
            340                 345                 350

Phe Tyr Gly Phe Ile Ala Gly Met Asp Ala Phe Ala Leu Gly Leu Ile
    355                 360                 365

Lys Ala Ala Glu Ile Ile Glu Asp Gly Arg Ile Asp Glu Phe Val Lys
370                 375                 380

Glu Arg Tyr Ser Ser Tyr Asn Ser Gly Ile Gly Glu Lys Ile Arg Asn
385                 390                 395                 400

Arg Ala Val Thr Leu Val Glu Cys Ala Glu Tyr Ala Ala Lys Leu Lys
                405                 410                 415

Lys Pro Glu Leu Pro Asp Ser Gly Lys Gln Glu Tyr Leu Glu Ser Val
            420                 425                 430

Val Asn Asn Ile Leu Phe Gly
    435

<210> SEQ ID NO 40
<211> LENGTH: 443
<212> TYPE: PRT
<213> ORGANISM: uncultured bacterium

<400> SEQUENCE: 40

Met Ser Val Val Leu Gly Asp Lys Glu Tyr Phe Pro Gly Val Gly Lys
1               5                   10                  15

Ile Ala Tyr Glu Gly Pro Glu Ser Asp Asn Pro Leu Ser Phe Lys Trp
                20                  25                  30

Tyr Asp Glu Asn Arg Val Val Ala Gly Lys Thr Leu Lys Asp His Phe
            35                  40                  45

Lys Phe Ala Val Cys Tyr Trp His Thr Phe Cys Gly Ala Gly His Asp
    50                  55                  60
```

```
Ser Phe Gly Pro Gly Pro Phe Val Phe Pro Trp Gly Ala Gly Ser Asp
 65                  70                  75                  80

Ala Leu Ser Arg Ala Lys Met Lys Ala Asp Ala Ala Phe Glu Phe Ile
                 85                  90                  95

Thr Lys Leu Gly Val Pro Tyr Tyr Cys Phe His Asp Ile Asp Leu Ile
            100                 105                 110

Glu Glu Gly Ser Ser Arg Ala Glu Thr Ala Lys Arg Val Met Asp Ile
        115                 120                 125

Val Glu Tyr Ala Lys Gln Lys Gln Ala Ala Ser Gly Val Lys Leu Leu
130                 135                 140

Trp Gly Thr Ala Asn Leu Phe Ser Asn Pro Arg Tyr Ile Asn Gly Ala
145                 150                 155                 160

Ser Thr Asn Pro Asp Phe Ala Val Val Ala His Ala Gly Ala Gln Leu
                165                 170                 175

Lys Asp Ala Leu Asp Ala Thr Ile Ala Leu Gly Gly Glu Asn Tyr Val
            180                 185                 190

Phe Trp Gly Gly Arg Glu Gly Tyr Met Ser Pro Leu Asn Thr Asp Met
        195                 200                 205

Lys Arg Glu Val Glu Arg Phe Ala Arg Phe Leu Thr Met Ala Arg Asp
210                 215                 220

Tyr Ala Arg Gly Gln Gly Phe Lys Gly Val Phe Phe Ile Glu Pro Lys
225                 230                 235                 240

Pro Met Glu Pro Ser Lys His Gln Tyr Asp Phe Asp Cys Ala Thr Val
                245                 250                 255

Ile Gly Phe Leu Arg Gln Tyr Gly Leu Asp Lys Asp Phe Lys Leu Asn
            260                 265                 270

Ile Glu Thr Asn His Ala Thr Leu Ala Gly His Thr Met Glu His Glu
        275                 280                 285

Met Gln Val Ala Ala Asp Ala Gly Met Leu Gly Ser Ile Asp Ala Asn
290                 295                 300

Arg Gly Asp Tyr Gln Asn Ala Trp Asp Thr Asp Gln Phe Pro Asn Asn
305                 310                 315                 320

Ile Asn Glu Thr Thr Glu Met Met Leu Val Leu Leu Arg Ser Gly Gly
                325                 330                 335

Phe Gln Gly Gly Gly Val Asn Phe Asp Ala Lys Arg Arg Arg Asn Ser
            340                 345                 350

Thr Asp Pro Asn Asp Thr Phe His Gly His Ile Gly Met Asp Thr
        355                 360                 365

Phe Ala Arg Ser Leu Ile Ile Ala Gly Asp Ile Leu Glu Lys Ser Pro
370                 375                 380

Ile Glu Lys Met Arg Lys Glu Arg Tyr Ala Ser Phe Asp Ala Gly Lys
385                 390                 395                 400

Gly Ala Glu Phe Glu Ala Gly Lys Leu Ser Leu Val Gln Leu Ala Glu
                405                 410                 415

Leu Gly Asn Lys Gly Gly Glu Pro Thr Gln Lys Ser Gly Arg Gln Glu
            420                 425                 430

Leu Tyr Glu Asn Ile Met Asn Arg Trp Ile Arg
        435                 440

<210> SEQ ID NO 41
<211> LENGTH: 442
<212> TYPE: PRT
<213> ORGANISM: uncultured bacterium
```

<400> SEQUENCE: 41

```
Met Lys Leu Thr Val Gly Asp Lys Glu Tyr Phe Lys Gly Ile Lys Pro
1               5                   10                  15

Ile Lys Phe Glu Gly Lys Asp Ser Asp Asn Pro Leu Ala Phe Lys Tyr
            20                  25                  30

Tyr Asn Pro Ser Gln Lys Val Gly Lys Thr Met Glu Glu His Phe
        35                  40                  45

Arg Phe Ala Ile Ala Tyr Trp His Thr Phe Cys Gly Thr Gly Gly Asp
    50                  55                  60

Pro Phe Gly Pro Gly Thr Lys Thr Phe Pro Trp Leu Gln Asn Ser Asp
65                  70                  75                  80

Ala Val Gln Arg Ala Tyr Asp Lys Met Asp Ala Ala Phe Glu Phe Ile
                85                  90                  95

Thr Lys Ile Gly Ala Pro Phe Tyr Cys Phe His Asp Tyr Asp Leu Val
            100                 105                 110

Asp Glu Gly Pro Thr Leu Lys Glu Ser Glu Ser Arg Leu Gln Lys Val
            115                 120                 125

Val Asp Tyr Ala Lys Lys Lys Gln Lys Ala Ser Gly Val Lys Leu Leu
    130                 135                 140

Trp Gly Thr Ala Asn Leu Phe Ser His Pro Arg Tyr Met Asn Gly Ala
145                 150                 155                 160

Ala Thr Asn Pro Asp Phe Asp Val Val Cys Tyr Ala Ala Ser Gln Val
                165                 170                 175

Lys Asn Ala Leu Asp Ala Thr Ile Ala Leu Gly Gly Ala Asn Tyr Val
            180                 185                 190

Phe Trp Gly Gly Arg Glu Gly Tyr Met Ser Leu Leu Asn Thr Asn Met
    195                 200                 205

Lys Arg Glu Gln Glu His Met Ala Lys Phe Leu His Met Ala Lys Asp
210                 215                 220

Tyr Ala Arg Ala Asn Gly Phe Lys Gly Thr Phe Phe Ile Glu Pro Lys
225                 230                 235                 240

Pro Met Glu Pro Ser Lys His Gln Tyr Asp Phe Asp Ser Ala Thr Val
                245                 250                 255

Ile Gly Phe Leu Arg Gln Phe Asp Leu Leu Gly Asp Phe Lys Leu Asn
            260                 265                 270

Ile Glu Val Asn His Ala Thr Leu Ala His His Thr Phe Gln His Glu
            275                 280                 285

Leu Gln Val Ala Ala Asp Ala Gly Ala Leu Gly Ser Ile Asp Ala Asn
    290                 295                 300

Arg Gly Asp Tyr Gln Asn Gly Trp Asp Thr Asp Gln Phe Pro Asn Asn
305                 310                 315                 320

Leu Tyr Glu Leu Ala Glu Ser Met Leu Val Ile Leu Glu Ala Gly Gly
                325                 330                 335

Phe Lys Ser Gly Gly Val Asn Phe Asp Ala Lys Thr Arg Arg Asn Ser
            340                 345                 350

Thr Asp Leu Val Asp Ile Phe His Ala His Ile Gly Met Asp Thr
            355                 360                 365

Phe Ala Arg Ser Leu Leu Ile Ala Gln Ala Val Leu Asp Asn Gly Glu
    370                 375                 380

Tyr Thr Lys Ile Arg Lys Asp Arg Tyr Ser Ser Phe Asp Ser Gly Lys
385                 390                 395                 400

Gly Lys Gln Phe Asp Gln Gly Lys Leu Ser Leu Glu Asp Leu Arg Asn
                405                 410                 415
```

Leu Ala His Lys Ala Gly Glu Pro Lys Gln Leu Ser Gly Lys Gln Glu
                420                 425                 430

Tyr Ile Glu Asn Leu Ile Ser Arg Phe Ile
                435                 440

<210> SEQ ID NO 42
<211> LENGTH: 387
<212> TYPE: PRT
<213> ORGANISM: Thermus thermophilus

<400> SEQUENCE: 42

Met Tyr Glu Pro Lys Pro Glu His Arg Phe Thr Phe Gly Leu Trp Thr
1               5                   10                  15

Val Gly Asn Val Gly Arg Asp Pro Phe Gly Asp Ala Val Arg Glu Arg
                20                  25                  30

Leu Asp Pro Val Tyr Val His Lys Leu Ala Glu Leu Gly Ala Tyr
            35                  40                  45

Gly Val Asn Leu His Asp Glu Asp Leu Ile Pro Arg Gly Thr Pro Pro
        50                  55                  60

Gln Glu Arg Asp Gln Ile Val Arg Arg Phe Lys Lys Ala Leu Asp Glu
65                  70                  75                  80

Thr Gly Leu Lys Val Pro Met Val Thr Ala Asn Leu Phe Ser Asp Pro
                85                  90                  95

Ala Phe Lys Asp Gly Ala Phe Thr Ser Pro Asp Pro Trp Val Arg Ala
                100                 105                 110

Tyr Ala Leu Arg Lys Ser Leu Glu Thr Met Asp Leu Gly Ala Glu Leu
            115                 120                 125

Gly Ala Glu Ile Tyr Val Val Trp Pro Gly Arg Glu Gly Ala Glu Val
        130                 135                 140

Glu Ala Thr Gly Lys Ala Arg Lys Val Trp Asp Trp Val Arg Glu Ala
145                 150                 155                 160

Leu Asn Phe Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Phe Ile His Thr Leu Asp Arg Pro
        195                 200                 205

Glu Arg Phe Gly Leu Asn Pro Glu Phe Ala His Glu Thr Met Ala Gly
210                 215                 220

Leu Asn Phe Val His Ala Val Ala Gln Ala Leu Asp Ala Gly Lys Leu
225                 230                 235                 240

Phe His Ile Asp Leu Asn Asp Gln Arg Met Ser Arg Phe Asp Gln Asp
                245                 250                 255

Leu Arg Phe Gly Ser Glu Asn Leu Lys Ala Ala Phe Phe Leu Val Asp
            260                 265                 270

Leu Leu Glu Ser Ser Gly Tyr Gln Gly Pro Arg His Phe Asp Ala His
        275                 280                 285

Ala Leu Arg Thr Glu Asp Glu Glu Gly Val Trp Ala Phe Ala Arg Gly
        290                 295                 300

Cys Met Arg Thr Tyr Leu Ile Leu Lys Glu Ala Glu Ala Phe Arg
305                 310                 315                 320

Glu Asp Pro Glu Val Lys Glu Leu Leu Ala Ala Tyr Tyr Gln Glu Asp
                325                 330                 335

Pro Ala Ala Leu Ala Leu Leu Gly Pro Tyr Ser Arg Glu Lys Ala Glu

```
                    340             345             350
Ala Leu Lys Arg Ala Glu Leu Pro Leu Glu Ala Lys Arg Arg Gly
            355             360             365

Tyr Ala Leu Glu Arg Leu Asp Gln Leu Ala Val Glu Tyr Leu Leu Gly
370             375             380

Val Arg Gly
385

<210> SEQ ID NO 43
<211> LENGTH: 440
<212> TYPE: PRT
<213> ORGANISM: Escherichia coli

<400> SEQUENCE: 43

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320
```

Val Met Tyr Glu Ile Leu Lys Ala Gly Gly Phe Thr Thr Gly Gly Leu
            325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
            355                 360                 365

Ile Ala Ala Arg Met Ile Glu Asp Gly Glu Leu Asp Lys Arg Ile Ala
            370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
            405                 410                 415

Leu Ser Pro Val His Gln Ser Gly Arg Gln Glu Gln Leu Glu Asn Leu
            420                 425                 430

Val Asn His Tyr Leu Phe Asp Lys
            435                 440

<210> SEQ ID NO 44
<211> LENGTH: 600
<212> TYPE: PRT
<213> ORGANISM: Saccharomyces cerevisiae

<400> SEQUENCE: 44

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
            35                  40                  45

Thr Val Glu Phe Glu Lys Asp Leu Pro His Tyr His Thr Lys Lys Gly
            50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
            85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
            115                 120                 125

Lys Pro Glu Lys Asp Leu Leu His Tyr Val Ser Ser Val Ala Phe Ala
130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
            165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
            195                 200                 205

Leu Val Ser Asn Phe Leu Thr Ser Ile Leu Val Gly His Leu Val Glu
            210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
            245                 250                 255

Asp Lys Thr Ile Arg Gln Lys Leu Met Arg Ala Pro Met Lys Asn Leu
              260                 265                 270

Ile Ala Gly Thr Ile Cys Lys Tyr Phe Ile Glu Lys Tyr Gly Phe Asn
              275                 280                 285

Thr Asn Cys Lys Val Ser Pro Met Thr Gly Asp Asn Leu Ala Thr Ile
              290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
              325                 330                 335

Tyr His Leu Phe Ile His Pro Thr Leu Pro Asn His Tyr Met Gly Met
              340                 345                 350

Ile Cys Tyr Cys Asn Gly Ser Leu Ala Arg Glu Arg Ile Arg Asp Glu
              355                 360                 365

Leu Asn Lys Glu Arg Glu Asn Asn Tyr Glu Lys Thr Asn Asp Trp Thr
              370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
              405                 410                 415

Ile Asn Lys Arg Val Ile Phe Asn Pro Lys Thr Gly Met Ile Glu Arg
              420                 425                 430

Glu Val Ala Lys Phe Lys Asp Lys Arg His Asp Ala Lys Asn Ile Val
              435                 440                 445

Glu Ser Gln Ala Leu Ser Cys Arg Val Arg Ile Ser Pro Leu Leu Ser
              450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
              485                 490                 495

Pro Glu Arg Thr Phe Phe Val Gly Gly Ala Ser Lys Asn Asp Ala Ile
              500                 505                 510

Val Lys Lys Phe Ala Gln Val Ile Gly Ala Thr Lys Gly Asn Phe Arg
              515                 520                 525

Leu Glu Thr Pro Asn Ser Cys Ala Leu Gly Gly Cys Tyr Lys Ala Met
              530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
              565                 570                 575

Val Asp Asn Glu Asn Trp Asp Arg Tyr Asn Ser Lys Ile Val Pro Leu
              580                 585                 590

Ser Glu Leu Glu Lys Thr Leu Ile
              595                 600

<210> SEQ ID NO 45
<211> LENGTH: 623
<212> TYPE: PRT
<213> ORGANISM: Pichia stipitis

<400> SEQUENCE: 45

Met Thr Thr Thr Pro Phe Asp Ala Pro Asp Lys Leu Phe Leu Gly Phe
1               5                   10                  15

Asp Leu Ser Thr Gln Gln Leu Lys Ile Ile Val Thr Asp Glu Asn Leu

```
            20                  25                  30
Ala Ala Leu Lys Thr Tyr Asn Val Glu Phe Asp Ser Ile Asn Ser Ser
        35                  40                  45
Val Gln Lys Gly Val Ile Ala Ile Asn Asp Glu Ile Ser Lys Gly Ala
    50                  55                  60
Ile Ile Ser Pro Val Tyr Met Trp Leu Asp Ala Leu Asp His Val Phe
65                  70                  75                  80
Glu Asp Met Lys Lys Asp Gly Phe Pro Phe Asn Lys Val Val Gly Ile
                85                  90                  95
Ser Gly Ser Cys Gln Gln His Gly Ser Val Tyr Trp Ser Arg Thr Ala
            100                 105                 110
Glu Lys Val Leu Ser Glu Leu Asp Ala Glu Ser Ser Leu Ser Ser Gln
        115                 120                 125
Met Arg Ser Ala Phe Thr Phe Lys His Ala Pro Asn Trp Gln Asp His
    130                 135                 140
Ser Thr Gly Lys Glu Leu Glu Glu Phe Glu Arg Val Ile Gly Ala Asp
145                 150                 155                 160
Ala Leu Ala Asp Ile Ser Gly Ser Arg Ala His Tyr Arg Phe Thr Gly
                165                 170                 175
Leu Gln Ile Arg Lys Leu Ser Thr Arg Phe Lys Pro Glu Lys Tyr Asn
            180                 185                 190
Arg Thr Ala Arg Ile Ser Leu Val Ser Ser Phe Val Ala Ser Val Leu
        195                 200                 205
Leu Gly Arg Ile Thr Ser Ile Glu Glu Ala Asp Ala Cys Gly Met Asn
    210                 215                 220
Leu Tyr Asp Ile Glu Lys Arg Glu Phe Asn Glu Glu Leu Leu Ala Ile
225                 230                 235                 240
Ala Ala Gly Val His Pro Glu Leu Asp Gly Val Glu Gln Asp Gly Glu
                245                 250                 255
Ile Tyr Arg Ala Gly Ile Asn Glu Leu Lys Arg Lys Leu Gly Pro Val
            260                 265                 270
Lys Pro Ile Thr Tyr Glu Ser Glu Gly Asp Ile Ala Ser Tyr Phe Val
        275                 280                 285
Thr Arg Tyr Gly Phe Asn Pro Asp Cys Lys Ile Tyr Ser Phe Thr Gly
    290                 295                 300
Asp Asn Leu Ala Thr Ile Ile Ser Leu Pro Leu Ala Pro Asn Asp Ala
305                 310                 315                 320
Leu Ile Ser Leu Gly Thr Ser Thr Thr Val Leu Ile Ile Thr Lys Asn
                325                 330                 335
Tyr Ala Pro Ser Ser Gln Tyr His Leu Phe Lys His Pro Thr Met Pro
            340                 345                 350
Asp His Tyr Met Gly Met Ile Cys Tyr Cys Asn Gly Ser Leu Ala Arg
        355                 360                 365
Glu Lys Val Arg Asp Glu Val Asn Glu Lys Phe Asn Val Glu Asp Lys
    370                 375                 380
Lys Ser Trp Asp Lys Phe Asn Glu Ile Leu Asp Lys Ser Thr Asp Phe
385                 390                 395                 400
Asn Asn Lys Leu Gly Ile Tyr Phe Pro Leu Gly Glu Ile Val Pro Asn
                405                 410                 415
Ala Ala Ala Gln Ile Lys Arg Ser Val Leu Asn Ser Lys Asn Glu Ile
            420                 425                 430
Val Asp Val Glu Leu Gly Asp Lys Asn Trp Gln Pro Glu Asp Asp Val
        435                 440                 445
```

```
Ser Ser Ile Val Glu Ser Gln Thr Leu Ser Cys Arg Leu Arg Thr Gly
    450                 455                 460

Pro Met Leu Ser Lys Ser Gly Asp Ser Ala Ser Ser Ser Ala Ser
465                 470                 475                 480

Pro Gln Pro Glu Gly Asp Gly Thr Asp Leu His Lys Val Tyr Gln Asp
                485                 490                 495

Leu Val Lys Lys Phe Gly Asp Leu Tyr Thr Asp Gly Lys Lys Gln Thr
            500                 505                 510

Phe Glu Ser Leu Thr Ala Arg Pro Asn Arg Cys Tyr Tyr Val Gly Gly
        515                 520                 525

Ala Ser Asn Asn Gly Ser Ile Ile Arg Lys Met Gly Ser Ile Leu Ala
    530                 535                 540

Pro Val Asn Gly Asn Tyr Lys Val Asp Ile Pro Asn Ala Cys Ala Leu
545                 550                 555                 560

Gly Gly Ala Tyr Lys Ala Ser Trp Ser Tyr Glu Cys Glu Ala Lys Lys
                565                 570                 575

Glu Trp Ile Gly Tyr Asp Gln Tyr Ile Asn Arg Leu Phe Glu Val Ser
            580                 585                 590

Asp Glu Met Asn Ser Phe Glu Val Lys Asp Lys Trp Leu Glu Tyr Ala
        595                 600                 605

Asn Gly Val Gly Met Leu Ala Lys Met Glu Ser Glu Leu Lys His
    610                 615                 620

<210> SEQ ID NO 46
<211> LENGTH: 575
<212> TYPE: PRT
<213> ORGANISM: Hypocrea jecorina

<400> SEQUENCE: 46

Met Ser Glu Glu Lys Gly Pro Leu Tyr Leu Gly Phe Asp Leu Ser Thr
1               5                   10                  15

Gln Gln Leu Lys Ala Ile Val Val Asn Ser Asn Leu Lys Ser Ile Ala
            20                  25                  30

Glu Ala Lys Val Asp Phe Asp Gln Asp Phe Gly Pro Gln Tyr Gly Ile
        35                  40                  45

Gln Lys Gly Val His Val Arg Glu Ser Thr Gly Glu Val Phe Ala Pro
    50                  55                  60

Val Ala Leu Trp Leu Glu Ser Leu Asp Leu Val Leu Ser Arg Leu Ser
65                  70                  75                  80

Lys Ala Met His Pro Leu Pro Met Ser Arg Ile Arg Gly Val Ser Gly
                85                  90                  95

Ser Gly Gln Gln His Gly Ala Val Phe Trp Asn Ala Ser Ala Glu Glu
            100                 105                 110

Leu Leu Gly Gly Leu Asp Ala Ala Lys Gly Ser Leu Val Glu Gln Leu
        115                 120                 125

Arg Gly Ala Leu Ala His Glu Phe Ala Pro Asn Trp Gln Asp His Ser
    130                 135                 140

Thr Gln Glu Glu Leu Val Ala Phe Asp Ala Glu Leu Gly Asp Arg Glu
145                 150                 155                 160

Lys Leu Ala Glu Val Thr Gly Ser Gly Ala His His Arg Phe Thr Gly
                165                 170                 175

Leu Gln Ile Met Arg Ile Arg Arg Val Leu Pro Gln Val Tyr Ala Asn
            180                 185                 190

Ala Lys Arg Ile Ser Leu Val Ser Ser Trp Leu Ala Ser Val Leu Met
```

195                 200                 205
Gly Ser Ile Ala Pro Leu Asp Val Ser Asp Val Cys Gly Met Asn Leu
210                 215                 220

Trp Asp Ile Pro Asn Gln Ala Trp Ser Glu Lys Leu Leu Ala Leu Ser
225                 230                 235                 240

Gly Gly Gly Gly Leu Asp Gly Ala Ala Asn Leu Arg Arg Lys Leu Gly
                245                 250                 255

Glu Pro Arg Met Asp Gly Gly Ser Met Gly Ser Ile Ser Arg Tyr
            260                 265                 270

Tyr Val Ser Lys Tyr Gly Phe Ser Pro Glu Cys Gln Ile Thr Pro Phe
        275                 280                 285

Thr Gly Asp Asn Pro Ala Thr Ile Leu Ala Leu Pro Leu Arg Pro Leu
290                 295                 300

Asp Ala Ile Val Ser Leu Gly Thr Ser Thr Thr Phe Leu Met Asn Thr
305                 310                 315                 320

Pro Ala Tyr Lys Pro Asp Gly Ser Tyr His Phe Phe Asn His Pro Thr
                325                 330                 335

Thr Pro Gly Asn Tyr Met Phe Met Leu Cys Tyr Lys Asn Gly Gly Leu
            340                 345                 350

Ala Arg Glu Lys Val Arg Asp Thr Leu Pro Lys Pro Glu Gly Gly Ala
        355                 360                 365

Thr Gly Trp Glu Thr Phe Asn Glu Ala Ile Met Ala Thr Lys Pro Leu
370                 375                 380

Gly Ile Glu Ser Asp Gly Asp Arg Ala Lys Leu Gly Leu Tyr Phe Tyr
385                 390                 395                 400

Leu Arg Glu Thr Val Pro Asn Ile Arg Ala Gly Thr Trp Arg Phe Thr
                405                 410                 415

Cys Arg Gln Asp Gly Ser Asp Leu Gln Glu Ala Arg Glu Ala Trp Pro
            420                 425                 430

Lys Glu Ala Asp Ala Arg Ala Ile Val Glu Ser Gln Ala Leu Ser Met
        435                 440                 445

Arg Leu Arg Ser Gln Lys Leu Val His Ser Pro Arg Asp Gly Leu Pro
450                 455                 460

Ala Gln Pro Arg Arg Ile Tyr Val Val Gly Gly Ser Leu Asn Pro
465                 470                 475                 480

Ala Ile Thr Arg Val Leu Gly Glu Val Leu Gly Gly Ala Asp Gly Val
                485                 490                 495

Tyr Lys Leu Asp Val Gly Gly Asn Ala Cys Ala Leu Gly Gly Ala Tyr
            500                 505                 510

Lys Ala Leu Trp Ala Leu Glu Arg Lys Asp Gly Glu Thr Phe Asp Asp
        515                 520                 525

Leu Ile Gly Gly Arg Trp Thr Glu Glu Gly Ser Ile Asp Lys Val Asp
530                 535                 540

Val Gly Tyr Arg Glu Gly Thr Tyr Glu Arg Tyr Gly Lys Val Leu Gly
545                 550                 555                 560

Ala Phe Glu Glu Met Glu Arg Arg Leu Leu Ala Glu Glu His
                565                 570                 575

<210> SEQ ID NO 47
<211> LENGTH: 335
<212> TYPE: PRT
<213> ORGANISM: Saccharomyces cerevisiae

<400> SEQUENCE: 47

```
Met Ser Glu Pro Ala Gln Lys Gln Lys Val Ala Asn Asn Ser Leu
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Asn Pro
            35                  40                  45

Ser Leu Ile Leu Ala Ala Lys Gln Pro Thr Tyr Ala Lys Leu Ile
50                  55                  60

Asp Val Ala Val Glu Tyr Gly Lys Lys His Gly Lys Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
                100                 105                 110

Leu Ser Phe Asp Thr Gln Ala Thr Ile Glu Lys Ala Arg His Ile Ile
                115                 120                 125

Lys Leu Phe Glu Gln Glu Gly Val Ser Lys Arg Val Leu Ile Lys
                130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
                180                 185                 190

Gly Arg Ile Leu Asp Trp Tyr Lys Ser Ser Thr Gly Lys Asp Tyr Lys
                195                 200                 205

Gly Glu Ala Asp Pro Gly Val Ile Ser Val Lys Lys Ile Tyr Asn Tyr
                210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
                260                 265                 270

Arg Val Leu Asp Pro Val Ser Ala Lys Lys Glu Ala Gly Asp Lys Ile
                275                 280                 285

Ser Tyr Ile Ser Asp Glu Ser Lys Phe Arg Phe Asp Leu Asn Glu Asp
                290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335

<210> SEQ ID NO 48
<211> LENGTH: 333
<212> TYPE: PRT
<213> ORGANISM: Saccharomyces cerevisiae

<400> SEQUENCE: 48

Met Ser Glu Pro Ser Lys Lys Gln Lys Val Ala Thr Ser Ser Leu
1               5                   10                  15

Glu Gln Leu Lys Lys Ala Gly Thr His Val Val Ala Asp Ser Gly Asp
                20                  25                  30

Phe Glu Ala Ile Ser Lys Tyr Glu Pro Gln Asp Ser Thr Thr Asn Pro
            35                  40                  45
```

Ser Leu Ile Leu Ala Ala Ser Lys Leu Glu Lys Tyr Ala Arg Phe Ile
    50                  55                  60

Asp Ala Ala Val Glu Tyr Gly Arg Lys His Gly Lys Thr Asp His Glu
65                  70                  75                  80

Lys Ile Glu Asn Ala Met Asp Lys Ile Leu Val Glu Phe Gly Thr Gln
                85                  90                  95

Ile Leu Lys Val Val Pro Gly Arg Val Ser Thr Glu Val Asp Ala Arg
            100                 105                 110

Leu Ser Phe Asp Lys Lys Ala Thr Val Lys Lys Ala Leu His Ile Ile
            115                 120                 125

Lys Leu Tyr Lys Asp Ala Gly Val Pro Lys Glu Arg Val Leu Ile Lys
        130                 135                 140

Ile Ala Ser Thr Trp Glu Gly Ile Gln Ala Ala Arg Glu Leu Glu Val
145                 150                 155                 160

Lys His Gly Ile His Cys Asn Met Thr Leu Leu Phe Ser Phe Thr Gln
                165                 170                 175

Ala Val Ala Cys Ala Glu Ala Asn Val Thr Leu Ile Ser Pro Phe Val
            180                 185                 190

Gly Arg Ile Met Asp Phe Tyr Lys Ala Leu Ser Gly Lys Asp Tyr Thr
        195                 200                 205

Ala Glu Thr Asp Pro Gly Val Leu Ser Val Lys Lys Ile Tyr Ser Tyr
210                 215                 220

Tyr Lys Arg His Gly Tyr Ala Thr Glu Val Met Ala Ala Ser Phe Arg
225                 230                 235                 240

Asn Leu Asp Glu Leu Lys Ala Leu Ala Gly Ile Asp Asn Met Thr Leu
                245                 250                 255

Pro Leu Asn Leu Leu Glu Gln Leu Tyr Glu Ser Thr Asp Pro Ile Glu
            260                 265                 270

Asn Lys Leu Asn Ser Glu Ser Ala Lys Glu Glu Gly Val Glu Lys Val
        275                 280                 285

Ser Phe Ile Asn Asp Glu Pro His Phe Arg Tyr Val Leu Asn Glu Asp
290                 295                 300

Gln Met Ala Thr Glu Lys Leu Ser Asp Gly Ile Arg Lys Phe Ser Ala
305                 310                 315                 320

Asp Ile Glu Ala Leu Tyr Lys Leu Val Glu Glu Lys Met
                325                 330

<210> SEQ ID NO 49
<211> LENGTH: 323
<212> TYPE: PRT
<213> ORGANISM: Scheffersomyces stipitis

<400> SEQUENCE: 49

Met Ser Ser Asn Ser Leu Glu Gln Leu Lys Ala Thr Gly Thr Val Ile
1               5                   10                  15

Val Thr Asp Thr Gly Glu Phe Asp Ser Ile Ala Lys Tyr Thr Pro Gln
            20                  25                  30

Asp Ala Thr Thr Asn Pro Ser Leu Ile Leu Ala Ala Lys Lys Pro
        35                  40                  45

Glu Tyr Ala Lys Val Ile Asp Val Ala Ile Glu Tyr Ala Lys Asp Lys
    50                  55                  60

Gly Ser Ser Lys Lys Glu Lys Ala Glu Ile Ala Leu Asp Arg Leu Leu
65                  70                  75                  80

Ile Glu Phe Gly Lys Asn Ile Leu Ala Ile Val Pro Gly Arg Val Ser

```
                    85                  90                  95
Thr Glu Val Asp Ala Arg Leu Ser Phe Asp Lys Glu Ala Thr Ile Lys
                100                 105                 110
Lys Ala Leu Glu Leu Ile Ala Leu Tyr Glu Ser Gln Gly Ile Ser Lys
            115                 120                 125
Asp Arg Ile Leu Ile Lys Ile Ala Ser Thr Trp Glu Gly Ile Gln Ala
        130                 135                 140
Ala Arg Glu Leu Glu Ala Lys His Gly Ile His Cys Asn Leu Thr Leu
145                 150                 155                 160
Leu Phe Ser Phe Val Gln Ala Val Ala Cys Glu Ala Lys Val Thr
                165                 170                 175
Leu Ile Ser Pro Phe Val Gly Arg Ile Leu Asp Trp Tyr Lys Ala Ser
                180                 185                 190
Thr Gly Lys Thr Tyr Glu Gly Asp Glu Asp Pro Gly Val Ile Ser Val
            195                 200                 205
Arg Ala Ile Tyr Asn Tyr Tyr Lys Lys Tyr Gly Tyr Lys Thr Ile Val
        210                 215                 220
Met Gly Ala Ser Phe Arg Asn Thr Gly Glu Ile Lys Ala Leu Ala Gly
225                 230                 235                 240
Cys Asp Tyr Leu Thr Val Ala Pro Lys Leu Leu Glu Glu Leu Leu Asn
                245                 250                 255
Ser Thr Glu Pro Val Pro Gln Val Leu Asp Ala Ala Ser Ala Ser Ala
                260                 265                 270
Thr Asp Val Glu Lys Val Ser Tyr Val Asp Asp Glu Ala Thr Phe Arg
            275                 280                 285
Tyr Leu Phe Asn Glu Asp Ala Met Ala Thr Glu Lys Leu Ala Gln Gly
        290                 295                 300
Ile Arg Ala Phe Gly Lys Asp Ala Val Thr Leu Leu Glu Gln Leu Glu
305                 310                 315                 320
Ala Arg Phe

<210> SEQ ID NO 50
<211> LENGTH: 680
<212> TYPE: PRT
<213> ORGANISM: Saccharomyces cerevisiae

<400> SEQUENCE: 50

Met Thr Gln Phe Thr Asp Ile Asp Lys Leu Ala Val Ser Thr Ile Arg
1               5                   10                  15
Ile Leu Ala Val Asp Thr Val Ser Lys Ala Asn Ser Gly His Pro Gly
            20                  25                  30
Ala Pro Leu Gly Met Ala Pro Ala Ala His Val Leu Trp Ser Gln Met
        35                  40                  45
Arg Met Asn Pro Thr Asn Pro Asp Trp Ile Asn Arg Asp Arg Phe Val
    50                  55                  60
Leu Ser Asn Gly His Ala Val Ala Leu Leu Tyr Ser Met Leu His Leu
65                  70                  75                  80
Thr Gly Tyr Asp Leu Ser Ile Glu Asp Leu Lys Gln Phe Arg Gln Leu
                85                  90                  95
Gly Ser Arg Thr Pro Gly His Pro Glu Phe Glu Leu Pro Gly Val Glu
                100                 105                 110
Val Thr Thr Gly Pro Leu Gly Gln Gly Ile Ser Asn Ala Val Gly Met
            115                 120                 125
Ala Met Ala Gln Ala Asn Leu Ala Ala Thr Tyr Asn Lys Pro Gly Phe
```

```
            130                 135                 140
Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
                195                 200                 205

Ala Tyr Gly Trp Glu Val Leu Tyr Val Glu Asn Gly Asn Glu Asp Leu
        210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Ile Gly Tyr Gly Ser Leu His
                245                 250                 255

Ala Gly Ser His Ser Val His Gly Ala Pro Leu Lys Ala Asp Asp Val
                260                 265                 270

Lys Gln Leu Lys Ser Lys Phe Gly Phe Asn Pro Asp Lys Ser Phe Val
            275                 280                 285

Val Pro Gln Glu Val Tyr Asp His Tyr Gln Lys Thr Ile Leu Lys Pro
        290                 295                 300

Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
                355                 360                 365

Val Tyr Asn Gln Leu Pro Glu Leu Ile Gly Gly Ser Ala Asp Leu Thr
        370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
                420                 425                 430

Ala Asn Tyr Lys Pro Tyr Gly Gly Thr Phe Leu Asn Phe Val Ser Tyr
            435                 440                 445

Ala Ala Gly Ala Val Arg Leu Ser Ala Leu Ser Gly His Pro Val Ile
        450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
                500                 505                 510

Asn Ser Leu Glu Ser Lys His Thr Pro Ser Ile Ile Ala Leu Ser Arg
            515                 520                 525

Gln Asn Leu Pro Gln Leu Glu Gly Ser Ser Ile Glu Ser Ala Ser Lys
        530                 535                 540

Gly Gly Tyr Val Leu Gln Asp Val Ala Asn Pro Asp Ile Ile Leu Val
545                 550                 555                 560
```

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
            610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680

<210> SEQ ID NO 51
<211> LENGTH: 681
<212> TYPE: PRT
<213> ORGANISM: Saccharomyces cerevisiae

<400> SEQUENCE: 51

Met Ala Gln Phe Ser Asp Ile Asp Lys Leu Ala Val Ser Thr Leu Arg
1               5                   10                  15

Leu Leu Ser Val Asp Gln Val Glu Ser Ala Gln Ser Gly His Pro Gly
                20                  25                  30

Ala Pro Leu Gly Leu Ala Pro Val Ala His Val Ile Phe Lys Gln Leu
            35                  40                  45

Arg Cys Asn Pro Asn Asn Glu His Trp Ile Asn Arg Asp Arg Phe Val
        50                  55                  60

Leu Ser Asn Gly His Ser Cys Ala Leu Leu Tyr Ser Met Leu His Leu
65                  70                  75                  80

Leu Gly Tyr Asp Tyr Ser Ile Glu Asp Leu Arg Gln Phe Arg Gln Val
                85                  90                  95

Asn Ser Arg Thr Pro Gly His Pro Glu Phe His Ser Ala Gly Val Glu
            100                 105                 110

Ile Thr Ser Gly Pro Leu Gly Gln Gly Ile Ser Asn Ala Val Gly Met
        115                 120                 125

Ala Ile Ala Gln Ala Asn Phe Ala Ala Thr Tyr Asn Glu Asp Gly Phe
    130                 135                 140

Pro Ile Ser Asp Ser Tyr Thr Phe Ala Ile Val Gly Asp Gly Cys Leu
145                 150                 155                 160

Gln Glu Gly Val Ser Ser Glu Thr Ser Ser Leu Ala Gly His Leu Gln
                165                 170                 175

Leu Gly Asn Leu Ile Thr Phe Tyr Asp Ser Asn Ser Ile Ser Ile Asp
            180                 185                 190

Gly Lys Thr Ser Tyr Ser Phe Asp Glu Asp Val Leu Lys Arg Tyr Glu
        195                 200                 205

Ala Tyr Gly Trp Glu Val Met Glu Val Asp Lys Gly Asp Asp Asp Met
    210                 215                 220

Glu Ser Ile Ser Ser Ala Leu Glu Lys Ala Lys Leu Ser Lys Asp Lys
225                 230                 235                 240

Pro Thr Ile Ile Lys Val Thr Thr Thr Ile Gly Phe Gly Ser Leu Gln

-continued

```
            245                 250                 255
Gln Gly Thr Ala Gly Val His Gly Ser Ala Leu Lys Ala Asp Asp Val
            260                 265                 270
Lys Gln Leu Lys Lys Arg Trp Gly Phe Asp Pro Asn Lys Ser Phe Val
            275                 280                 285
Val Pro Gln Glu Val Tyr Asp Tyr Lys Lys Thr Val Val Glu Pro
    290                 295                 300
Gly Gln Lys Leu Asn Glu Glu Trp Asp Arg Met Phe Glu Glu Tyr Lys
305                 310                 315                 320
Thr Lys Phe Pro Glu Lys Gly Lys Glu Leu Gln Arg Arg Leu Asn Gly
                325                 330                 335
Glu Leu Pro Glu Gly Trp Glu Lys His Leu Pro Lys Phe Thr Pro Asp
            340                 345                 350
Asp Asp Ala Leu Ala Thr Arg Lys Thr Ser Gln Val Leu Thr Asn
            355                 360                 365
Met Val Gln Val Leu Pro Glu Leu Ile Gly Gly Ser Ala Asp Leu Thr
    370                 375                 380
Pro Ser Asn Leu Thr Arg Trp Glu Gly Ala Val Asp Phe Gln Pro Pro
385                 390                 395                 400
Ile Thr Gln Leu Gly Asn Tyr Ala Gly Arg Tyr Ile Arg Tyr Gly Val
                405                 410                 415
Arg Glu His Gly Met Gly Ala Ile Met Asn Gly Ile Ser Ala Phe Gly
            420                 425                 430
Ala Asn Tyr Lys Pro Tyr Gly Gly Thr Phe Leu Asn Phe Val Ser Tyr
            435                 440                 445
Ala Ala Gly Ala Val Arg Leu Ala Ala Leu Ser Gly Asn Pro Val Ile
    450                 455                 460
Trp Val Ala Thr His Asp Ser Ile Gly Leu Gly Glu Asp Gly Pro Thr
465                 470                 475                 480
His Gln Pro Ile Glu Thr Leu Ala His Leu Arg Ala Ile Pro Asn Met
                485                 490                 495
His Val Trp Arg Pro Ala Asp Gly Asn Glu Thr Ser Ala Ala Tyr Tyr
            500                 505                 510
Ser Ala Ile Lys Ser Gly Arg Thr Pro Ser Val Val Ala Leu Ser Arg
    515                 520                 525
Gln Asn Leu Pro Gln Leu Glu His Ser Ser Phe Glu Lys Ala Leu Lys
530                 535                 540
Gly Gly Tyr Val Ile His Asp Val Glu Asn Pro Asp Ile Ile Leu Val
545                 550                 555                 560
Ser Thr Gly Ser Glu Val Ser Ile Ser Asp Ala Ala Lys Lys Leu
                565                 570                 575
Tyr Asp Thr Lys Lys Ile Lys Ala Arg Val Val Ser Leu Pro Asp Phe
            580                 585                 590
Tyr Thr Phe Asp Arg Gln Ser Glu Glu Tyr Arg Phe Ser Val Leu Pro
            595                 600                 605
Asp Gly Val Pro Ile Met Ser Phe Glu Val Leu Ala Thr Ser Ser Trp
    610                 615                 620
Gly Lys Tyr Ala His Gln Ser Phe Gly Leu Asp Glu Phe Gly Arg Ser
625                 630                 635                 640
Gly Lys Gly Pro Glu Ile Tyr Lys Leu Phe Asp Phe Thr Ala Asp Gly
                645                 650                 655
Val Ala Ser Arg Ala Glu Lys Thr Ile Asn Tyr Tyr Lys Gly Lys Gln
            660                 665                 670
```

```
Leu Leu Ser Pro Met Gly Arg Ala Phe
        675             680
```

<210> SEQ ID NO 52
<211> LENGTH: 677
<212> TYPE: PRT
<213> ORGANISM: Pichia stipitis

<400> SEQUENCE: 52

```
Met Ser Ser Val Asp Gln Lys Ala Ile Ser Thr Ile Arg Leu Leu Ala
1               5                   10                  15

Val Asp Ala Val Ala Ala Asn Ser Gly His Pro Gly Ala Pro Leu
            20                  25                  30

Gly Leu Ala Pro Ala Ala His Ala Val Phe Lys Lys Met Arg Phe Asn
            35                  40                  45

Pro Lys Asp Thr Lys Trp Ile Asn Arg Asp Arg Phe Val Leu Ser Asn
        50                  55                  60

Gly His Ala Cys Ala Leu Leu Tyr Ser Met Leu Val Leu Tyr Gly Tyr
65                  70                  75                  80

Asp Leu Thr Val Glu Asp Leu Lys Lys Phe Arg Gln Leu Gly Ser Lys
                85                  90                  95

Thr Pro Gly His Pro Glu Asn Thr Asp Val Pro Gly Ala Glu Val Thr
            100                 105                 110

Thr Gly Pro Leu Gly Gln Gly Ile Cys Asn Gly Val Gly Ile Ala Leu
            115                 120                 125

Ala Gln Ala Gln Phe Ala Ala Thr Tyr Asn Lys Pro Asp Phe Pro Ile
        130                 135                 140

Ser Asp Ser Tyr Thr Tyr Val Phe Leu Gly Asp Gly Cys Leu Met Glu
145                 150                 155                 160

Gly Val Ser Ser Glu Ala Ser Ser Leu Ala Gly His Leu Gln Leu Gly
                165                 170                 175

Asn Leu Ile Ala Phe Trp Asp Asp Asn Lys Ile Ser Ile Asp Gly Ser
            180                 185                 190

Thr Glu Val Ala Phe Thr Glu Asp Val Ile Ala Arg Tyr Lys Ser Tyr
            195                 200                 205

Gly Trp His Ile Val Glu Val Ser Asp Ala Asp Thr Asp Ile Thr Ala
        210                 215                 220

Ile Ala Ala Ala Ile Asp Glu Ala Lys Lys Val Thr Asn Lys Pro Thr
225                 230                 235                 240

Leu Val Arg Leu Thr Thr Thr Ile Gly Phe Gly Ser Leu Ala Gln Gly
                245                 250                 255

Thr His Gly Val His Gly Ala Pro Leu Lys Ala Asp Asp Ile Lys Gln
            260                 265                 270

Leu Lys Thr Lys Trp Gly Phe Asn Pro Glu Glu Ser Phe Ala Val Pro
        275                 280                 285

Ala Glu Val Thr Ala Ser Tyr Asn Glu His Val Ala Glu Asn Gln Lys
        290                 295                 300

Ile Gln Gln Gln Trp Asn Glu Leu Phe Ala Ala Tyr Lys Gln Lys Tyr
305                 310                 315                 320

Pro Glu Leu Gly Ala Glu Leu Gln Arg Arg Leu Asp Gly Lys Leu Pro
                325                 330                 335

Glu Asn Trp Asp Lys Ala Leu Pro Val Tyr Thr Pro Ala Asp Ala Ala
            340                 345                 350

Val Ala Thr Arg Lys Leu Ser Glu Ile Val Leu Ser Lys Ile Ile Pro
```

355                 360                 365
Glu Val Pro Glu Ile Ile Gly Gly Ser Ala Asp Leu Thr Pro Ser Asn
    370                 375                 380

Leu Thr Lys Ala Lys Gly Thr Val Asp Phe Gln Pro Ala Ala Thr Gly
385                 390                 395                 400

Leu Gly Asp Tyr Ser Gly Arg Tyr Ile Arg Tyr Gly Val Arg Glu His
                405                 410                 415

Ala Met Gly Ala Ile Met Asn Gly Ile Ala Ala Phe Gly Ala Asn Tyr
            420                 425                 430

Lys Asn Tyr Gly Gly Thr Phe Leu Asn Phe Val Ser Tyr Ala Ala Gly
        435                 440                 445

Ala Val Arg Leu Ser Ala Leu Ser Glu Phe Pro Ile Thr Trp Val Ala
    450                 455                 460

Thr His Asp Ser Ile Gly Leu Gly Glu Asp Gly Pro Thr His Gln Pro
465                 470                 475                 480

Ile Glu Thr Leu Ala His Phe Arg Ala Thr Pro Asn Ile Ser Val Trp
                485                 490                 495

Arg Pro Ala Asp Gly Asn Glu Thr Ser Ala Ala Tyr Lys Ser Ala Ile
            500                 505                 510

Glu Ser Thr His Thr Pro His Ile Leu Ala Leu Thr Arg Gln Asn Leu
        515                 520                 525

Pro Gln Leu Glu Gly Ser Ser Ile Glu Lys Ala Ser Lys Gly Gly Tyr
    530                 535                 540

Thr Leu Val Gln Gln Asp Lys Ala Asp Ile Ile Val Ala Thr Gly
545                 550                 555                 560

Ser Glu Val Ser Leu Ala Val Asp Ala Leu Lys Val Leu Glu Gly Gln
                565                 570                 575

Gly Ile Lys Ala Gly Val Val Ser Leu Pro Asp Gln Leu Thr Phe Asp
            580                 585                 590

Lys Gln Ser Glu Glu Tyr Lys Leu Ser Val Leu Pro Asp Gly Val Pro
        595                 600                 605

Ile Leu Ser Val Glu Val Met Ser Thr Phe Gly Trp Ser Lys Tyr Ser
    610                 615                 620

His Gln Gln Phe Gly Leu Asn Arg Phe Gly Ala Ser Gly Lys Ala Pro
625                 630                 635                 640

Glu Ile Phe Lys Leu Phe Glu Phe Thr Pro Glu Gly Val Ala Glu Arg
                645                 650                 655

Ala Ala Lys Thr Val Ala Phe Tyr Lys Gly Lys Asp Val Val Ser Pro
            660                 665                 670

Leu Arg Ser Ala Phe
        675

<210> SEQ ID NO 53
<211> LENGTH: 348
<212> TYPE: PRT
<213> ORGANISM: Saccharomyces cerevisiae

<400> SEQUENCE: 53

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

```
His Ala Trp His Gly Asp Trp Pro Leu Pro Val Lys Leu Pro Leu Val
         50                  55                  60
Gly Gly His Glu Gly Ala Gly Val Val Val Gly Met Gly Glu Asn Val
 65                  70                  75                  80
Lys Gly Trp Lys Ile Gly Asp Tyr Ala Gly Ile Lys Trp Leu Asn Gly
                 85                  90                  95
Ser Cys Met Ala Cys Glu Tyr Cys Glu Leu Gly Asn Glu Ser Asn Cys
                100                 105                 110
Pro His Ala Asp Leu Ser Gly Tyr Thr His Asp Gly Ser Phe Gln Gln
                115                 120                 125
Tyr Ala Thr Ala Asp Ala Val Gln Ala Ala His Ile Pro Gln Gly Thr
130                 135                 140
Asp Leu Ala Gln Val Ala Pro Ile Leu Cys Ala Gly Ile Thr Val Tyr
145                 150                 155                 160
Lys Ala Leu Lys Ser Ala Asn Leu Met Ala Gly His Trp Val Ala Ile
                165                 170                 175
Ser Gly Ala Ala Gly Gly Leu Gly Ser Leu Ala Val Gln Tyr Ala Lys
                180                 185                 190
Ala Met Gly Tyr Arg Val Leu Gly Ile Asp Gly Gly Glu Gly Lys Glu
                195                 200                 205
Glu Leu Phe Arg Ser Ile Gly Gly Glu Val Phe Ile Asp Phe Thr Lys
                210                 215                 220
Glu Lys Asp Ile Val Gly Ala Val Leu Lys Ala Thr Asp Gly Gly Ala
225                 230                 235                 240
His Gly Val Ile Asn Val Ser Val Ser Glu Ala Ala Ile Glu Ala Ser
                245                 250                 255
Thr Arg Tyr Val Arg Ala Asn Gly Thr Thr Val Leu Val Gly Met Pro
                260                 265                 270
Ala Gly Ala Lys Cys Cys Ser Asp Val Phe Asn Gln Val Val Lys Ser
                275                 280                 285
Ile Ser Ile Val Gly Ser Tyr Val Gly Asn Arg Ala Asp Thr Arg Glu
                290                 295                 300
Ala Leu Asp Phe Phe Ala Arg Gly Leu Val Lys Ser Pro Ile Lys Val
305                 310                 315                 320
Val Gly Leu Ser Thr Leu Pro Glu Ile Tyr Glu Lys Met Glu Lys Gly
                325                 330                 335
Gln Ile Val Gly Arg Tyr Val Val Asp Thr Ser Lys
                340                 345

<210> SEQ ID NO 54
<211> LENGTH: 1329
<212> TYPE: DNA
<213> ORGANISM: Eubacterium saburreum

<400> SEQUENCE: 54
atgaaggaat tcttcccagg tatttctcca gttaagttcg aaggtagaga ctctaagaac    60
ccattgtctt tcaagtacta cgacgctaag agagttatta tgggtaagac catggaagaa   120
cacttgtctt tcgctatggc ttggtggcac aacttgtgtg cttgtggtgt tgacatgttc   180
ggtcaaggta ccgttgacaa gtctttcggt gaatcttctg gtaccatgga acacgctaga   240
gctaaggttg acgctggtat tgaattcatg aagaagttgg gtattaagta ctactgtttc   300
cacgacaccg acattgttcc agaagaccaa gaagacatta cgttaccaa cgctagattg   360 gacgaaatta ccgactacat tttggaaaag accaaggaca ccgacattaa gtgtttgtgg   420
```

```
accacctgta acatgttctc taacccaaga ttcatgaacg gtgctggttc ttctaactct    480
gctgacgttt tctgtttcgc tgctgctcaa gctaagaagg gtttggaaaa cgctgttaag    540
ttgggtgcta agggtttcgt tttctggggt ggtagagaag gttacgaaac cttgttgaac    600
accgacatga agttggaaga agaaaacatt gctaccttgt tcaccatgtg tagagactac    660
ggtagatcta ttggtttcat gggtgacttc tacattgaac caaagccaaa ggaaccaatg    720
aagcaccaat acgacttcga cgctgctacc gctattggtt tcttgagaaa gtacggtttg    780
gacaaggact tcaagttgaa cattgaagct aaccacgcta ccttggctgg tcacaccttc    840
caacacgaat tgagagtttg tgctgttaac ggtatgatgg gttctgttga cgctaaccaa    900
ggtgacacct tgttgggttg ggacaccgac caattcccaa ccaacgttta cgacaccacc    960
ttggctatgt acgaaatttt gaaggctggt ggtttgagag gtggtttgaa cttcgactct   1020
aagaacagaa gaccatctaa caccgctgac gacatgttct acggtttcat tgctggtatg   1080
gacaccttcg ctttgggttt gattaaggct gctgaaatta ttgaagacgg tagaattgac   1140
gacttcgtta aggaaagata cgcttcttac aactctggta ttggtaagaa gattagaaac   1200
agaaaggtta ccttgattga atgtgctgaa tacgctgcta agttgaagaa gccagaattg   1260
ccagaatctg gtagacaaga atacttggaa tctgttgtca acaacatttt gttcggtggt   1320
tctggttaa                                                           1329
```

OLIGONUCLEOTIDE SEQUENCE FOR USE IN PATHWAY ENGINEERING

CROSS REFERENCE TO RELATED APPLICATIONS

This application claims the priority of PCT/EP2015/076715, filed on 16 Nov. 2015, which claims priority to European Patent Application No. 14195026.1, filed on 26 Nov. 2014, the entire contents of each of which are hereby incorporated in total by reference.

SEQUENCE LISTING

This application incorporates by reference the Sequence Listing contained in an ASCII text file named "366746_00032_Sequence.txt" submitted via EFS-Web. The text file was created on May 11, 2017, and is 175 kb in size.

The present invention comprises a novel artificial oligonucleotide sequence which can initiate the transcription of a gene under various conditions at a high level. Further the invention relates to a recombinant DNA fragment comprising the artificial oligonucleotide sequence, an expression plasmid comprising the recombinant DNA fragment and a host cell transformed with the recombinant DNA fragment.

The yeast *S. cerevisiae* and *S. sensu stricto* species are used since thousands of years for the production of bread and alcoholic beverages like sake, wine or beer. Through this long period of industrial usage, yeasts are adapted to the process conditions and can tolerate the mechanical forces in a bioreactor, inhibitory substances and fermentation products. Further they are robust against fluctuations in temperature and can ferment sugars at low pH-value, which minimizes the contamination risk. Besides this, *S. cerevisiae* is a key laboratory model system and can be easily genetically modified and is generally recognized as safe—GRAS status. A broad genetic tool set is available for *S. cerevisiae* and many intracellular processes like metabolism, secretion, transport, signaling and other pathways are well studied, which help to successfully engineer the yeast for a wide variety of applications.

Especially the introduction of multi-enzyme pathways requires precise control over the level of gene expression especially of the key enzyme, which can be heterologous or native, to maximize substrate utilization and/or product formation. Thereby the transcriptional control takes place at the oligonucleotide sequence which is located in the upstream region of a gene—the promoter. Thus, promoter strength and regulation are critical points for metabolic engineering.

As endogenous promoters do usually not completely fulfil the necessary continuum of transcriptional control and therefore do not maximize the transcription levels achievable within the cell, a critical step for the engineering of yeast is the choice of the right promoter.

Different types of promoters are known within the art.

Inducible or de-repressed promoters allow a high level of transcriptional control but they depend on an inducer or defined process conditions. Regulated promoters are limited to the production of toxic proteins or building up pathways with toxic intermediates. Further, most of the promoters of the state of the art are only known to enable the control of the transcription of one specific group of genes.

Thus, promoters so far known to a person skilled in the art always involve certain disadvantages which severely limit their use to just a few specific applications.

The inventors of the present invention have therefore set themselves the task to develop novel and improved promoters which enable a high transcriptional control of a wider variety of genes and which are highly feasible for industrial applications.

The inventors of the present invention surprisingly found that this task can be solved by an oligonucleotide sequence characterized in that it increases the transcription rate of a RNA typed as messenger RNA fragment encoding for a protein selected from the group consisting of enzymes, structural proteins, coenzymes, transporters, antibodies, hormones and regulators, as regulatory RNA fragment, as enzymatically active RNA fragment or as transfer RNA fragment, said oligonucleotide sequence having at least 80% sequence identity to SEQ ID NO: 1.

The nomenclature of amino acids, peptides, nucleotides and nucleic acids within the present application follows the suggestions of IUPAC. Generally, amino acids are named within this document according to the one letter code.

The term "oligonucleotide" according to the present invention is to be understood as a single-stranded or double-stranded DNA or RNA molecule comprising from 2 to 1000 nucleic acids, preferably from 10 to 900 nucleic acids, further preferred from 50 to 850 nucleic acids and most preferred from 100 to 820 nucleic acids.

The terms "DNA" and "RNA" are well known to a person skilled in the art. While DNA contains deoxyribose, RNA contains ribose (in deoxyribose there is no hydroxyl group attached to the pentose ring in the 2' position). The complementary base to adenine is not thymine, as it is in DNA, but rather uracil, which is an unmethylated form of thymine.

The oligonucleotide according to the present invention comprises an nucleic acid sequence having at least 80% sequence identity, preferably at least 82%, further preferred at least 85%, particularly preferred at least 90%, even more preferred at least 92%, also preferred at least 95%, furthermore preferred at least 98% and most preferred at least 99% sequence identity to SEQ ID NO: 1.

Within a particularly preferred embodiment, the nucleic acid sequence is selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7.

The oligonucleotide according to the present invention increases the transcription rate of certain RNA fragments. The term "increasing the transcription rate" is thereby to be understood as an increase compared to an oligonucleotide with promoter activity of the state of the art. The "increase of the transcription rate" is generally to be determined as follows:

$$\frac{RTL_I}{RTL_S}$$

RRL$_I$—relative transcript level of a reporter system controlled by an oligonucleotide according to the invention RTL$_S$—relative transcript level of a reporter system controlled by an oligonucleotide according to the state of the art Thereby the relative transcript level is measured as the concentration of RNA of the reporter system in a cell extract in relation to the concentration of the RNA of a housekeeping gene in the same cell extract.

Whereas RTL$_I$ and RTL$_S$ are determined by use of the same type of host cell whereas the host cell is transformed with at least one recombinant DNA fragment comprising the respective oligonucleotide and the host cell is grown under identical state of the art conditions whereas the host cell is harvested within the exponential growth phase.

Within a preferred embodiment the transcription rate is at least 2-fold higher when growing a yeast host cell, preferably S. cerevisiae, transformed with at least one recombinant DNA fragment comprising an oligonucleotide according to the present invention on at least two substrates selected from the group consisting of glucose, mannose, fructose, galactose, xylose, arabinose, sucrose, trehalose, raffinose, glycerol, ethanol, acetate and lactate. The increase was determined as follows:

$$\frac{RTL_{Ie}}{RTL_{Se}}$$

$RTL_{Ie}$—relative transcript level of the messenger RNA encoding for SEQ ID NO: 17 controlled by the oligonucleotide SEQ ID NO: 1.

$RTL_{Se}$—relative transcript level of the messenger RNA encoding for SEQ ID NO: 17 controlled by the oligonucleotide SEQ ID NO: 9

Thereby the relative transcript level is measured as the concentration of messenger RNA encoding for SEQ ID NO: 17 in a yeast (S. cerevisiae) cell extract in relation to the concentration of the messenger RNA of the housekeeping gene encoding for actin in the same yeast cell extract.

Whereas $RTL_{Ie}$ and $RTL_{Se}$ are determined by use of the same type of yeast host cell (S. cerevisiae) whereas the yeast host cell is transformed with at least one recombinant DNA fragment comprising the respective oligonucleotide and the yeast host cell is grown under identical state of the art conditions whereas the yeast host cell is harvested within the exponential growth phase.

Within a particularly preferred embodiment of the present invention, the transcription rate of the gene in a yeast host cell transformed with at least one recombinant DNA fragment comprising the oligonucleotide according to the present invention is increased by at least 2-fold, more preferred at least 4-fold, particularly preferred at least 6-fold and most preferred at least 10-fold when growing the yeast host cell on at least two substrates selected from the group consisting of glucose, mannose, fructose, galactose, xylose, arabinose, sucrose, trehalose, raffinose, glycerol, ethanol, acetate and lactate.

Within a further particularly preferred embodiment of the present invention, the transcription rate of the gene in a host cell is increased by at least 2-fold, preferably at least 4-fold, more preferred at least 6-fold, particularly preferred at least 8-fold and most preferred at least 10-fold when growing the host cell on at least two substrates selected from the group consisting of glucose, mannose, fructose, xylose, sucrose glycerol and ethanol.

Within another particularly preferred embodiment of the present invention, the transcription rate of the gene in a host cell is increased by at least 2-fold, preferably at least 4-fold, more preferred at least 6-fold, particularly preferred at least 8-fold and most preferred at least 10-fold when growing the host cell on at least two substrates selected from the group consisting of glucose, mannose, glycerol, ethanol and xylose.

Another advantage of the oligonucleotide according to the present invention is that it increases the enzyme activity of an enzyme encoded by an RNA controlled by the oligonucleotide. The term "x-fold higher enzyme activity" is thereby to be understood as an increase compared to an oligonucleotide with promoter activity of the state of the art. The "x-fold higher enzyme activity" is generally to be determined as follows:

$$\frac{EA_I}{EA_S}$$

$EA_I$—enzyme activity of a reporter system controlled by an oligonucleotide according to the invention $EA_S$—enzyme activity of a reporter system controlled by an oligonucleotide according to the state of the art Thereby the enzyme activity is measured as the amount of a substrate converted per minute by defined amount of a cell extract excluding the background activity of the reporter system.

Whereas $EA_I$ and $EA_S$ are determined by use of the same type of host cell whereas the host cell is transformed with at least one recombinant DNA fragment comprising the respective oligonucleotide and the host cell is grown under identical state of the art conditions whereas the host cell is harvested within the exponential growth phase.

Within a preferred embodiment the enzyme activity is increased by at least 2-fold when growing a yeast host cell, preferably S. cerevisiae, transformed with at least one recombinant DNA fragment comprising an oligonucleotide according to the present invention on at least two substrates selected from the group consisting of glucose, mannose, fructose, galactose, xylose, arabinose, sucrose, trehalose, raffinose, glycerol, ethanol, acetate and lactate.

The increase was determined as follows:

$$\frac{EA_{Ie}}{EA_{Se}}$$

$EA_{Ie}$—enzyme activity of the protein SEQ ID NO: 17 controlled by the oligonucleotide SEQ ID NO: 1 or a derivate with at least 80% sequence identity to SEQ ID NO: 1.

$EA_{Se}$—enzyme activity of the protein SEQ ID NO: 17 controlled by an oligonucleotide SEQ ID NO: 9.

Thereby the enzyme activity is measured as the amount of xylose converted per minute by defined amount of a cell extract excluding the background activity of the reporter system.

Whereas $EA_{Ie}$ and $EA_{Se}$ are determined by use of the same type of host cell (S. cerevisiae) whereas the host cell is transformed with at least one recombinant DNA fragment comprising the respective oligonucleotide and the host cell is grown under identical state of the art conditions whereas the host cell is harvested within the exponential growth phase.

Within a particularly preferred embodiment of the present invention, the enzyme activity in a yeast host cell transformed with at least one recombinant DNA fragment comprising the oligonucleotide according to the present invention is increased by at least 2-fold, preferably at least 4-fold more preferred at least 6-fold, particularly preferred at least 8-fold and most preferred at least 10-fold when growing the yeast host cell on at least two substrates selected from the group consisting of glucose, mannose, fructose, galactose, xylose, arabinose, sucrose, trehalose, raffinose, glycerol, ethanol, acetate and lactate.

Within a further particularly preferred embodiment of the present invention the enzyme activity in a host cell is increased by at least 2-fold, preferably at least 4-fold, more preferred at least 6-fold, particularly preferred at least 8-fold and most preferred at least 10-fold when growing the host cell on at least two substrates selected from the group consisting of glucose, mannose, fructose, xylose, sucrose, glycerol and ethanol.

Within a further particularly preferred embodiment of the present invention the enzyme activity in a host cell is increased by at least 2-fold, preferably at least 4-fold, more preferred at least 6-fold, particularly preferred at least 8-fold and most preferred at least 10-fold when growing the host cell on at least two substrates selected from the group consisting of glucose, mannose, glycerol, ethanol and xylose.

Within the present invention, the term "regulatory RNA fragment" (rRNA fragment) is to be understood as a RNA chain that has the ability to downregulate a gene expression by being complementary to a part of an mRNA or a gene's DNA. Examples of "rRNA fragments" are MicroRNAs (miRNA) which act through RNA interference (RNAi), where an effector complex of miRNA and enzymes can cleave complementary mRNA, block the mRNA from being translated, or accelerate its degradation. An mRNA may contain regulatory elements itself, such as riboswitches, in the 5' untranslated region or 3' untranslated region; these cis-regulatory elements regulate the activity of that mRNA. The untranslated regions can also contain elements that regulate other genes.

Within the present invention, the term "enzymatically active RNA fragment" is to be understood as RNA which is part of a protein complex which can catalyze enzymatic reactions within the cell like ribosomal RNA or RNA that forms a catalytically active complex itself such as ribozyme (ribonucleic acid enzymes).

Within the present invention, the term "transfer RNA fragment" (tRNA fragment) is to be understood as a small RNA chain of about 80 nucleotides that has the ability to transfer a specific amino acid to a growing polypeptide chain at the ribosomal site of protein synthesis during translation. It has sites for amino acid attachment and an anticodon region for codon recognition that binds to a specific sequence on the messenger RNA chain through hydrogen bonding.

Within the present invention, the term "messenger RNA fragment" (mRNA fragment) is to be understood as a small RNA chain that has the ability to carry information about a protein sequence to the ribosomes. Every three nucleotides (a codon) correspond to one amino acid. In eukaryotic cells, once precursor mRNA (pre-mRNA) has been transcribed from DNA, it is processed to mature mRNA. This removes its introns—non-coding sections of the pre-mRNA. The mRNA is then exported from the nucleus to the cytoplasm, where it is bound to ribosomes and translated into its corresponding protein form with the help of tRNA. In prokaryotic cells, which do not have a nucleus and cytoplasm compartments, mRNA can bind to ribosomes while it is being transcribed from DNA. After a certain amount of time the messenger RNA degrades into its component nucleotides with the assistance of ribonucleases.

Within the present invention the term "structural proteins" refers to proteins which confer stiffness and rigidity to otherwise-fluid biological components. Preferred structural proteins are selected from the group consisting of fibrous proteins such as collagen, elastin and keratin; and globular proteins such as actin and tubulin. Other proteins that serve structural functions and which are to be understood as "structural proteins" within the present invention are motor proteins such as myosin, kinesin, and dynein, which are capable of generating mechanical forces.

Preferred RNA fragments encoding for a structural protein are selected from the group consisting of actine, elastin, filamine, collagen, myosine, lamine.

Preferred RNA fragments encoding for a coenzyme are selected from the group of RNA fragments encoding for polypeptides which are post-translationally modified. Examples are tryptophan tryptophylquinone (TTQ) and 4-methylidene-imidazole-5-one (MIO).

Preferred RNA fragments encoding for a transporter are selected from the group of RNA fragments encoding for uniport-, symport- and antiport carriers, proton pumps, ion channels and aquaporines.

Preferred RNA fragments encoding for an antibody are selected from the group of RNA fragments encoding for IgA, IgD, IgE, EgG, IgM, IgY and IgW.

Preferred RNA fragments encoding for a hormone are selected from the group of RNA fragments encoding for small peptide hormones such as TRH and vasopressin; insulin; growth hormone; glycoprotein hormones such as luteinizing hormone, follicle-stimulating hormone and thyroid-stimulating hormone.

Preferred RNA fragments encoding for a regulator are selected from the group of RNA fragments encoding for receptors, transcription factors, metabolic sensors, light sensors, electro sensors, mechanical sensors and signal transducers.

Preferred RNA fragments encoding for an enzyme are selected from the group of RNA fragments encoding for carbohydrate-modifying enzymes. Within the present invention, the term "carbohydrate-modifying enzyme" is to be understood as comprising any enzyme capable of modifying any kind of carbohydrate such as (but not limited to) carbohydrate-cleaving, carbohydrate-oxidizing, carbohydrate-reducing, carbohydrate-decarboxylating, carbohydrate-deacetylating, carbohydrate-acetylating, carbohydrate-methylating, carbohydrate-demethylating, carbohydrate-aminating, carbohydrate-phosphorylating, carbohydrate-dephosphorylating, carbohydrate-isomerizating, carbohydrate-epimerizating and carbohydrate-deaminating enzymes.

Within a particularly preferred embodiment of the present invention, the carbohydrate-modifying enzyme is selected from the group consisting of the classes EC 5.1.3, EC 5.3.1, EC 2.7.1, EC 2.2.1, EC 2.2.1 and EC 1.1.1, preferably selected from the group consisting of EC 5.1.3.3, EC 5.3.1.5, EC 2.7.1.17, EC 2.2.1.2, EC 2.2.1.1 and EC 1.1.1.1. Within a further particularly preferred embodiment, the protein is selected from the group consisting of SEQ ID NOs 11 to 53.

Within a further preferred embodiment of the present invention 1 to 80 nucleotides of the oligonucleotide of the present invention are "mutated". Within the present invention the term "mutated" is to be understood as "substituted", "deleted" or "inserted". The term "mutation" is to be understood as "substitution", "deletion" or "insertion". Substitutions are classified as transitions where a purine is exchanged by a purine (A↔G) or a pyrimidine by a pyrimidine (C↔T) or transversions where a purine is exchanged by a pyridine and vice versa (C/T↔A/G). Insertions add one or more additional nucleotides (A, C, T or G) into an oligonucleotide. The removal of one or more nucleotides from the DNA is called deletion.

Within a further embodiment, the present invention provides a recombinant DNA fragment comprising the oligonucleotide according to the present invention.

Particularly preferred recombinant DNA fragments according to the present invention comprise an oligonucleotide selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7 and a RNA fragment encoding for a protein selected from the group consisting of enzymes, structural proteins, coenzymes, transporters, antibodies, hormones and regulators. It is further particularly preferred that the protein is an enzyme and the enzyme is selected from the group consisting of the classes EC 5.1.3, EC 5.3.1, EC 2.7.1, EC 2.2.1, EC 2.2.1 and EC 1.1.1, preferably selected from the group consisting of EC 5.1.3.3, EC 5.3.1.5, EC 2.7.1.17, EC 2.2.1.2, EC 2.2.1.1 and EC 1.1.1.1. Other particularly preferred recombinant DNA fragments comprise an oligonucleotide selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7 and a RNA fragment selected from the group consisting of SEQ ID NOs 11 to 53.

Within a further embodiment, the present invention provides an expression plasmid comprising at least one recombinant DNA fragment according to the present invention.

The present invention further provides a host cell transformed with at least one recombinant DNA fragment comprising the oligonucleotide according to the present invention. The host cell according to the present invention is preferably used for pathway engineering or for metabolic transformation of xylose containing substrates to preferred metabolites.

The recombinant host cell according to the present invention is preferably selected from bacteria, yeast, or fungal cells. In a particularly preferred embodiment, the host cell is selected from the group consisting of *Escherichia, Klebsiella, Pseudomonas, Lactobacillus, Bacillus, Streptomyces; Saccharomyces, Kluyveromyces, Schizosaccharomyces, Candida, Yarrowia, Komagataella, Pichia, Hansenula, Penicillium, Trichoderma, Hypocrea, Aspergillus, Cantharellu, Agraicus, Boletos, Pleurotus, Trametes, Phanerochaete, Myceliophthora. Chaetomium, Humicola, Chrysosporium, Talaromyces* and *Neurospora*.

It is particularly preferred to select the host cell from the group consisting of *Lactococcus lactis, Lactobacillus brevis, Bacillus subtilis, Bacillus megaterium, Bacillus lentus, Bacillus amyloliquefaciens, Bacillus licheniformis, Pseudomonas fluorescence, Klebsiella planticola, Escherichia coli, Streptomyces lividans, Saccharomyces cerevisiae, Saccharomyces bayanus, Saccharomyces uravum, Saccharomyces pastorianus, Saccharomyces kudriavzevii, Saccharomyces mikatae, Saccharomyces carlsbergensis, Schizosaccharomyces pombe, Kluyveromyces marxianus, Yarrowina lipolytica, Hansenula polymorpha, Pichia angusta, Komagataella pastoris, Pichia pastoris, Aspergillus niger, Aspergillus oryzae, Trichoderma reesei* and *Myceliophthora thermophila*.

The recombinant host cell according to the present invention may comprise one or more plasmids according to the present invention.

EXAMPLES AND FIGURES

In the following the present invention is described by the examples and figures. The examples and figures are considered for illustrative purpose only and do not limit the scope of the present invention and claims in any respect.

Example 1: Growth Study—Selection of a Screening Strain 5 different host cells have been transformed with a plasmid containing an exemplary oligonucleotide for testing purposes.

TABLE 1 list of tested host cells

| counter | name | origin |
| --- | --- | --- |
| strain A | Ethanol Red ® (Batch 897/1 production date Jan. 5, 2008) | Fermentis, France |
| strain B | Simi White ™ (Lot: 02905340230601V) | Lallemand, Canada |
| strain C | Rhône 2226 ™ (Lot: 025556551030Y9) | |
| strain D | CBS 7764 | Centraalbureau voor Schimmelcultures |
| Strain E | CBS 6413 | (Institute of the Royal Netherlands Academy of Arts and Sciences- KNAW), Netherland |

The plasmid was constructed by recombination cloning in *S. cerevisiae*: A yeast cell was transformed with PCR products offered 45 bp overlap to each other. The fragments were yeast Marker (pUG6 87 to 1559 bp), *E. coli* Marker and Ori (pUG19 754 to 2534 bp), yeast Ori (*S. cerevisiae* S288C chromosome IV 44978 to 449831 and *S. cerevisiae* S288C chromosome II 63156 to 63454 bp) and the functional part (SEQ ID NO:10, SEQ ID NO:54, *S. cerevisiae* S288C chromosome XI 326407 to 326108 bp). Thereby the parts were flanked by the restriction sites SapI, SbfI, StuI and NotI, respectively.

The yeast strains were transformed with the re-isolated plasmid with the high-efficiency LiAc method according to Gietz and Schiestl.

The host cells have then been cultivated in 50 ml of a xylose-containing substrate (10 g/l yeast extract, 20 g/l pepton, 20 g/l Xylose+200 mg/l G418) under aerobic condition in 300 ml shake flask by 30° C. and 250 rpm. The results are shown in FIG. 1.

Strain B has been selected for further tests due to the excellent growth performance.

Example 2: Growth Study—Comparison of Different Plasmids Containing Different Oligonucleotides Strain B has been transformed with 10 plasmids. The plasmids were constructed in the same way as described within example 1 harboring the oligonucleotides SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10, respectively.

Strain B was transformed with the plasmids as described within example 1 and cultivated under the same conditions. The results are shown in FIG. 2.

The host cell transformed by the plasmids containing an oligonucleotide according to the present invention (regulated by SEQ ID NOs:1 to 7) showed a significant higher growth performance than the host cell transformed by plasmids containing oligonucleotides of the state of the art SEQ ID NO: 9, SEQ ID NO: 10 and SEQ ID NO:8.

Example 3: Transcript Level—Comparison of Different Plasmids Containing Different Oligonucleotides The yeast strains harboring the different plasmids described in example 2 were cultivated in 100 ml of glucose-, mannose-, ethanol-, glycerol- or xylose-containing substrate (10 g/l yeast extract, 20 g/l pepton, 20 g/l carbon source+200 mg/l G418) in 500 ml shake flask by 30° C. and 250 rpm. 5 ml of the cultures were harvested at approximately $OD_{600}$ 2—centrifuged, washed with water and centrifuged (two times). After that the pellet of the culture was stored at −80° C.

The total RNA was extracted from the cells by using the RNeasy Mini Kit™, Qiagen Germany according to producer manual. Then that 500 ng RNA were translated into cDNA through the usage of the ThermoScript™ RT-PCR Kit, Life Technologies USA according to producer manual. By using the iQ™ SYBR® Green Supermix and the iQ™ iCycler, BIO RAD Germany, following the producer information, the concentration of ACT1 and XylA mRNA could by calculated by amplifying 225 and 236 bp tall PCR products.

The relative transcript levels (concentration of XylA RNA divided by the concentration of ACT1 RNA) are shown in FIG. 3.

difference regarding the control of the oligonucleotide SEQ ID NO:1 to SEQ ID NO:7 was not visible.

Example 4: Enzyme Activity—Comparison of Different Plasmids Containing Different Oligonucleotides 50 ml of the cultures as defined within example 3 were harvested at approximately $OD_{600}$ 2. Afterwards the pellet of the culture was stored at −80° C. In addition, a culture of strain B carrying the plasmid described within example 2 without the functional part (empty plasmid) was treated in the same way.

The thawed pellets were suspended in 400 µl buffer (100 mM Tris pH 7.5, 10 mM MgCl2) and homogenized. After the cell lysis the crude extracts were diluted to a total protein concentration of 1 µg/µl (measured by Bradford assay). The xylose isomerase activity assays were performed in 100 µl with 10% of the diluted crude extracts, 0.25 mM NADH, 3 U/ml sorbitol dehydrogenase and 500 mM Xylose. The reaction kinetics were followed photometrically at 340 nm.

The measured enzyme activities (minus background activity—empty plasmid) are shown in FIG. 4.

TABLE 3 x-fold change of the xylose isomerase activity under the control of different oligonucleotides in comparison to the xylose isomerase activity under the control of SEQ ID NO: 9

|  | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 |
|---|---|---|---|---|---|---|---|
| Glucose | 22.5 ± 3.6 | 23.7 ± 3.4 | 24.8 ± 3.5 | 24.9 ± 4.0 | 23.9 ± 3.9 | 22.8 ± 4.1 | 20.6 ± 3.2 |
| Mannose | 20.4 ± 4.4 | 20.4 ± 4.5 | 18.6 ± 5.4 | 18.9 ± 4.5 | 19.7 ± 4.7 | 19.7 ± 5.3 | 18.6 ± 4.2 |
| Ethanol | 13.7 ± 2.2 | 13.0 ± 2.2 | 14.0 ± 2.3 | 15.2 ± 2.6 | 13.9 ± 2.3 | 14.6 ± 2.6 | 13.4 ± 2.7 |
| Glycerol | 14.8 ± 4.2 | 14.3 ± 3.8 | 16.9 ± 4.8 | 15.5 ± 4.3 | 15.4 ± 4.3 | 16.5 ± 4.6 | 15.3 ± 4.2 |
| Xylose | 14.3 ± 2.0 | 15.0 ± 2.5 | 16.7 ± 2.6 | 14.8 ± 2.4 | 14.8 ± 2.3 | 14.5 ± 2.2 | 14.5 ± 2.4 |

The reporter system under the control of the oligonucleotides according to the present invention has shown a 14 to 25 fold increase of the enzyme activity. Whereby the enzyme activities vary between the various growth conditions but a significant difference regarding the control of the oligonucleotide SEQ ID NO: 1 to SEQ ID NO: 7 was not visible.

TABLE 2 x-fold change of the XylA transcript level under the control of different oligonucleotides in comparison to the XylA transcript level under the control of SEQ ID NO: 9

|  | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 |
|---|---|---|---|---|---|---|---|
| Glucose | 23.4 ± 5.7 | 23.9 ± 5.9 | 22.6 ± 5.8 | 24.4 ± 5.3 | 28.9 ± 5.1 | 26.4 ± 6.6 | 22.3 ± 4.5 |
| Mannose | 25.3 ± 6.5 | 27.6 ± 6.6 | 25.9 ± 7.0 | 23.3 ± 6.6 | 22.1 ± 4.0 | 22.4 ± 6.7 | 26.2 ± 7.3 |
| Ethanol | 4.6 ± 0.8 | 5.6 ± 1.1 | 3.9 ± 0.7 | 3.9 ± 0.8 | 4.5 ± 0.6 | 4.7 ± 0.6 | 4.9 ± 1.1 |
| Glycerol | 8.3 ± 2.2 | 7.6 ± 3.4 | 7.6 ± 2.7 | 9.3 ± 2.7 | 6.6 ± 1.3 | 6.8 ± 2.3 | 7.0 ± 2.3 |
| Xylose | 6.8 ± 3.3 | 6.6 ± 5.3 | 5.8 ± 3.2 | 8.4 ± 4.1 | 7.1 ± 4.6 | 7.7 ± 4.5 | 7.9 ± 4.4 |

Figure 1:
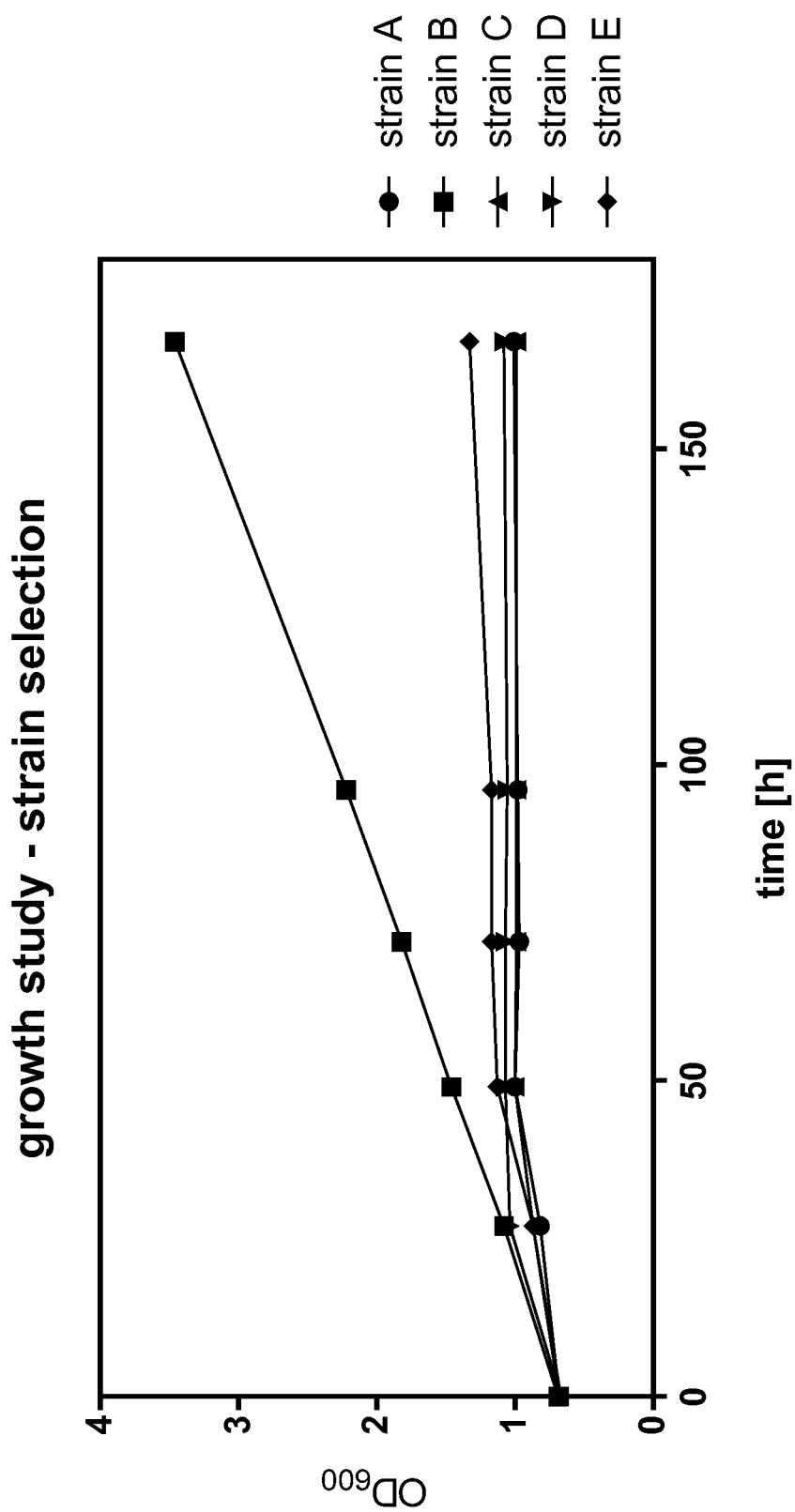
FIG. 1 shows the growth performance of 5 different yeast host cells (A to E) which have been transformed with a plasmid containing a gene encoding for SEQ ID NO:17 regulated by a oligonucleotide according to the state of art: SEQ ID NO:10.
Figure 2:
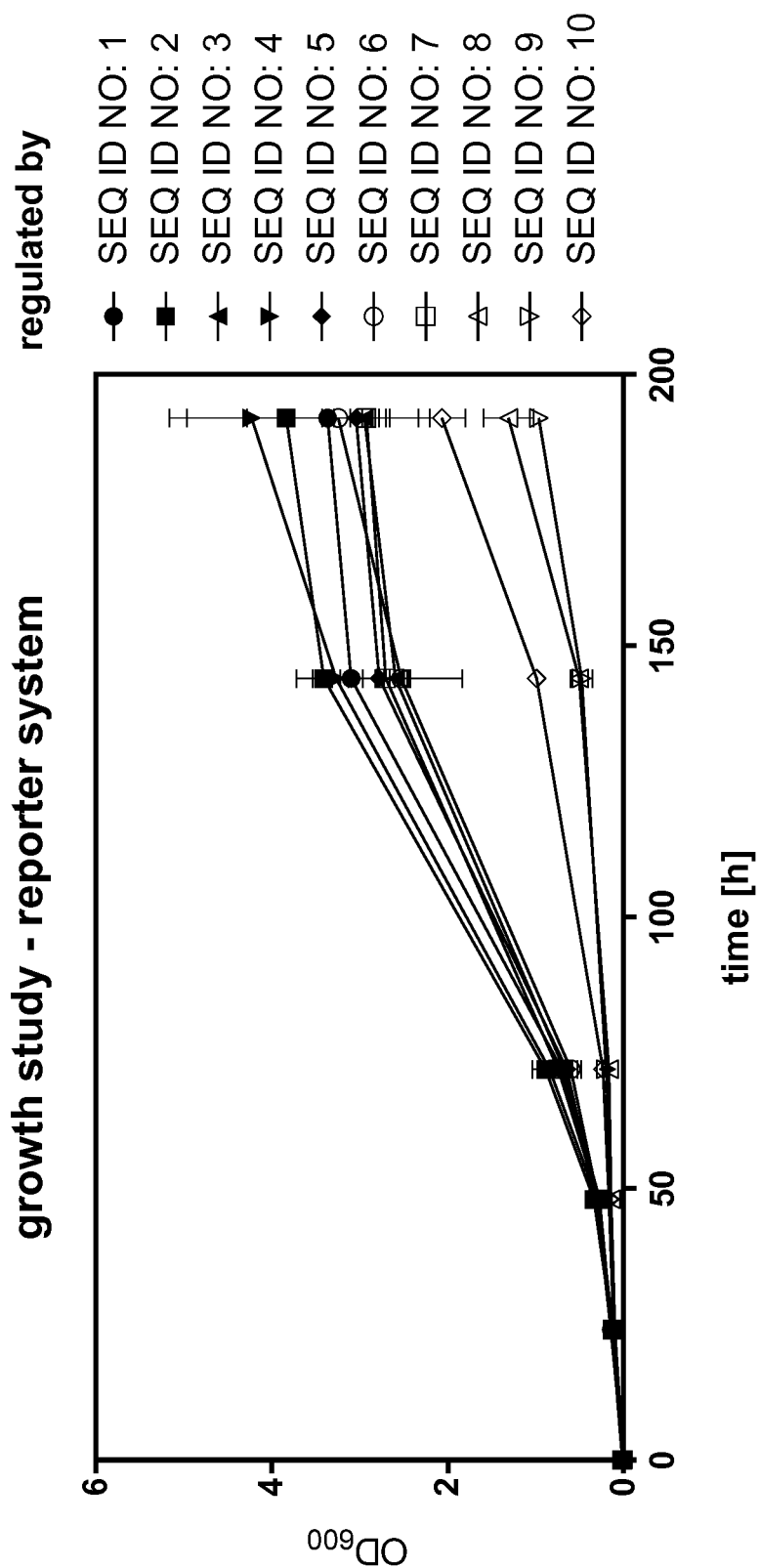

The reporter system under the control of the oligonucleotides according to the present invention has shown a 4 to 29 fold increase of the transcript level. The transcript levels vary between the various growth conditions but a significant FIG. 2 shows the growth performance of strain B transformed with different plasmids containing different oligonucleotides (oligonucleotides of the state of the art and oligonucleotides according to the present invention)

Figure 3:
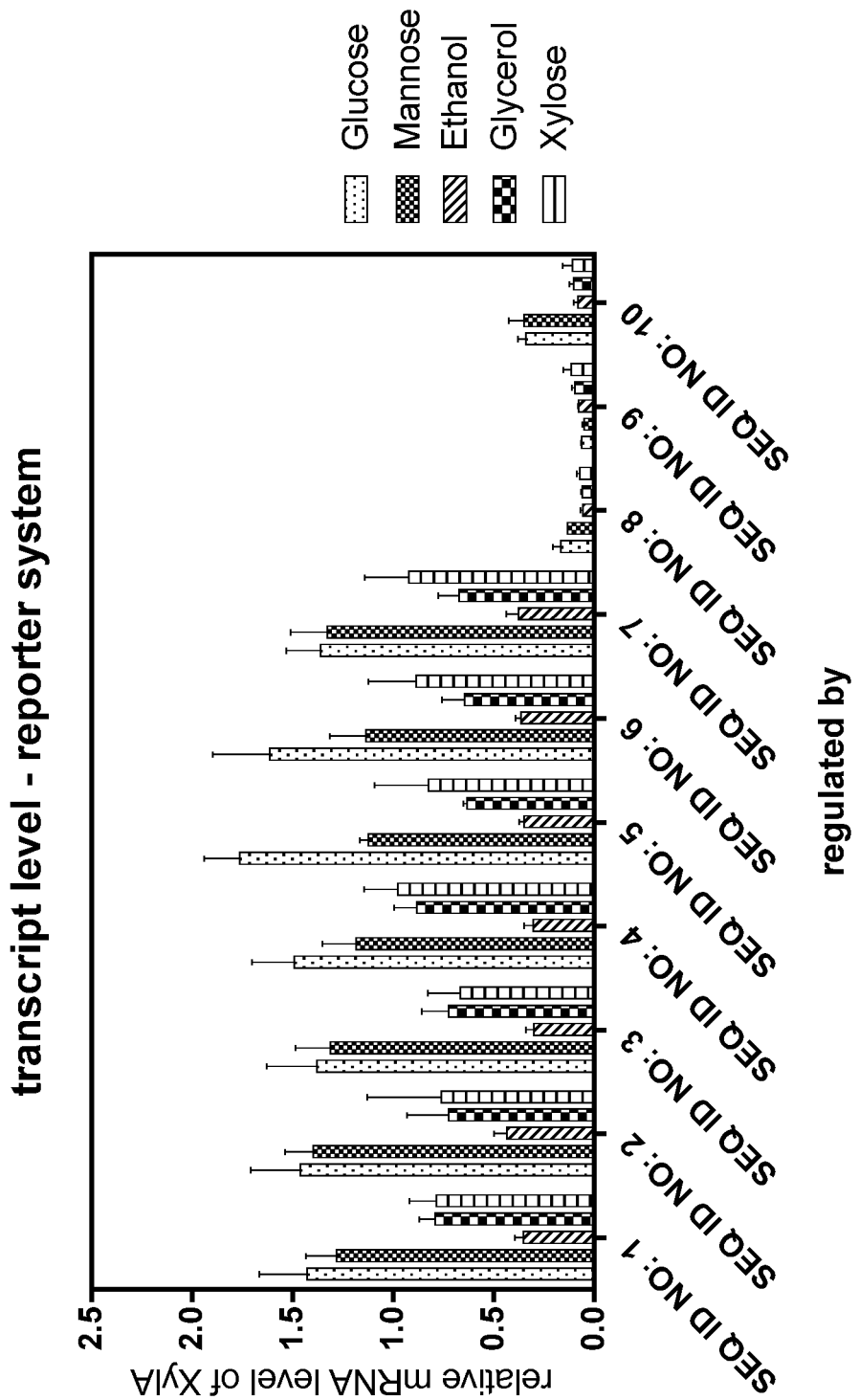

FIG. 3 shows a 4 to 29 fold increase of the transcript level of the reporter system under the control of the oligonucleotides according to the present invention (SEQ ID NOs 1 to 7) compared to the state of the art oligonucleotides SEQ ID NO 8, SEQ ID NO: 9 and SEQ ID NO: 10 on different substrates (glucose, mannose, ethanol, glycerol and xylose)

Figure 4:
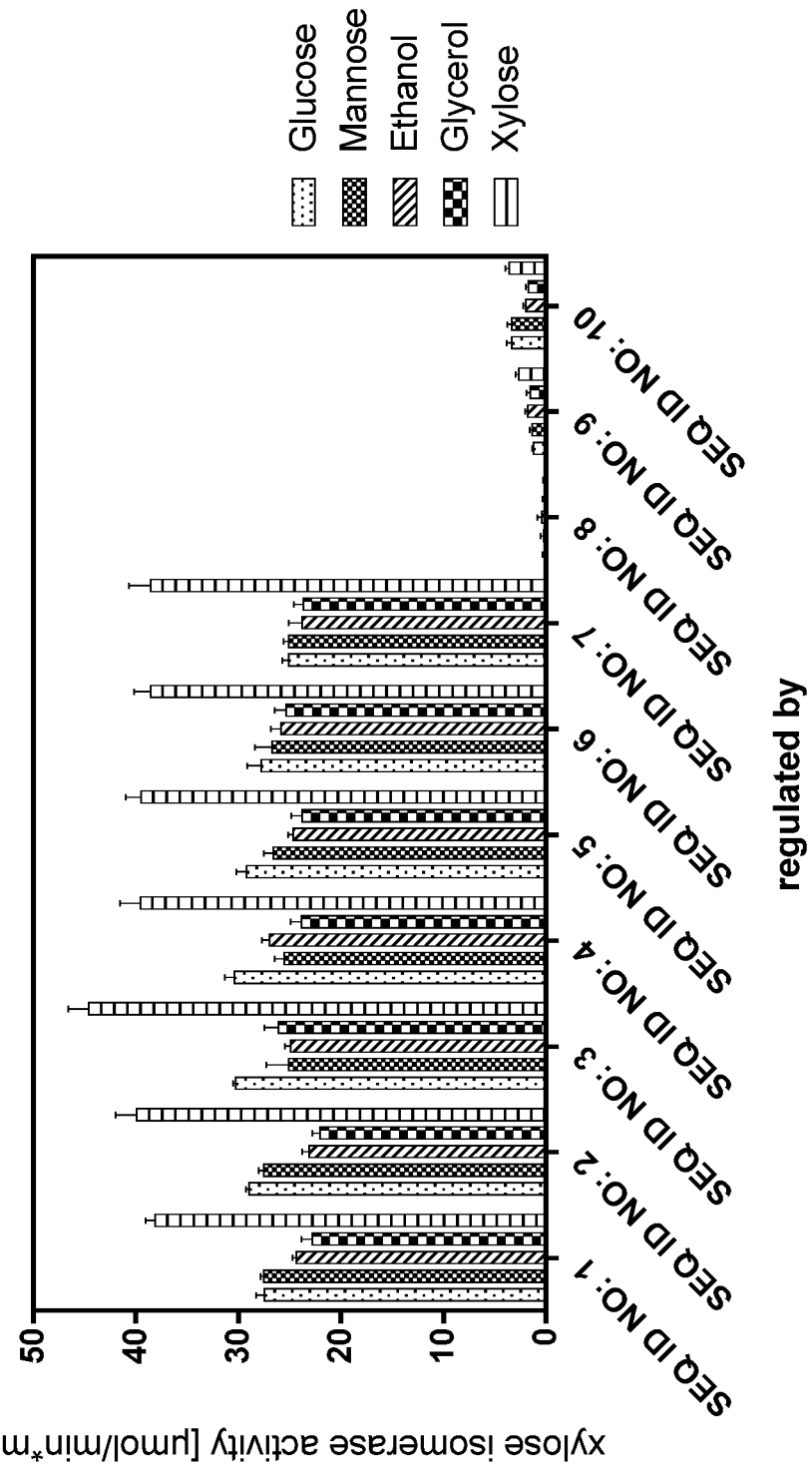

FIG. 4 shows a 14 to 25 fold increase of the enzyme activity of the reporter system under the control of the oligonucleotides according to the present invention (SEQ ID NOs 1 to 7) compared to the state of the art oligonucleotides SEQ ID NO 8, SEQ ID NO: 9 and SEQ ID NO: 10 on different substrates (glucose, mannose, ethanol, glycerol and xylose)

```
Sequence Listing Description:
SEQ. ID NO: 1: synthetic oligonucleotide consisting of a combina-
tion of SEQ. ID NO: 9 and SEQ. ID NO: 8
ccattctctg ctgctttgtt gcatcgtatc atcgcccgtt tcagccagtc ccgcataccc        60
cctttgcaac gttaacgtta ccgctagcgt ttaccatctc cacgctaaaa ggaaaacgaa       120
gattaagata aagttgggta aaatccgggg taagaggcaa gggggtagag aaaaaaaaac       180
cggagtcatt atatacgata ccgtccaggg taagacagtg atttctagct tccacttttt       240
tcaatttctt tttttcgttc caaatggcgt ccacccgtac atccggaatc tgacggcaca       300
agagccgatt agtggaagcc acggttacgt gattgcggtt ttttttcct acgtataacg        360
ctatgacggt agttgaatgt taaaaacgaa aacagagata ttgaattgac tcgtaggaac       420
aatttcgggc ccctgcgtgt tcttctgagg ttcatctttt acatttgctt ctgctggata       480
atttttcagag gcaacaagga aaaattagat ggcaaaaagt cgtctttcaa ggaaaaatcc      540
ccaccatctt tcgagatccc ctgtaactta ttggcaactg aaagaatgaa aaggaggaaa       600
atacaaaata tactagaact gaaaaaaaaa agtataaata agagacgata tatgccaata       660
cttcacaatg ttcgaatcta ttcttcattt gcagctattg taaaataata aaacatcaag       720
aacaaacaag ctcaacttgt cttttctaag aacaagaat aaacacaaaa acaaaaagtt        780
tttttaatttt taatcaaaaa                                                   800

SEQ. ID NO: 2: synthetic oligonucleotide corresponding to SEQ. ID
NO: 1 comprising the following mutations: g315a, c322g, a623-, t679c
ccattctctg ctgctttgtt gcatcgtatc atcgcccgtt tcagccagtc ccgcataccc        60
cctttgcaac gttaacgtta ccgctagcgt ttaccatctc cacgctaaaa ggaaaacgaa       120
gattaagata aagttgggta aaatccgggg taagaggcaa gggggtagag aaaaaaaaac       180
cggagtcatt atatacgata ccgtccaggg taagacagtg atttctagct tccacttttt       240
tcaatttctt tttttcgttc caaatggcgt ccacccgtac atccggaatc tgacggcaca       300
agagccgatt agtgaaagcc agggttacgt gattgcggtt ttttttcct acgtataacg        360
ctatgacggt agttgaatgt taaaaacgaa aacagagata ttgaattgac tcgtaggaac       420
aatttcgggc ccctgcgtgt tcttctgagg ttcatctttt acatttgctt ctgctggata       480
atttttcagag gcaacaagga aaaattagat ggcaaaaagt cgtctttcaa ggaaaaatcc      540
ccaccatctt tcgagatccc ctgtaactta ttggcaactg aaagaatgaa aaggaggaaa       600
atacaaaata tactagaact gaaaaaaaaa agtataaata gagacgatat atgccaatac       660
ttcacaatgt tcgaatccat tcttcatttg cagctattgt aaaataataa aacatcaaga       720
acaaacaagc tcaacttgtc ttttctaaga caaagaata aacacaaaaa caaaaagttt        780
ttttaatttt aatcaaaaa                                                    799

SEQ. ID NO: 3: synthetic oligonucleotide corresponding to SEQ. ID
NO: 1 comprising the following mutations:
t549c, a622-, a623-, c661a, t679c
ccattctctg ctgctttgtt gcatcgtatc atcgcccgtt tcagccagtc ccgcataccc        60
cctttgcaac gttaacgtta ccgctagcgt ttaccatctc cacgctaaaa ggaaaacgaa       120
gattaagata aagttgggta aaatccgggg taagaggcaa gggggtagag aaaaaaaaac       180
cggagtcatt atatacgata ccgtccaggg taagacagtg atttctagct tccacttttt       240
tcaatttctt tttttcgttc caaatggcgt ccacccgtac atccggaatc tgacggcaca       300
agagccgatt agtggaagcc acggttacgt gattgcggtt ttttttcct acgtataacg        360
ctatgacggt agttgaatgt taaaaacgaa aacagagata ttgaattgac tcgtaggaac       420
aatttcgggc ccctgcgtgt tcttctgagg ttcatctttt acatttgctt ctgctggata       480
atttttcagag gcaacaagga aaaattagat ggcaaaaagt cgtctttcaa ggaaaaatcc      540
ccaccatcct tcgagatccc ctgtaactta ttggcaactg aaagaatgaa aaggaggaaa       600
atacaaaata tactagaact gaaaaaaaaa gtataaatag agacgatata tgccaataat       660
tcacaatgtt cgaatccatt cttcatttgc agctattgta aaataataaa acatcaagaa       720
caaacaagct caacttgtct tttctaagaa caaagaataa acacaaaaac aaaaagtttt       780
tttaatttta atcaaaaa                                                    798

SEQ. ID NO: 4: synthetic oligonucleotide corresponding to SEQ.
ID NO: 1 comprising the following mutations: c495a, g674a, t679c, a687g
ccattctctg ctgctttgtt gcatcgtatc atcgcccgtt tcagccagtc ccgcataccc        60
cctttgcaac gttaacgtta ccgctagcgt ttaccatctc cacgctaaaa ggaaaacgaa       120
gattaagata aagttgggta aaatccgggg taagaggcaa gggggtagag aaaaaaaaac       180
cggagtcatt atatacgata ccgtccaggg taagacagtg atttctagct tccacttttt       240
tcaatttctt tttttcgttc caaatggcgt ccacccgtac atccggaatc tgacggcaca       300
agagccgatt agtggaagcc acggttacgt gattgcggtt ttttttcct acgtataacg        360
ctatgacggt agttgaatgt taaaaacgaa aacagagata ttgaattgac tcgtaggaac       420
aatttcgggc ccctgcgtgt tcttctgagg ttcatctttt acatttgctt ctgctggata       480
atttttcagag gcaaaaagga aaaattagat ggcaaaaagt cgtctttcaa ggaaaaatcc      540
ccaccatctt tcgagatccc ctgtaactta ttggcaactg aaagaatgaa aaggaggaaa       600
atacaaaata tactagaact gaaaaaaaaa agtataaat agagacgata tatgccaata       660
cttcacaatg ttcaaatcca ttcttcgttt gcagctattg taaaataata aaacatcaag       720
aacaaacaag ctcaacttgt cttttctaag aacaaagaat aaacacaaaa acaaaaagtt      780
tttttaattt taatcaaaaa                                                   800
```

SEQ. ID NO: 5: synthetic oligonucleotide corresponding to SEQ. ID
NO: 1 comprising the following mutations:
a171-, c322g, c430t, c431t, c495a

```
ccattctctg ctgctttgtt gcatcgtatc atcgcccgtt tcagccagtc ccgcatacccc    60
cctttgcaac gttaacgtta ccgctagcgt ttaccatctc cacgctaaaa ggaaaacgaa    120
gattaagata aagttgggta aaatccgggg taagaggcaa gggggtagag aaaaaaaacc    180
ggagtcatta tatacgatac cgtccagggt aagacagtga tttctagctt ccactttttt    240
caatttcttt ttttcgttcc aaatggcgtc cacccgtaca tccggaatct gacggcacaa    300
gagccgatta gtggaagcca gggttacgtg attgcggttt ttttttccta cgtataacgc    360
tatgacggta gttgaatgtt aaaaacgaaa acagagatat tgaattgact cgtaggaaca    420
atttcgggtt cctgcgtgtt cttctgaggt tcatcttta catttgcttc tgctggataa    480
ttttcagagg caaaaaggaa aaattagatg gcaaaaagtc gtctttcaag gaaaaatccc    540
caccatcttt cgagatcccc tgtaacttat tggcaactga agaatgaaa aggaggaaaa    600
tacaaaatat actagaactg aaaaaaaaaa agtataaata gagacgatat atgcaaatac    660
ttcacaatgt tcgaatctat tcttcatttg cagctattgt aaaataataa aacatcaaga    720
acaaacaagc tcaacttgtc ttttctaaga acaaagaata aacacaaaaa caaaaagttt    780
ttttaattt  aatcaaaaa                                                 799
```

SEQ. ID NO: 6: synthetic oligonucleotide corresponding to SEQ. ID
NO: 1 comprising the following mutations: c181a,
c205t, c322g, t549c, a623-, t679c

```
ccattctctg ctgctttgtt gcatcgtatc atcgcccgtt tcagccagtc ccgcatacccc    60
cctttgcaac gttaacgtta ccgctagcgt ttaccatctc cacgctaaaa ggaaaacgaa    120
gattaagata aagttgggta aaatccgggg taagaggcaa gggggtagag aaaaaaaaac    180
aggagtcatt atatacgata ccgttcaggg taagacagtg atttctagct tccactttt     240
tcaatttctt ttttcgttc  caaatggcgt ccacccgtac atccggaatc tgacggcaca    300
agagccgatt agtggaagcc agggttacgt gattgcggtt tttttttcct acgtataacg    360
ctatgacggt agttgaatgt taaaaacgaa aacagagata ttgaattgac tcgtaggaac    420
aatttcgggc cctgcgtgt  tcttctgagg ttcatctttt acatttgctt ctgctggata    480
attttcagag gcaacaagga aaaattagat ggcaaaaagt cgtctttcaa ggaaaaatcc    540
ccaccatcct tcgagatccc ctgtaactta ttggcaactg aaagaatgaa aaggaggaaa    600
atacaaaata tactagaact gaaaaaaaaa agtataaata gagacgatat atgcaaatac    660
ttcacaatgt tcgaatccat tcttcatttg cagctattgt aaaataataa aacatcaaga    720
acaaacaagc tcaacttgtc ttttctaaga acaaagaata aacacaaaaa caaaaagttt    780
ttttaattt  aatcaaaaa                                                 799
```

SEQ. ID NO: 7: synthetic oligonucleotide corresponding to SEQ.
ID NO: 1 comprising the following mutations: t186a, c322g,
c430t, c431t, a623-, t679c

```
ccattctctg ctgctttgtt gcatcgtatc atcgcccgtt tcagccagtc ccgcatacccc    60
cctttgcaac gttaacgtta ccgctagcgt ttaccatctc cacgctaaaa ggaaaacgaa    120
gattaagata aagttgggta aaatccgggg taagaggcaa gggggtagag aaaaaaaaac    180
cggagacatt atatacgata ccgtccaggg taagacagtg atttctagct tccactttt     240
tcaatttctt ttttcgttc  caaatggcgt ccacccgtac atccggaatc tgacggcaca    300
agagccgatt agtggaagcc agggttacgt gattgcggtt tttttttcct acgtataacg    360
ctatgacggt agttgaatgt taaaaacgaa aacagagata ttgaattgac tcgtaggaac    420
aatttcgggt tcctgcgtgt tcttctgagg ttcatctttt acatttgctt ctgctggata    480
attttcagag gcaacaagga aaaattagat ggcaaaaagt cgtctttcaa ggaaaaatcc    540
ccaccatctt tcgagatccc ctgtaactta ttggcaactg aaagaatgaa aaggaggaaa    600
atacaaaata tactagaact gaaaaaaaaa agtataaata gagacgatat atgcaaatac    660
ttcacaatgt tcgaatccat tcttcatttg cagctattgt aaaataataa aacatcaaga    720
acaaacaagc tcaacttgtc ttttctaaga acaaagaata aacacaaaaa caaaaagttt    780
ttttaattt  aatcaaaaa                                                 799
```

SEQ. ID NO: 8:
oligonucleotide from *Saccharomyces cereyisiae* 5288C, upstream region of
PFK2

SEQ. ID NO: 9:
oligonucleotide from *Saccharomyces cereyisiae* 5288C, upstream region of
HXT7

SEQ. ID NO: 10:
oligonucleotide from *Saccharomyces cereyisiae* 5288C, upstream region of
PGK1

SEQ. ID NO: 11:
protein with aldose -1-epimerase activity from *Saccharomyces cereyisiae*
EC1118, 104_6579

SEQ. ID NO: 12:
protein with aldose -1-epimerase activity from *Saccharomyces cerevisiae*
EC1119, 1F14_0056

SEQ. ID NO: 13:
protein with aldose -1-epimerase activity from *Saccharomyces cerevisiae*
S288C, YHR210C SEQ. ID NO: 14: protein with aldose -1-epimerase activity from
*Saccharomyces cerevisiae* x *Saccharomyces kudriavzevii* VI N7, YHR210C-like -continued SEQ. ID NO: 15:
protein with aldose-1-epimerase activity from *Saccharomyces cerevisiae* AWRI796, YHR210C-like SEQ. ID NO: 16:
protein with aldose-1-epimerase activity from *Lactococcus lactis*, XylM SEQ. ID NO: 17:
protein with xylose isomerase activity from *Eubacterium saburreum*, XylA SEQ. ID NO: 18:
protein with xylose isomerase activity from *Piromyces* sp. E2, XylA SEQ. ID NO: 19:
protein with xylose isomerase activity from *Orpinomyces* sp. ukk1, XylA SEQ. ID NO: 20:
protein with xylose isomerase activity from *Clostridium phytofermentans*, XylA SEQ. ID NO: 21:
protein with xylose isomerase activity from *Ruminococcus flavefaciens*, XylA SEQ. ID NO: 22:
protein with xylose isomerase activity from *Bacteroides uniformis*, XylA SEQ. ID NO: 23:
protein with xylose isomerase activity from *Clostridium cellulolyticum*, XylA SEQ. ID NO: 24:
protein with xylose isomerase activity from *Thermotoga maritima*, XylA SEQ. ID NO: 25:
protein with xylose isomerase activity from *Bacillus stearothermophilus*, XylA SEQ. ID NO: 26:
protein with xylose isomerase activity from *Bacteroides stercoris*, XylA SEQ. ID NO: 27:
protein with xylose isomerase activity from *Parabacteroides distasonis*, XylA SEQ. ID NO: 28:
protein with xylose isomerase activity from *Prevotella ruminicola*, XylA SEQ. ID NO: 29:
protein with xylose isomerase activity from *Agrobacterium tumefaciens*, XylA SEQ. ID NO: 30:
protein with xylose isomerase activity from *Clostridium cellulovorans*, XylA SEQ. ID NO: 31:
protein with xylose isomerase activity from *Burkholderia cenocepacia*, XylA SEQ. ID NO: 32:
protein with xylose isomerase activity from *Lactococcus lactis*, XylA protein SEQ. ID NO: 33:
protein with xylose isomerase activity from *Thermoanaerobacter thermohydrosulfuricus*, XylA SEQ. ID NO: 34:
protein with xylose isomerase activity from *Reticulitermes speratus*, XylA protein, XylA SEQ. ID NO: 35:
protein with xylose isomerase activity from uncultured bacteria from cow rumen, sequence number 2 within WO 2014 164392

SEQ. ID NO: 36:
protein with xylose isomerase activity from uncultured bacteria from cow rumen, sequence number 1 within WO 2014 164392

SEQ. ID NO: 37:
protein with xylose isomerase activity from *Lachnospiraceae bacterium* ICM7, XylA -continued SEQ. ID NO: 38:
protein with xylose isomerase activity from *Lachnospiraceae bacterium* oral
taxon 107, XylA SEQ. ID NO: 39:
protein with xylose isomerase activity from *Lachnospiraceae bacterium* oral
taxon 082, XylA SEQ. ID NO: 40:
protein with xylose isomerase activity from uncultured bacterium, XYM1
from Parachin,N.S. and Gorwa-Grauslund, M.F. Isola-
tion of xylose isomerases
by sequence- and function-based screening from a soil metagenome library,
*Biotechnol Biofuels* 4 (1), 9 (2011)

SEQ. ID NO: 41:
protein with xylose isomerase activity from uncultured bacterium, XYM2
from Parachin,N.S. and Gorwa-Grauslund, M.F. Isola-
tion of xylose isomerases
by sequence- and function-based screening from a soil metagenome library,
*Biotechnol Biofuels* 4 (1), 9 (2011)

SEQ. ID NO: 42:
protein with xylose isomerase activity from *Thermus thermophilus*, XylA SEQ. ID NO: 43:
protein with xylose isomerase activity from *Escherichia coli*, XylA SEQ. ID NO: 44:
protein with xylulokinase activity from *Saccharomyces cereyi-
siae* 5288C, XKS1

SEQ. ID NO: 45:
protein with xylulokinase activity from *Scheffersomyces* (Pichia) *stip-
ites* CBS
6054, XKS1

SEQ. ID NO: 46:
protein with xylulokinase activity from *Trichoderma reesei* QM6a,
TRIREDRAFT_123288

SEQ. ID NO: 47:
protein with transaldolase activity from *Saccharomyces cereyisiae* 5288C,
TAL1

SEQ. ID NO: 48:
protein with transaldolase activity from *Saccharomyces cereyisiae* 5288C,
NQM1

SEQ. ID NO: 49:
protein with transaldolase activity from *Scheffersomyces* (Pichia)
6054, TAL1

SEQ. ID NO: 50:
protein with transketolase activity from *Saccharomyces cereyisiae* S288C,
*stipitis* CBS TKL1

SEQ. ID NO: 51:
protein with transketolase activity from *Saccharomyces cereyisiae* S288C,
TKL2

SEQ. ID NO: 52:
protein with transketolase activity from *Scheffersomyces* (Pichia)
*stipitis* CBS 6054, TKL1

SEQ. ID NO: 53:
protein with aldcohol dehydrogenase activity from *Saccharomyces
cereyisiae* 5288C, ADH1

SEQ. ID NO: 54: synthetic DNA sequence encoding for SEQ. ID NO: 17
```
atgaaggaat tcttcccagg tatttctcca gttaagttcg aaggtagaga ctctaagaac      60
ccattgtctt tcaagtacta cgacgctaag agagttatta tgggtaagac catggaagaa    120
cacttgtctt tcgctatggc ttggtggcac aacttgtgtg cttgtggtgt tgacatgttc    180
ggtcaaggta ccgttgacaa gtctttcggt gaatcttctg gtaccatgga acacgctaga    240
gctaaggttg acgctggtat tgaattcatg aagaagttgg gtattaagta ctactgtttc    300
cacgacaccg acattgttcc agaagaccaa gaagacatta cgttaccaa cgctagattg    360
gacgaaatta ccgactacat tttggaaaag accaaggaca ccgacattaa gtgtttgtgg    420
accacctgta acatgttctc taacccaaga ttcatgaacg tgctggttc ttctaactct    480
gctgacgttt tctgtttcgc tgctgctcaa gctaagaagg gtttggaaaa cgctgttaag    540
ttgggtgcta agggtttcgt tttctggggt ggtagagaag gttacgaaac cttgttgaac    600
```

-continued

```
accgacatga agttggaaga agaaaacatt gctaccttgt tcaccatgtg tagagactac    660
ggtagatcta ttggtttcat gggtgacttc tacattgaac caaagccaaa ggaaccaatg    720
aagcaccaat acgacttcga cgctgctacc gctattggtt tcttgagaaa gtacggtttg    780
gacaaggact tcaagttgaa cattgaagct aaccacgcta ccttggctgg tcacaccttc    840
caacacgaat tgagagtttg tgctgttaac ggtatgatgg ttctgttga cgctaaccaa     900
ggtgacacct tgttgggttg ggacaccgac caattcccaa ccaacgttta cgacaccacc    960
ttggctatgt acgaaatttt gaaggctggt ggtttgagag gtggtttgaa cttcgactct   1020
aagaacagaa gaccatctaa caccgctgac gacatgttct acggtttcat tgctggtatg   1080
gacaccttcg ctttgggttt gattaaggct gctgaaatta ttgaagacgg tagaattgac   1140
gacttcgtta aggaaagata cgcttcttac aactctggta ttggtaagaa gattagaaac   1200
agaaaggtta ccttgattga atgtgctgaa tacgctgcta agttgaagaa gccagaattg   1260
ccagaatctg gtagacaaga atacttggaa tctgttgtca acaacatttt gttcggtggt   1320
tctggttaa                                                          1329
```

What is claimed is:

1. An oligonucleotide comprising a sequence at least 90% identical to SEQ ID NO: 1; wherein said oligonucleotide, when present in yeast cells cultivated in the presence of glucose, mannose, ethanol, glycerol, or xylose, increases growth of the yeast cells.

2. The oligonucleotide of claim 1, wherein said sequence is at least 95% identical to SEQ ID NO: 1.

3. The oligonucleotide of claim 2, wherein said sequence is at least 98% identical to SEQ ID NO: 1.

4. The oligonucleotide of claim 3, wherein said sequence is at least 99% identical to SEQ ID NO: 1.

5. The oligonucleotide of claim 1, wherein said sequence is selected from the group consisting of SEQ ID NOS: 2-7.

6. The oligonucleotide of claim 1, wherein the oligonucleotide, when present in yeast cells cultivated in the presence of glucose, mannose, ethanol, glycerol, or xylose, increases expression of XylA mRNA in the cells.

7. The oligonucleotide of claim 6, wherein the increase in XylA mRNA expression is about 4-fold to about 29-fold.

8. The oligonucleotide of claim 1, wherein the oligonucleotide, when present in yeast cells cultivated in the presence of glucose, mannose, ethanol, glycerol, or xylose, increases expression of xylose isomerase enzyme activity in the cells.

9. The oligonucleotide of claim 8, wherein the increase in xylose isomerase enzyme activity expression is about 14-fold to about 25-fold.

10. A recombinant DNA fragment comprising said sequence of claim 1.

11. A yeast cell expression plasmid comprising at least one recombinant DNA fragment of claim 10.

12. A yeast cell comprising the plasmid of claim 11.

* * * * *